(12) United States Patent
Mitra et al.

(10) Patent No.: US 8,183,360 B2
(45) Date of Patent: May 22, 2012

(54) POPULATION SCALE HLA-TYPING AND USES THEREOF

(75) Inventors: Rahul Mitra, Pearland, TX (US); Krishna Jayaraman, Hoffman Estates, IL (US); Frederick H. Eggers, Tuscon, AZ (US); Michäel E. Hogan, Tuscon, AZ (US)

(73) Assignee: Genomics USA, Inc, Hoffman Estates, IL (US)

( * ) Notice: Subject to any disclaimer, the term of this patent is extended or adjusted under 35 U.S.C. 154(b) by 0 days.

(21) Appl. No.: 12/660,002

(22) Filed: Feb. 18, 2010

(65) Prior Publication Data

US 2010/0279889 A1 Nov. 4, 2010

Related U.S. Application Data

(62) Division of application No. 11/711,561, filed on Feb. 27, 2007, now Pat. No. 7,667,026.

(60) Provisional application No. 60/777,078, filed on Feb. 27, 2006.

(51) Int. Cl.
*C07H 21/04* (2006.01)

(52) U.S. Cl. .................................. 536/24.33; 536/24.3

(58) Field of Classification Search ........................ None
See application file for complete search history.

(56) References Cited

U.S. PATENT DOCUMENTS

| 4,582,788 | A | 4/1986 | Erlich |
|---|---|---|---|
| 5,567,809 | A | 10/1996 | Apple |
| 6,670,124 | B1 | 12/2003 | Chow |
| 2005/0260662 | A1 | 11/2005 | Yang |

FOREIGN PATENT DOCUMENTS

| WO | WO 9704087 A1 * | 2/1997 |
|---|---|---|
| WO | WO 0031295 A1 * | 6/2000 |

* cited by examiner

*Primary Examiner* — Young J Kim
(74) *Attorney, Agent, or Firm* — Benjamin Aaron Adler

(57) ABSTRACT

The present invention provides a portable system for real-time population-scale HLA genotyping and/or allelotyping in a field environment and methods of such population-scale HLA genotyping. The individual components of the system are portable to and operable within a field environment thereby providing high throughput with real-time geno- or allelotyping. Also provided are HLA gene-specific primers and HLA allele-specific or single nucleotide polymorphism-specific hybridization probes. In addition the present invention provides a microarray comprising the hybridization probes. Further provided is a kit comprising the HLA gene-specific primers and the microarray.

8 Claims, 17 Drawing Sheets

| Probe designs | Codon 09 | Codon 20 | Codon 24 | Codon 31 | Codon 50 | Codon 57 | Codon 59 |
|---|---|---|---|---|---|---|---|
| Concensus Sequence Variant 1 | TAC | CCC | TCA | ACC | CCG | CCG | TAT |
| Variant 2 | GAC | CTC | GCA | ACG | CCT | CCT | TTT |
| Variant 3 | CAC | | | | | | |
| UCLA Cl-072 *0702/*3508 | TAC/TAC | CCC/CCC | TCA/GCA | ACS/ACC | CCG/CCA | CCK/CCG | TAT/TAT |
| Sequencing | TAC | CCC | TCA/GCA | ACC | CCG/CCA | CCG | TAT |
| Array | TAC | CCC | TCA/GCA | ACC | CCG/CCA | CCG | TAT |
| UCLA Cl-023 *1401/*5501 | TAC/TAC | CCC/CCC | TCA/GCA | ACG/ACG | CCG/CCG | CCG/CCG | TAT/TAT |
| Sequencing | TAC | CCC | TCA/GCA | ACG | CCG | CCG | TAT |
| Array | TAC | CCC | TCA/GCA | ACG | CCG | CCG | TAT |
| UCLA Cl-021 *27XX/*7301 | CAC/CAC | CCC/CCC | ACC/ACC | ACG/ACC | CCG/CCG | CCG/CCG | TAT/TAT |
| Sequencing | CAC | CCC | ACC/ACC | ACC | CCG | CCG | TAT |
| Array | CAC | CCC | NP/NP | ACC/2SNP | CCG | CCG | TAT |
| UCLA Cl-055 *0702/*8101 | TAC/TAC | CCC/CCC | TCA/TCA | ACC/ACC | CCG/CCG | CCG/CCG | TAT/TAT |
| Sequencing | TAC | CCC | TCA | ACC | CCG | CCG | TAT |
| Array | TAC | CCC | TCA | ACC | CCG | CCG | TAT |
| UCLA Cl-060- *5502/*5601 | TAC/TAC | CCC/CCC | GCA/GCA | ACG/ACG | CCG/CCG | CCG/CCG | TAT/TAT |
| Sequencing | TAC | CCC | GCA | ACG | CCG | CCG | TAT |
| Array | TAC | CCC | GCA | ACG | CCG | CCG | TAT |
| UCLA Cl-007 *1521/*15XX | TAC/TAC | CCC/CCC | GCA/DCM | ACC/ACS | CCA/CCR | CCG/CCG | TAT/TAT |
| Sequencing | TAC | CCC | GCA | ACC | CCA | CCG | TAT |
| Array | TAC | CCC | GCA | ACC | CCA | CCG | TAT |
| UCLA Cl-026 *4403/*5801 | TAC/TAC | CCC/CCC | ACC/GCA | ACG/ACC | CCA/CCA | CCG/CCG | TAT/TAT |
| Sequencing | TAC | CCC | GCA | ACC | CCA | CCG | TAT |
| Array | TAC | CCC | NP/GCA | ACC | CCA | CCG | TAT |
| UCLA Cl-027 *1515/*4001 | TAC/CAC | CCC/CCC | GCA/ACC | ACC/ACG | CCA/CCR | CCG/CCG | TAT/TAT |
| Sequencing | TAC/CAC | CCC | RCM | ACC/ACG | CCA | CCG | TAT |
| Array | TAC/CAC | CCC | GCA/NP | ACC/ACG | CCA | CCG | TAT |
| UCLA Cl-057 *0702/*0801 | TAC/GAC | CCC/CCC | TCA/TCA | ACS/ACG | CCG/CCG | CCK/CCG | TAT/TAT |
| Sequencing | TAC/GAC | CCC | TCA | ACC/ACG | CCG | CCG | TAT |
| Array | TAC/GAC | CCC | TCA | ACC/ACG | CCG | CCG | TAT |
| UCLA Cl-051 *4006/*4601 | CAC/TAC | CCC/CCC | ACC/GCA | ACG/ACC | CCA/CCA | CCG/CCG | TAT/TAT |
| Sequencing | CAC/TAC | CCC | RCM | ACG/ACC | CCA | CCG | TAT |
| Array | CAC/TAC | CCC | NP/GCA | 2SNP/ACC | CCA | CCG | TAT |
| UCLA Cl-039 *4011/*4101 | CAC/CAC | CCC/CCC | ACC/ACC | ACG/ACG | CCA/CCA | CCG/CCG | TAT/TAT |
| Sequencing | CAC | CCC | ACC | ACG | CCA | CCG | TAT |
| Array | CAC | CCC | NP | 2SNP | CCG/CCA | CCG | TAT |
| UCLA Cl-044 *5101/*1501 | TAC/TAC | CCC/CCC | GCA/GCA | ACC/ACS | CCR/CCA | CCG/CCG | TAT/TAT |
| Sequencing | TAC | CCC | GCA | ACC | CCA | CCG | TAT |
| Array | TAC | CCC | GCA | ACC | CCA | CCG | TAT |

Fig. 6A

| Probe designs | Codon 67 | Codon 69 | Codon 74 | Codon 84 |
|---|---|---|---|---|
| Concensus Sequence Variant 1 | TAC | GCCCAGGCA (SEQ ID NO:308) | GAC | TAC |
| Variant 2 | TGC | ACCAACACA (SEQ ID NO:309) | TAC | CAC |
| Variant 3 | TTC | | | |
| UCLA CI-072 *0702/*3508 | TAC/TTC | GCCCAGGCA/ACCAACACA | GAC/TAC | TAC/TAC |
| Sequencing | TAC/TTC | RCCMASRCA (SEQ ID NO: 310) | GAC/TAC | TAC |
| Array | TAC/TTC | GCCCAGGCA/ACCAACACA | GAC/TAC | TAC |
| UCLA CI-023 *1401/*5501 | TGC/TAC | GCCCAGGCA/ACCAACACA | GAC/GAC | TAC/TAC |
| Sequencing | TGC/TAC | RCCMASRCA | GAC | TAC |
| Array | TGC/TAC | GCCCAGGCA/ACCAACACA | GAC | TAC |
| UCLA CI-021 *27XX/*7301 | TNC/TGC | RCCMASRCA/GCCAAGGCA (SEQ ID NO: 311) | KAC/GAC | TAC/TAC |
| Sequencing | TGC | AMBIGUOUS | GAC | TAC |
| Array | TGC | NP/NP | GAC | TAC |
| UCLA CI-055 *0702/*8101 | TAC/TAC | GCCCAGGCA/GCCCAGGCA | GAC/GAC | TAC/TAC |
| Sequencing | TAC | GCCCAGGCA | GAC | TAC |
| Array | TAC | GCCCAGGCA | GAC | TAC |
| UCLA CI-060- *5502/*5601 | TAC/TAC | GCCCAGGCA/GCCCAGGCA | GAC/GAC | TAC/TAC |
| Sequencing | TAC | GCCCAGGCA | GAC | TAC |
| Array | TAC | GCCCAGGCA | GAC | TAC |
| UCLA CI-007 *1521/*15XX | TAGC/TNC | ACCAACACA/RYCHMSRCR (SEQ ID NO:312) | TAC/KAC | TAC/TAC |
| Sequencing | TSC | ACCAACACA | TAC | TAC |
| Array | 2SNP | ACCAACACA | TAC | TAC |
| UCLA CI-026 *4403/*5801 | TCC/ATG | ACCAACACA/GCCTCCGCG (SEQ ID NO:313) | TAC/TAC | TAC/TAC |
| Sequencing | ATG | GCCTCCGCG | TAC | TAC |
| Array | NP/NP | NO CALL/NP | TAC | TAC |
| UCLA CI-027 *1515/*4001 | TCC/TCC | ACCAACACA/ACCAACACA | TAC/TAC | TAC/TAC |
| Sequencing | TCC | ACCAACACA | TAC | TAC |
| Array | NP/NP | ACCAACACA | TAC | TAC |
| UCLA CI-057 *0702/*0801 | TAC/TTC | GCCCAGGCA/ACCAACACA | GAC/GAC | TAC/TAC |
| Sequencing | TAC/TTC | GCCCAGGCA/ACCAACACA | GAC | TAC |
| Array | TAC/TTC | GCCCAGGCA/ACCAACACA | GAC | TAC |
| UCLA CI-051 *4006/*4601 | TCC/TAC | ACCAACACA/SSCCAGGCA (SEQ ID NO:314) | TAC/GAC | TAC/TAC |
| Sequencing | TCC/TAC | MSCMASRCA (SEQ ID NO: 315) | TAC/GAC | TAC |
| Array | NP/2SNP | ACCAACACA/NP | 2SNP/GAC | TAC |
| UCLA CI-039 *4011/*4101 | TCC/TCC | ACCAACACA/ACCAACACA | TAC/TAC | TAC/TAC |
| Sequencing | TCC | ACCAACACA | TAC | TAC |
| Array | NP/NP | ACCAACACA | TAC | TAC |
| UCLA CI-044 *5101/*1501 | TTC/TCC | ACYAACACA (SEQ ID NO: 316)/ACCAACACA | TAC/TAC | TAC/TAC |
| Sequencing | TYC | ACCAACACA | TAC | TAC |
| Array | TTC/NP | ACCAACACA | TAC | TAC |

Fig. 6B

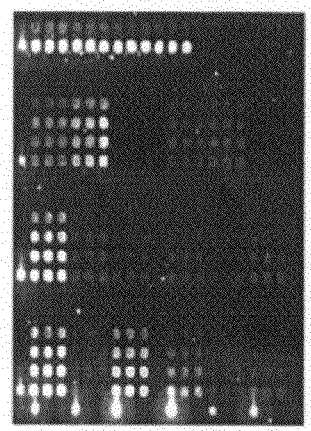 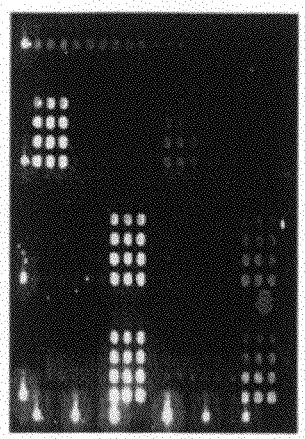 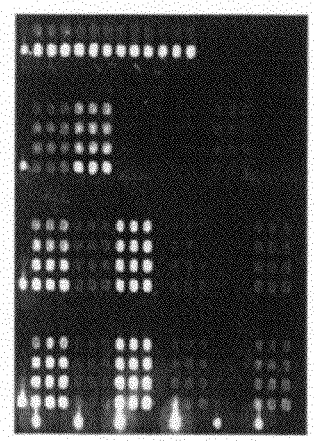
Fig.7A  Fig.7B  Fig.7C
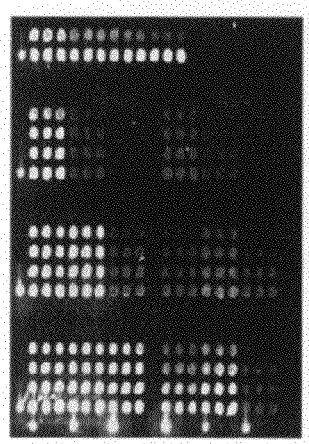 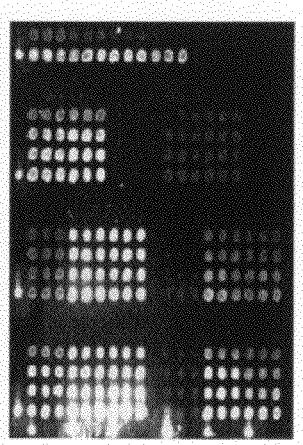 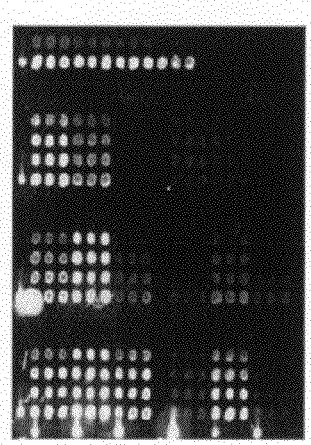
Fig.7D  Fig.7E  Fig.7F

| HLA-A | hits | HLA-B | hits | HLA-B cont | hits | HLA-C | hits |
|---|---|---|---|---|---|---|---|
| A*0102 | 2 | B*0703 | 3 | B*4101 | 2 | Cw*0106 | 1 |
| A*0103 | 2 | B*0707 | 1 | B*4102 | 1 | Cw*0313 | 1 |
| A*0104N | 1 | B*0708 | 2 | B*4104 | 2 | Cw*0314 | 1 |
| A*0202 | 4 | B*0709 | 2 | B*4201 | 1 | Cw*0315 | 1 |
| A*0204 | 6 | B*0720 | 1 | B*4202 | 3 | Cw*0403 | 2 |
| A*0205 | 7 | B*0726 | 1 | B*420502 | 1 | Cw*0408 | 1 |
| A*0207 | 9 | B*0732 | 1 | B*4405 | 4 | Cw*0409N | 2 |
| A*0209 | 2 | B*0802 | 1 | B*4413 | 1 | Cw*0602 | 33 |
| A*0211 | 4 | B*0804 | 2 | B*4415 | 2 | Cw*080102 | 1 |
| A*0214 | 1 | B*0809 | 1 | B*4417 | 1 | Cw*0807 | 1 |
| A*0216 | 1 | B*0811 | 1 | B*4422 | 1 | Cw*120201 | 1 |
| A*0226 | 1 | B*1301 | 3 | B*4423N | 1 | Cw*1209 | 1 |
| A*0232N | 1 | B*1304 | 1 | B*4425 | 1 | Cw*1210 | 1 |
| A*0240 | 1 | B*1311 | 1 | B*4426 | 1 | Cw*1507 | 1 |
| A*0248 | 1 | B*1403 | 3 | B*4427 | 1 | Cw*1602 | 2 |
| A*0249 | 1 | B*1502 | 3 | B*4431 | 1 | Cw*1701 | 1 |
| A*0252 | 1 | B*1503 | 4 | B*4437 | 1 | | |
| A*0302 | 2 | B*1513 | 2 | B*4501 | 2 | | |
| A*0310 | 1 | B*1521 | 1 | B*4601 | 0 | | |
| A*1102 | 2 | B*1545 | 1 | B*4703 | 3 | | |
| A*1107 | 1 | B*1546 | 1 | B*4704 | 1 | | |
| A*1108 | 1 | B*1567 | 1 | B*4801 | 6 | | |
| A*2301 | 7 | B*1568 | 1 | B*4902 | 1 | | |
| A*2306 | 1 | B*1817N | 1 | B*5002 | 4 | | |
| A*24020102L | 1 | B*2701 | 5 | B*5103 | 2 | | |
| A*2602 | 2 | B*2702 | 15 | B*5105 | 2 | | |
| A*2608 | 2 | B*2703 | 6 | B*5107 | 1 | | |
| A*2614 | 1 | B*2706 | 8 | B*5108 | 5 | | |
| A*2615 | 1 | B*2709 | 15 | B*5110 | 1 | | |
| A*2903 | 2 | B*2712 | 2 | B*5111N | 1 | | |
| A*3004 | 1 | B*2723 | 1 | B*5401 | 6 | | |
| A*3301 | 4 | B*3503 | 11 | B*5502 | 2 | | |
| A*3306 | 1 | B*3520 | 3 | B*5504 | 1 | | |
| A*6601 | 2 | B*3531 | 1 | B*5509 | 9 | | |
| A*6802 | 9 | B*3701 | 3 | B*5514 | 1 | | |
| A*6808 | 1 | B*3705 | 1 | B*5601 | 4 | | |
| A*6812 | 1 | B*3801 | 1 | B*5602 | 1 | | |
| A*6813 | 1 | B*3805 | 1 | B*5603 | 1 | | |
| A*6901 | 2 | B*3905 | 3 | B*560502 | 1 | | |
| A*8001 | 4 | B*3909 | 1 | B*5606 | 9 | | |
| | | B*3910 | 2 | B*5614 | 4 | | |
| | | B*3911 | 1 | B*5801 | 8 | | |
| | | B*3924 | 3 | B*5802 | 1 | | |
| | | B*3928 | 1 | B*5809 | 1 | | |
| | | B*4012 | 1 | B*7301 | 4 | | |
| | | B*4013 | 1 | B*8101 | 4 | | |
| | | B*4034 | 1 | B*8102 | 1 | | |
| | | B*4046 | 1 | B*8201 | 1 | | |

Fig. 10A

| HLA-DRB | hits | HLA-DPB1 | hits | HLA-DQ | hits | Others | hits |
|---|---|---|---|---|---|---|---|
| DRB1*0103 | 16 | DPB1*0402 | 10 | DQA1*0103 | 13 | DMA*0103 | 2 |
| DRB1*0312 | 2033 | DPB1*0501 | 14 | DQA1*0106 | 666 | DMA*0104 | 2 |
| DRB1*0313 | 2033 | DPB1*0901 | 4 | DQA1*0201 | 670 | DRA*0101 | 3 |
| DRB1*0402 | 2041 | DPB1*8401 | 362 | DQA1*0302 | 6 | F*010101 | 1 |
| DRB1*0404 | 28 | DPB1*8501 | 1 | DQA1*0303 | 4 | F*010102 | 1 |
| DRB1*0408 | 3 | DPB1*9001 | 1 | DQA1*040102 | 1 | G*0105N | 9 |
| DRB1*0410 | 5 | | | DQA1*0402 | 1 | | |
| DRB1*0411 | 1 | | | DQA1*0404 | 1 | | |
| DRB1*0432 | 2033 | | | DQA1*0505 | 1 | | |
| DRB1*0436 | 1 | | | DQB1*0202 | 3 | | |
| DRB1*0704 | 1 | | | DQB1*0304 | 1 | | |
| DRB1*0806 | 1 | | | DQB1*0401 | 10 | | |
| DRB1*0807 | 2 | | | DQB1*0402 | 5 | | |
| DRB1*0818 | 1 | | | DQB1*0602 | 109 | | |
| DRB1*090103 | 2033 | | | DQB1*0603 | 12 | | |
| DRB1*1137 | 2033 | | | DQB1*0609 | 1 | | |
| DRB1*1139 | 2033 | | | | | | |
| DRB1*1143 | 1 | | | | | | |
| DRB1*1208 | 1 | | | | | | |
| DRB1*1212 | 2033 | | | | | | |
| DRB1*1305 | 3 | | | | | | |
| DRB1*1318 | 1 | | | | | | |
| DRB1*1402 | 8 | | | | | | |
| DRB1*1404 | 3 | | | | | | |
| DRB1*140502 | 1 | | | | | | |
| DRB1*1437 | 2033 | | | | | | |
| DRB1*1503 | 4 | | | | | | |
| DRB3*0106 | 120 | | | | | | |
| DRB3*0107 | 120 | | | | | | |
| DRB3*0209 | 120 | | | | | | |

Fig. 10B

```
                        SEQUENCE LISTING

<160> NUMBER OF SEQ ID NOS: 319

<210> SEQ ID NO 1
<211> LENGTH: 20
<212> TYPE: DNA
<213> ORGANISM: artificial sequence
<220> FEATURE:
<223> OTHER INFORMATION: forward primer for exon 2 of HLA-B locus

<400> SEQUENCE: 1
gctcccactc catgaggtat                                                   20

<210> SEQ ID NO 2
<211> LENGTH: 20
<212> TYPE: DNA
<213> ORGANISM: artificial sequence
<220> FEATURE:
<223> OTHER INFORMATION: reverse primer for exon 2 of HLA-B locus

<400> SEQUENCE: 2
atacctcatg gagtgggagc                                                   20

<210> SEQ ID NO 3
<211> LENGTH: 16
<212> TYPE: DNA
<213> ORGANISM: artificial sequence
<220> FEATURE:
<223> OTHER INFORMATION: forward primer for exon 2 of HLA-B locus

<400> SEQUENCE: 3
ccactccatg aggtat                                                       16

<210> SEQ ID NO 4
<211> LENGTH: 14
<212> TYPE: DNA
<213> ORGANISM: artificial sequence
<220> FEATURE:
<223> OTHER INFORMATION: reverse primer for exon 2 of HLA-B locus

<400> SEQUENCE: 4
gaaaccgggt aaac                                                         14
```

```
<210> SEQ ID NO 5
<211> LENGTH: 16
<212> TYPE: DNA
<213> ORGANISM: artificial sequence
<220> FEATURE:
<223> OTHER INFORMATION: reverse primer for exon 2 of HLA-B locus

<400> SEQUENCE: 5
atgaaaccgg gtaaac                                                     16

<210> SEQ ID NO 6
<211> LENGTH: 23
<212> TYPE: DNA
<213> ORGANISM: artificial sequence
<220> FEATURE:
<223> OTHER INFORMATION: forward primer for exon 3 of HLA-B locus

<400> SEQUENCE: 6
acccggttta cccggttcat ttg                                             23

<210> SEQ ID NO 7
<211> LENGTH: 18
<212> TYPE: DNA
<213> ORGANISM: artificial sequence
<220> FEATURE:
<223> OTHER INFORMATION: forward primer for exon 3 of HLA-B locus

<400> SEQUENCE: 7
gtttacccgg ttcatttg                                                   18

<210> SEQ ID NO 8
<211> LENGTH: 16
<212> TYPE: DNA
<213> ORGANISM: artificial sequence
<220> FEATURE:
<223> OTHER INFORMATION: forward primer for exon 3 of HLA-B locus

<400> SEQUENCE: 8
ttacccggtt catttg                                                     16

<210> SEQ ID NO 9
<211> LENGTH: 13
<212> TYPE: DNA
<213> ORGANISM: artificial sequence
<220> FEATURE:
<223> OTHER INFORMATION: forward primer for exon 3 of HLA-B locus

<400> SEQUENCE: 9
gtttacccgg ttc                                                        13

<210> SEQ ID NO 10
<211> LENGTH: 14
<212> TYPE: DNA
<213> ORGANISM: artificial sequence
<220> FEATURE:
<223> OTHER INFORMATION: forward primer for exon 3 of HLA-B locus

<400> SEQUENCE: 10
acccggttca tttg                                                       14

<210> SEQ ID NO 11
<211> LENGTH: 12
<212> TYPE: DNA
<213> ORGANISM: artificial sequence
<220> FEATURE:
<223> OTHER INFORMATION: forward primer for exon 3 of HLA-B locus
```

```
<400> SEQUENCE: 11
acccggttca tt                                                          12

<210> SEQ ID NO 12
<211> LENGTH: 15
<212> TYPE: DNA
<213> ORGANISM: artificial sequence
<220> FEATURE:
<223> OTHER INFORMATION: forward primer for exon 3 of HLA-B locus

<400> SEQUENCE: 12
tacccggttc atttg                                                       15

<210> SEQ ID NO 13
<211> LENGTH: 13
<212> TYPE: DNA
<213> ORGANISM: artificial sequence
<220> FEATURE:
<223> OTHER INFORMATION: forward primer for exon 3 of HLA-B locus

<400> SEQUENCE: 13
tttacccggt tca                                                         13

<210> SEQ ID NO 14
<211> LENGTH: 20
<212> TYPE: DNA
<213> ORGANISM: artificial sequence
<220> FEATURE:
<223> OTHER INFORMATION: forward primary primer for HLA-A locus

<400> SEQUENCE: 14
gcctctgygg ggagaagcaa                                                  20

<210> SEQ ID NO 15
<211> LENGTH: 22
<212> TYPE: DNA
<213> ORGANISM: artificial sequence
<220> FEATURE:
<223> OTHER INFORMATION: reverse primary primer for HLA-A locus

<400> SEQUENCE: 15
gtcccaattg tctcccctcc tt                                               22

<210> SEQ ID NO 16
<211> LENGTH: 22
<212> TYPE: DNA
<213> ORGANISM: artificial sequence
<220> FEATURE:
<223> OTHER INFORMATION: forward primary primer for HLA-B locus

<400> SEQUENCE: 16
gggaggagmg agggaccgc ag                                                22

<210> SEQ ID NO 17
<211> LENGTH: 24
<212> TYPE: DNA
<213> ORGANISM: artificial sequence
<220> FEATURE:
<223> OTHER INFORMATION: reverse primary primer for HLA-B locus

<400> SEQUENCE: 17
ttctccattc aasggagggc gaca                                             24

<210> SEQ ID NO 18
<211> LENGTH: 23
```

```
<212> TYPE: DNA
<213> ORGANISM: artificial sequence
<220> FEATURE:
<223> OTHER INFORMATION: reverse primary primer for HLA-B locus

<400> SEQUENCE: 18
ggaggccatc ccgggcgatc tat                                          23

<210> SEQ ID NO 19
<211> LENGTH: 23
<212> TYPE: DNA
<213> ORGANISM: artificial sequence
<220> FEATURE:
<223> OTHER INFORMATION: reverse primary primer for HLA-B locus

<400> SEQUENCE: 19
ggaggccatc cccggcgacc tat                                          23

<210> SEQ ID NO 20
<211> LENGTH: 22
<212> TYPE: DNA
<213> ORGANISM: artificial sequence
<220> FEATURE:
<223> OTHER INFORMATION: forward secondary primer for HLA-A exon 2

<400> SEQUENCE: 20
agccgcgcck ggaggagggt cg                                           22

<210> SEQ ID NO 21
<211> LENGTH: 20
<212> TYPE: DNA
<213> ORGANISM: artificial sequence
<220> FEATURE:
<223> OTHER INFORMATION: reverse secondary primer for HLA-A exon 2

<400> SEQUENCE: 21
gcccgtccgt gggggatgag                                              20

<210> SEQ ID NO 22
<211> LENGTH: 24
<212> TYPE: DNA
<213> ORGANISM: artificial sequence
<220> FEATURE:
<223> OTHER INFORMATION: forward secondary primer for HLA-A exon 3

<400> SEQUENCE: 22
caaaaatccc cccrggttgg tcgg                                         24

<210> SEQ ID NO 23
<211> LENGTH: 22
<212> TYPE: DNA
<213> ORGANISM: artificial sequence
<220> FEATURE:
<223> OTHER INFORMATION: reverse secondary primer for HLA-A exon 3

<400> SEQUENCE: 23
ggcccctggt acccgtgcgc tg                                           22

<210> SEQ ID NO 24
<211> LENGTH: 22
<212> TYPE: DNA
<213> ORGANISM: artificial sequence
<220> FEATURE:
<223> OTHER INFORMATION: forward secondary primer for HLA-A exon 3

<400> SEQUENCE: 24
gtttcatttt cagtttaggc ca                                           22
```

```
<210> SEQ ID NO 25
<211> LENGTH: 22
<212> TYPE: DNA
<213> ORGANISM: artificial sequence
<220> FEATURE:
<223> OTHER INFORMATION: reverse secondary primer for HLA-A exon 3

<400> SEQUENCE: 25
gtgcgctgca gcgtctcctt cc                                              22

<210> SEQ ID NO 26
<211> LENGTH: 22
<212> TYPE: DNA
<213> ORGANISM: artificial sequence
<220> FEATURE:
<223> OTHER INFORMATION: reverse secondary primer for HLA-A exon 3

<400> SEQUENCE: 26
gtgcgctgca gcgtctcctt cc                                              22

<210> SEQ ID NO 27
<211> LENGTH: 22
<212> TYPE: DNA
<213> ORGANISM: artificial sequence
<220> FEATURE:
<223> OTHER INFORMATION: forward secondary primer for HLA-B exon 2

<400> SEQUENCE: 27
gagccgcgcc ggkaggaggg tc                                              22

<210> SEQ ID NO 28
<211> LENGTH: 22
<212> TYPE: DNA
<213> ORGANISM: artificial sequence
<220> FEATURE:
<223> OTHER INFORMATION: reverse secondary primer for HLA-B exon 2

<400> SEQUENCE: 28
ggtcactcac cgkcctcgct ct                                              22

<210> SEQ ID NO 29
<211> LENGTH: 17
<212> TYPE: DNA
<213> ORGANISM: artificial sequence
<220> FEATURE:
<223> OTHER INFORMATION: forward secondary primer for HLA-B exon 3

<400> SEQUENCE: 29 gggggccaggg tctcaca                                                   17

<210> SEQ ID NO 30
<211> LENGTH: 18
<212> TYPE: DNA
<213> ORGANISM: artificial sequence
<220> FEATURE:
<223> OTHER INFORMATION: reverse secondary primer for HLA-B exon 3

<400> SEQUENCE: 30
cccactgccc ctggtacc                                                   18

<210> SEQ ID NO 31
<211> LENGTH: 21
<212> TYPE: DNA
<213> ORGANISM: artificial sequence
<220> FEATURE:
<223> OTHER INFORMATION: reverse secondary primer for HLA-B exon 3
```

<400> SEQUENCE: 31
cgggccgtmc gtgggggatg g                                                 21

<210> SEQ ID NO 32
<211> LENGTH: 21
<212> TYPE: DNA
<213> ORGANISM: artificial sequence
<220> FEATURE:
<223> OTHER INFORMATION: forward primary primer for HLA-DRB locus

<400> SEQUENCE: 32
cttggaggtc tccagaacag g                                                 21

<210> SEQ ID NO 33
<211> LENGTH: 21
<212> TYPE: DNA
<213> ORGANISM: artificial sequence
<220> FEATURE:
<223> OTHER INFORMATION: forward primary primer for HLA-DRB locus

<400> SEQUENCE: 33
cttagaggtc tccagaaccg g                                                 21

<210> SEQ ID NO 34
<211> LENGTH: 22
<212> TYPE: DNA
<213> ORGANISM: artificial sequence
<220> FEATURE:
<223> OTHER INFORMATION: reverse primary primer for HLA-DRB locus

<400> SEQUENCE: 34
gcccccagca cccacctccc tt                                                22

<210> SEQ ID NO 35
<211> LENGTH: 22
<212> TYPE: DNA
<213> ORGANISM: artificial sequence
<220> FEATURE:
<223> OTHER INFORMATION: reverse primary primer for HLA-DRB locus

<400> SEQUENCE: 35 gcccctgta ccccctccc ac                                                  22

<210> SEQ ID NO 36
<211> LENGTH: 22
<212> TYPE: DNA
<213> ORGANISM: artificial sequence
<220> FEATURE:
<223> OTHER INFORMATION: reverse primary primer for HLA-DRB locus

<400> SEQUENCE: 36
gctccgtgca cccacctccc tt                                                22

<210> SEQ ID NO 37
<211> LENGTH: 22
<212> TYPE: DNA
<213> ORGANISM: artificial sequence
<220> FEATURE:
<223> OTHER INFORMATION: reverse primary primer for HLA-DRB locus

<400> SEQUENCE: 37
gccgcccgca cccacctccc tt                                                22

<210> SEQ ID NO 38
<211> LENGTH: 20

```
<212> TYPE: DNA
<213> ORGANISM: artificial sequence
<220> FEATURE:
<223> OTHER INFORMATION: forward primary primer for HLA-DRB exon 2

<400> SEQUENCE: 38
cacagcacgt ttcttggagg                                              20

<210> SEQ ID NO 39
<211> LENGTH: 21
<212> TYPE: DNA
<213> ORGANISM: artificial sequence
<220> FEATURE:
<223> OTHER INFORMATION: forward primary primer for HLA-DRB exon 2

<400> SEQUENCE: 39
tccccacagc acgtttcttg a                                            21

<210> SEQ ID NO 40
<211> LENGTH: 21
<212> TYPE: DNA
<213> ORGANISM: artificial sequence
<220> FEATURE:
<223> OTHER INFORMATION: forward primary primer for HLA-DRB exon 2

<400> SEQUENCE: 40
tccccacagc acgtttcttg a                                            21

<210> SEQ ID NO 41
<211> LENGTH: 21
<212> TYPE: DNA
<213> ORGANISM: artificial sequence
<220> FEATURE:
<223> OTHER INFORMATION: forward primary primer for HLA-DRB exon 2

<400> SEQUENCE: 41
tccccacagc acgtttcttg a                                            21

<210> SEQ ID NO 42
<211> LENGTH: 22
<212> TYPE: DNA
<213> ORGANISM: artificial sequence
<220> FEATURE:
<223> OTHER INFORMATION: forward primary primer for HLA-DRB exon 2

<400> SEQUENCE: 42
cagcacgttt cttggagcag gt                                           22

<210> SEQ ID NO 43
<211> LENGTH: 22
<212> TYPE: DNA
<213> ORGANISM: artificial sequence
<220> FEATURE:
<223> OTHER INFORMATION: forward primary primer for HLA-DRB exon 2

<400> SEQUENCE: 43
cagcacgttt cttggagcag gt                                           22

<210> SEQ ID NO 44
<211> LENGTH: 22
<212> TYPE: DNA
<213> ORGANISM: artificial sequence
<220> FEATURE:
<223> OTHER INFORMATION: forward primary primer for HLA-DRB exon 2

<400> SEQUENCE: 44
cccacagcac gtttcttgga gt                                           22
```

```
<210> SEQ ID NO 45
<211> LENGTH: 25
<212> TYPE: DNA
<213> ORGANISM: artificial sequence
<220> FEATURE:
<223> OTHER INFORMATION: reverse primary primer for HLA-DRB exon 2

<400> SEQUENCE: 45
cacacacaca cacacactca gattc                                         25

<210> SEQ ID NO 46
<211> LENGTH: 25
<212> TYPE: DNA
<213> ORGANISM: artificial sequence
<220> FEATURE:
<223> OTHER INFORMATION: reverse primary primer for HLA-DRB exon 2

<400> SEQUENCE: 46
cacacacaca accacactca gattc                                         25

<210> SEQ ID NO 47
<211> LENGTH: 25
<212> TYPE: DNA
<213> ORGANISM: artificial sequence
<220> FEATURE:
<223> OTHER INFORMATION: reverse primary primer for HLA-DRB exon 2

<400> SEQUENCE: 47
cacacacaca cacagagtca gattc                                         25

<210> SEQ ID NO 48
<211> LENGTH: 30
<212> TYPE: DNA
<213> ORGANISM: artificial sequence
<220> FEATURE:
<223> OTHER INFORMATION: sense probe for HLA-A exon 2 codon 2 variant 1

<400> SEQUENCE: 48 ttttttttg ctcccactcc acttttttt                                      30

<210> SEQ ID NO 49
<211> LENGTH: 30
<212> TYPE: DNA
<213> ORGANISM: artificial sequence
<220> FEATURE:
<223> OTHER INFORMATION: sense probe for HLA-A exon 2 codon 2 variant 2

<400> SEQUENCE: 49
ttttttttgc tctcactcca ttttttttt                                     30

<210> SEQ ID NO 50
<211> LENGTH: 30
<212> TYPE: DNA
<213> ORGANISM: artificial sequence
<220> FEATURE:
<223> OTHER INFORMATION: antisense probe for HLA-A exon 2 codon 2
      variant 1

<400> SEQUENCE: 50
tttttttttt ggagtgggag ctcttttttt                                    30

<210> SEQ ID NO 51
<211> LENGTH: 30
<212> TYPE: DNA
<213> ORGANISM: artificial sequence
<220> FEATURE:
```

```
<223> OTHER INFORMATION: antisense probe for HLA-A exon 2 codon 2
      variant 2

<400> SEQUENCE: 51 ttttttttcta tggagtgaga gctcttttttt                                    30

<210> SEQ ID NO 52
<211> LENGTH: 30
<212> TYPE: DNA
<213> ORGANISM: artificial sequence
<220> FEATURE:
<223> OTHER INFORMATION: sense probe for HLA-A exon 2 codon 9 variant 1

<400> SEQUENCE: 52 tttttttgt atttcttcac atcttttttt                                       30

<210> SEQ ID NO 53
<211> LENGTH: 30
<212> TYPE: DNA
<213> ORGANISM: artificial sequence
<220> FEATURE:
<223> OTHER INFORMATION: sense probe for HLA-A exon 2 codon 9 variant 3

<400> SEQUENCE: 53 tttttttgt atttctccac attttttttt                                       30

<210> SEQ ID NO 54
<211> LENGTH: 30
<212> TYPE: DNA
<213> ORGANISM: artificial sequence
<220> FEATURE:
<223> OTHER INFORMATION: antisense probe for HLA-A exon 2 codon 9
      variant 1

<400> SEQUENCE: 54
ttttttttat gtgaagaaat actcttttttt                                     30

<210> SEQ ID NO 55
<211> LENGTH: 30
<212> TYPE: DNA
<213> ORGANISM: artificial sequence
<220> FEATURE:
<223> OTHER INFORMATION: antisense probe for HLA-A exon 2 codon 17
      variant 3

<400> SEQUENCE: 55
tttttttttg tggagaaata ctcttttttt                                      30

<210> SEQ ID NO 56
<211> LENGTH: 30
<212> TYPE: DNA
<213> ORGANISM: artificial sequence
<220> FEATURE:
<223> OTHER INFORMATION: sense probe for HLA-A exon 2 codon 17 variant 1

<400> SEQUENCE: 56 ttttttttc cgcggggagc ttttttttt                                        30

<210> SEQ ID NO 57
<211> LENGTH: 30
<212> TYPE: DNA
<213> ORGANISM: artificial sequence
<220> FEATURE:
<223> OTHER INFORMATION: sense probe for HLA-A exon 2 codon 17 variant 2

<400> SEQUENCE: 57 ttttttttc agtggagagc ccttttttt                                        30
```

-continued

```
<210> SEQ ID NO 58
<211> LENGTH: 30
<212> TYPE: DNA
<213> ORGANISM: artificial sequence
<220> FEATURE:
<223> OTHER INFORMATION: antisense probe for HLA-A exon 2 codon 17
      variant 1

<400> SEQUENCE: 58 ttttttttc tccccgcggc tttttttttt                                      30

<210> SEQ ID NO 59
<211> LENGTH: 30
<212> TYPE: DNA
<213> ORGANISM: artificial sequence
<220> FEATURE:
<223> OTHER INFORMATION: antisense probe for HLA-A exon 2 codon 17
      variant 2

<400> SEQUENCE: 59 ttttttttg ctctccactg cctttttttt                                      30

<210> SEQ ID NO 60
<211> LENGTH: 30
<212> TYPE: DNA
<213> ORGANISM: artificial sequence
<220> FEATURE:
<223> OTHER INFORMATION: sense probe for HLA-A exon 2 codon 24 variant 1

<400> SEQUENCE: 60
tttttttttt tcatcgccgt gtttttttttt                                    30

<210> SEQ ID NO 61
<211> LENGTH: 30
<212> TYPE: DNA
<213> ORGANISM: artificial sequence
<220> FEATURE:
<223> OTHER INFORMATION: sense probe for HLA-A exon 2 codon 24 variant 2

<400> SEQUENCE: 61
tttttttttc ttcatcgcag tgtttttttt                                     30

<210> SEQ ID NO 62
<211> LENGTH: 30
<212> TYPE: DNA
<213> ORGANISM: artificial sequence
<220> FEATURE:
<223> OTHER INFORMATION: antisense probe for HLA-A exon 2 codon 24
      variant 1

<400> SEQUENCE: 62 tttttttcc acggcgatga attttttttt                                      30

<210> SEQ ID NO 63
<211> LENGTH: 30
<212> TYPE: DNA
<213> ORGANISM: artificial sequence
<220> FEATURE:
<223> OTHER INFORMATION: antisense probe for HLA-A exon 2 codon 24
      variant 2

<400> SEQUENCE: 63 tttttttcc actgcgatga agtttttttt                                      30

<210> SEQ ID NO 64
<211> LENGTH: 30
```

```
<212> TYPE: DNA
<213> ORGANISM: artificial sequence
<220> FEATURE:
<223> OTHER INFORMATION: sense probe for HLA-A exon 2 codon 36 variant 1

<400> SEQUENCE: 64
ttttttttct cggttcgaca gctttttttt                                              30

<210> SEQ ID NO 65
<211> LENGTH: 30
<212> TYPE: DNA
<213> ORGANISM: artificial sequence
<220> FEATURE:
<223> OTHER INFORMATION: sense probe for HLA-A exon 2 codon 36 variant 2

<400> SEQUENCE: 65 ttttttttctc ggtttgacag cgtttttttt                                             30

<210> SEQ ID NO 66
<211> LENGTH: 30
<212> TYPE: DNA
<213> ORGANISM: artificial sequence
<220> FEATURE:
<223> OTHER INFORMATION: antisense probe for HLA-A exon 2 codon 36
      variant 1

<400> SEQUENCE: 66
tttttttttc tgtcgaaccg cttttttttt                                              30

<210> SEQ ID NO 67
<211> LENGTH: 30
<212> TYPE: DNA
<213> ORGANISM: artificial sequence
<220> FEATURE:
<223> OTHER INFORMATION: antisense probe for HLA-A exon 2 codon 36
      variant 2

<400> SEQUENCE: 67
tttttttctg ctgtcaaacc gcttttttt                                               30

<210> SEQ ID NO 68
<211> LENGTH: 30
<212> TYPE: DNA
<213> ORGANISM: artificial sequence
<220> FEATURE:
<223> OTHER INFORMATION: sense probe for HLA-A exon 2 codon 44 variant 1

<400> SEQUENCE: 68 ttttttttc cagaggatgg agttttttttt                                              30

<210> SEQ ID NO 69
<211> LENGTH: 30
<212> TYPE: DNA
<213> ORGANISM: artificial sequence
<220> FEATURE:
<223> OTHER INFORMATION: sense probe for HLA-A exon 2 codon 44 variant 2

<400> SEQUENCE: 69 ttttttttc cagaagatgg agttttttttt                                              30

<210> SEQ ID NO 70
<211> LENGTH: 30
<212> TYPE: DNA
<213> ORGANISM: artificial sequence
<220> FEATURE:
<223> OTHER INFORMATION: antisense probe for HLA-A exon 2 codon 44
      variant 1
```

-continued

```
<400> SEQUENCE: 70
tttttttttc catcttctgg ccttttttt                                      30

<210> SEQ ID NO 71
<211> LENGTH: 30
<212> TYPE: DNA
<213> ORGANISM: artificial sequence
<220> FEATURE:
<223> OTHER INFORMATION: antisense probe for HLA-A exon 2 codon 44
      variant 2

<400> SEQUENCE: 71
tttttttttc catcttctgg ccttttttt                                      30

<210> SEQ ID NO 72
<211> LENGTH: 30
<212> TYPE: DNA
<213> ORGANISM: artificial sequence
<220> FEATURE:
<223> OTHER INFORMATION: sense probe for HLA-A exon 2 codon 49 variant 1

<400> SEQUENCE: 72
tttttttttt gggcgccgtg tttttttttt                                     30

<210> SEQ ID NO 73
<211> LENGTH: 30
<212> TYPE: DNA
<213> ORGANISM: artificial sequence
<220> FEATURE:
<223> OTHER INFORMATION: sense probe for HLA-A exon 2 codon 49 variant 2

<400> SEQUENCE: 73
tttttttttc gggcaccgtg tttttttttt                                     30

<210> SEQ ID NO 74
<211> LENGTH: 30
<212> TYPE: DNA
<213> ORGANISM: artificial sequence
<220> FEATURE:
<223> OTHER INFORMATION: antisense probe for HLA-A exon 2 codon 49
      variant 1

<400> SEQUENCE: 74
ttttttttct cacggcgccc tttttttttt                                     30

<210> SEQ ID NO 75
<211> LENGTH: 30
<212> TYPE: DNA
<213> ORGANISM: artificial sequence
<220> FEATURE:
<223> OTHER INFORMATION: antisense probe for HLA-A exon 2 codon 49
      variant 2

<400> SEQUENCE: 75
tttttttttc ccacggtgcc cttttttttt                                     30

<210> SEQ ID NO 76
<211> LENGTH: 30
<212> TYPE: DNA
<213> ORGANISM: artificial sequence
<220> FEATURE:
<223> OTHER INFORMATION: sense probe for HLA-A exon 2 codon 56 variant 1

<400> SEQUENCE: 76
ttttttttta ggggccggag ctttttttt                                      30
```

-continued

```
<210> SEQ ID NO 77
<211> LENGTH: 30
<212> TYPE: DNA
<213> ORGANISM: artificial sequence
<220> FEATURE:
<223> OTHER INFORMATION: sense probe for HLA-A exon 2 codon 56 variant 2

<400> SEQUENCE: 77
tttttttttg agggtccgga gctttttttt                                    30

<210> SEQ ID NO 78
<211> LENGTH: 30
<212> TYPE: DNA
<213> ORGANISM: artificial sequence
<220> FEATURE:
<223> OTHER INFORMATION: antisense probe for HLA-A exon 2 codon 56
      variant 1

<400> SEQUENCE: 78
tttttttttt ccggcccctc tcttttttt                                     30

<210> SEQ ID NO 79
<211> LENGTH: 30
<212> TYPE: DNA
<213> ORGANISM: artificial sequence
<220> FEATURE:
<223> OTHER INFORMATION: antisense probe for HLA-A exon 2 codon 56
      variant 2

<400> SEQUENCE: 79
tttttttctc tccggaccct ctcttttttt                                    30

<210> SEQ ID NO 80
<211> LENGTH: 30
<212> TYPE: DNA
<213> ORGANISM: artificial sequence
<220> FEATURE:
<223> OTHER INFORMATION: sense probe for HLA-A exon 2 codon 62 variant 1

<400> SEQUENCE: 80
tttttttctg gaccaggaga cttttttttt                                    30

<210> SEQ ID NO 81
<211> LENGTH: 30
<212> TYPE: DNA
<213> ORGANISM: artificial sequence
<220> FEATURE:
<223> OTHER INFORMATION: sense probe for HLA-A exon 2 codon 62 variant 4

<400> SEQUENCE: 81
tttttttctg gacgaggaga cttttttttt                                    30

<210> SEQ ID NO 82
<211> LENGTH: 30
<212> TYPE: DNA
<213> ORGANISM: artificial sequence
<220> FEATURE:
<223> OTHER INFORMATION: antisense probe for HLA-A exon 2 codon 62
      variant 1

<400> SEQUENCE: 82 tttttttcg tctcctggtc cttttttttt                                     30

<210> SEQ ID NO 83
<211> LENGTH: 30
<212> TYPE: DNA
<213> ORGANISM: artificial sequence
<220> FEATURE:
```

<223> OTHER INFORMATION: antisense probe for HLA-A exon 2 codon 62
       variant 4

<400> SEQUENCE: 83
ttttttttcg tctcctcgtc cttttttttt                                     30

<210> SEQ ID NO 84
<211> LENGTH: 30
<212> TYPE: DNA
<213> ORGANISM: artificial sequence
<220> FEATURE:
<223> OTHER INFORMATION: sense probe for HLA-A exon 2 codon 66 variant 1

<400> SEQUENCE: 84
ttttttttgg aatgtgaagg cttttttttt                                     30

<210> SEQ ID NO 85
<211> LENGTH: 30
<212> TYPE: DNA
<213> ORGANISM: artificial sequence
<220> FEATURE:
<223> OTHER INFORMATION: sense probe for HLA-A exon 2 codon 66 variant 2

<400> SEQUENCE: 85
ttttttttgg aaagtgaagg cttttttttt                                     30

<210> SEQ ID NO 86
<211> LENGTH: 30
<212> TYPE: DNA
<213> ORGANISM: artificial sequence
<220> FEATURE:
<223> OTHER INFORMATION: antisense probe for HLA-A exon 2 codon 66
       variant 1

<400> SEQUENCE: 86
ttttttttcc ttcacattcc gttctttttt                                     30

<210> SEQ ID NO 87
<211> LENGTH: 30
<212> TYPE: DNA
<213> ORGANISM: artificial sequence
<220> FEATURE:
<223> OTHER INFORMATION: antisense probe for HLA-A exon 2 codon 66
       variant 2

<400> SEQUENCE: 87
ttttttttcc ttcactttcc gttctttttt                                     30

<210> SEQ ID NO 88
<211> LENGTH: 30
<212> TYPE: DNA
<213> ORGANISM: artificial sequence
<220> FEATURE:
<223> OTHER INFORMATION: sense probe for HLA-A exon 2 codon 70 variant 1

<400> SEQUENCE: 88
ttttttttgc ccactcacag aactttttttt                                    30

<210> SEQ ID NO 89
<211> LENGTH: 30
<212> TYPE: DNA
<213> ORGANISM: artificial sequence
<220> FEATURE:
<223> OTHER INFORMATION: sense probe for HLA-A exon 2 codon 70 variant 2

<400> SEQUENCE: 89
ttttttttgc ccagtcacag aactttttttt                                    30

<210> SEQ ID NO 90
<211> LENGTH: 30
<212> TYPE: DNA
<213> ORGANISM: artificial sequence
<220> FEATURE:
<223> OTHER INFORMATION: antisense probe for HLA-A exon 2 codon 70
      variant 1

<400> SEQUENCE: 90
tttttttttc tgtgactggg ctcttttttt                                   30

<210> SEQ ID NO 91
<211> LENGTH: 30
<212> TYPE: DNA
<213> ORGANISM: artificial sequence
<220> FEATURE:
<223> OTHER INFORMATION: antisense probe for HLA-A exon 2 codon 70
      variant 2

<400> SEQUENCE: 91
tttttttttc tgtgactggg ctcttttttt                                   30

<210> SEQ ID NO 92
<211> LENGTH: 30
<212> TYPE: DNA
<213> ORGANISM: artificial sequence
<220> FEATURE:
<223> OTHER INFORMATION: sense probe for HLA-A exon 2 codon 76 variant 2

<400> SEQUENCE: 92
ttttttttcc gagagaacct gtttttttt                                    30

<210> SEQ ID NO 93
<211> LENGTH: 30
<212> TYPE: DNA
<213> ORGANISM: artificial sequence
<220> FEATURE:
<223> OTHER INFORMATION: sense probe for HLA-A exon 2 codon 76 variant 3

<400> SEQUENCE: 93
tttttttttc gagcgaacct gtttttttt                                    30

<210> SEQ ID NO 94
<211> LENGTH: 30
<212> TYPE: DNA
<213> ORGANISM: artificial sequence
<220> FEATURE:
<223> OTHER INFORMATION: antisense probe for HLA-A exon 2 codon 76
      variant 2

<400> SEQUENCE: 94
ttttttttca ggttctctcg gcttttttt                                    30

<210> SEQ ID NO 95
<211> LENGTH: 30
<212> TYPE: DNA
<213> ORGANISM: artificial sequence
<220> FEATURE:
<223> OTHER INFORMATION: antisense probe for HLA-A exon 2 codon 76
      variant 3

<400> SEQUENCE: 95
tttttttttc aggttcgctc gtcttttttt                                   30

<210> SEQ ID NO 96
<211> LENGTH: 30

```
<212> TYPE: DNA
<213> ORGANISM: artificial sequence
<220> FEATURE:
<223> OTHER INFORMATION: sense probe for HLA-A exon 2 codon 81 variant 1

<400> SEQUENCE: 96
tttttttttg accctgcgcg gtctttttttt                                      30

<210> SEQ ID NO 97
<211> LENGTH: 30
<212> TYPE: DNA
<213> ORGANISM: artificial sequence
<220> FEATURE:
<223> OTHER INFORMATION: sense probe for HLA-A exon 2 codon 81 variant 2

<400> SEQUENCE: 97
tttttttttg atcgcgctcc gtctttttttt                                      30

<210> SEQ ID NO 98
<211> LENGTH: 30
<212> TYPE: DNA
<213> ORGANISM: artificial sequence
<220> FEATURE:
<223> OTHER INFORMATION: antisense probe for HLA-A exon 2 codon 81
      variant 1

<400> SEQUENCE: 98
tttttttttc cgcgcagggt cttttttttt                                       30

<210> SEQ ID NO 99
<211> LENGTH: 30
<212> TYPE: DNA
<213> ORGANISM: artificial sequence
<220> FEATURE:
<223> OTHER INFORMATION: antisense probe for HLA-A exon 2 codon 81
      variant 2

<400> SEQUENCE: 99
tttttttttc ggagcgcgat cttttttttt                                       30

<210> SEQ ID NO 100
<211> LENGTH: 30
<212> TYPE: DNA
<213> ORGANISM: artificial sequence
<220> FEATURE:
<223> OTHER INFORMATION: sense probe for HLA-A exon 3 codon 95 variant 1

<400> SEQUENCE: 100 tttttttcttc acaccatcca gactttttttt                                     30

<210> SEQ ID NO 101
<211> LENGTH: 30
<212> TYPE: DNA
<213> ORGANISM: artificial sequence
<220> FEATURE:
<223> OTHER INFORMATION: sense probe for HLA-A exon 3 codon 95 variant 2

<400> SEQUENCE: 101 tttttttttcc acaccgtcca gactttttttt                                     30

<210> SEQ ID NO 102
<211> LENGTH: 30
<212> TYPE: DNA
<213> ORGANISM: artificial sequence
<220> FEATURE:
<223> OTHER INFORMATION: antisense probe for HLA-A exon 3 codon 95
      variant 1
```

-continued

```
<210> SEQ ID NO 103
<211> LENGTH: 30
<212> TYPE: DNA
<213> ORGANISM: artificial sequence
<220> FEATURE:
<223> OTHER INFORMATION: antisense probe for HLA-A exon 3 codon 95
      variant 2

<400> SEQUENCE: 103
tttttttatt ctggacggtg tgttttttt                                 30

<210> SEQ ID NO 104
<211> LENGTH: 30
<212> TYPE: DNA
<213> ORGANISM: artificial sequence
<220> FEATURE:
<223> OTHER INFORMATION: sense probe for HLA-A exon 3 codon 97 variant 1

<400> SEQUENCE: 104
tttttttttc cagaggatgt attttttttt                                30

<210> SEQ ID NO 105
<211> LENGTH: 30
<212> TYPE: DNA
<213> ORGANISM: artificial sequence
<220> FEATURE:
<223> OTHER INFORMATION: sense probe for HLA-A exon 3 codon 97 variant 3

<400> SEQUENCE: 105
tttttttttc cagatgatgt atgttttttt                                30

<210> SEQ ID NO 106
<211> LENGTH: 30
<212> TYPE: DNA
<213> ORGANISM: artificial sequence
<220> FEATURE:
<223> OTHER INFORMATION: antisense probe for HLA-A exon 3 codon 97
      variant 1

<400> SEQUENCE: 106
ttttttttat acatcctctg gaattttttt                                30

<210> SEQ ID NO 107
<211> LENGTH: 30
<212> TYPE: DNA
<213> ORGANISM: artificial sequence
<220> FEATURE:
<223> OTHER INFORMATION: antisense probe for HLA-A exon 3 codon 97
      variant 3

<400> SEQUENCE: 107
tttttttcat acatcatctg gaattttttt                                30

<210> SEQ ID NO 108
<211> LENGTH: 30
<212> TYPE: DNA
<213> ORGANISM: artificial sequence
<220> FEATURE:
<223> OTHER INFORMATION: sense probe for HLA-A exon 3 codon 105 variant
      1

<400> SEQUENCE: 108
tttttttttg gtcggacggg tttttttttt                                30
```

(SEQ ID NO 102 shown above:)

```
<400> SEQUENCE: 102 tttttttattc tggatggtgt cattttttttt                              30
```

```
<210> SEQ ID NO 109
<211> LENGTH: 30
<212> TYPE: DNA
<213> ORGANISM: artificial sequence
<220> FEATURE:
<223> OTHER INFORMATION: sense probe for HLA-A exon 3 codon 105 variant
      2

<400> SEQUENCE: 109
tttttttttg gccggacggg tttttttttt                                    30

<210> SEQ ID NO 110
<211> LENGTH: 30
<212> TYPE: DNA
<213> ORGANISM: artificial sequence
<220> FEATURE:
<223> OTHER INFORMATION: antisense probe for HLA-A exon 3 codon 105
      variant 1

<400> SEQUENCE: 110
tttttttttc ccgtccgacc tttttttttt                                    30

<210> SEQ ID NO 111
<211> LENGTH: 30
<212> TYPE: DNA
<213> ORGANISM: artificial sequence
<220> FEATURE:
<223> OTHER INFORMATION: antisense probe for HLA-A exon 3 codon 105
      variant 2

<400> SEQUENCE: 111
tttttttttc ccgtccggcc tttttttttt                                    30

<210> SEQ ID NO 112
<211> LENGTH: 30
<212> TYPE: DNA
<213> ORGANISM: artificial sequence
<220> FEATURE:
<223> OTHER INFORMATION: sense probe for HLA-A exon 3 codon 109 variant
      1

<400> SEQUENCE: 112 tttttttcg gcgcttcctc ctttttttttt                                   30

<210> SEQ ID NO 113
<211> LENGTH: 30
<212> TYPE: DNA
<213> ORGANISM: artificial sequence
<220> FEATURE:
<223> OTHER INFORMATION: sense probe for HLA-A exon 3 codon 109 variant
      2

<400> SEQUENCE: 113 tttttttct gcgcctcctc ctttttttttt                                   30

<210> SEQ ID NO 114
<211> LENGTH: 30
<212> TYPE: DNA
<213> ORGANISM: artificial sequence
<220> FEATURE:
<223> OTHER INFORMATION: antisense probe for HLA-A exon 3 codon 109
      variant 1

<400> SEQUENCE: 114
tttttttttg gaggaagcgc ctttttttttt                                  30

<210> SEQ ID NO 115
```

```
<211> LENGTH: 30
<212> TYPE: DNA
<213> ORGANISM: artificial sequence
<220> FEATURE:
<223> OTHER INFORMATION: antisense probe for HLA-A exon 3 codon 109
      variant 2

<400> SEQUENCE: 115
tttttttttt ggaggaggcg cttttttttt                                    30

<210> SEQ ID NO 116
<211> LENGTH: 30
<212> TYPE: DNA
<213> ORGANISM: artificial sequence
<220> FEATURE:
<223> OTHER INFORMATION: sense probe for HLA-A exon 3 codon 114 variant
      2

<400> SEQUENCE: 116 ttttttttg taccggcagg attttttttt                                     30

<210> SEQ ID NO 117
<211> LENGTH: 30
<212> TYPE: DNA
<213> ORGANISM: artificial sequence
<220> FEATURE:
<223> OTHER INFORMATION: sense probe for HLA-A exon 3 codon 114 variant
      3

<400> SEQUENCE: 117 tttttttgt accagcagga cttttttttt                                     30

<210> SEQ ID NO 118
<211> LENGTH: 30
<212> TYPE: DNA
<213> ORGANISM: artificial sequence
<220> FEATURE:
<223> OTHER INFORMATION: antisense probe for HLA-A exon 3 codon 114
      variant 2

<400> SEQUENCE: 118
tttttttttt cctgccggta cttttttttt                                    30

<210> SEQ ID NO 119
<211> LENGTH: 30
<212> TYPE: DNA
<213> ORGANISM: artificial sequence
<220> FEATURE:
<223> OTHER INFORMATION: antisense probe for HLA-A exon 3 codon 114
      variant 3

<400> SEQUENCE: 119 tttttttgt cctgctggta cttttttttt                                     30

<210> SEQ ID NO 120
<211> LENGTH: 30
<212> TYPE: DNA
<213> ORGANISM: artificial sequence
<220> FEATURE:
<223> OTHER INFORMATION: sense probe for HLA-A exon 3 codon 126 variant
      1

<400> SEQUENCE: 120
ttttttttcc ctgaaagagg attttttttt                                    30

<210> SEQ ID NO 121
<211> LENGTH: 30
<212> TYPE: DNA
```

```
<213> ORGANISM: artificial sequence
<220> FEATURE:
<223> OTHER INFORMATION: sense probe for HLA-A exon 3 codon 126 variant
      2

<400> SEQUENCE: 121 ttttttttctg ccctgaacga gttttttttt                                      30

<210> SEQ ID NO 122
<211> LENGTH: 30
<212> TYPE: DNA
<213> ORGANISM: artificial sequence
<220> FEATURE:
<223> OTHER INFORMATION: antisense probe for HLA-A exon 3 codon 126
      variant 1

<400> SEQUENCE: 122
ttttttttcc ctctttcagg gttttttttt                                       30

<210> SEQ ID NO 123
<211> LENGTH: 30
<212> TYPE: DNA
<213> ORGANISM: artificial sequence
<220> FEATURE:
<223> OTHER INFORMATION: antisense probe for HLA-A exon 3 codon 126
      variant 2

<400> SEQUENCE: 123 ttttttttctc tcgttcaggg cttttttttt                                      30

<210> SEQ ID NO 124
<211> LENGTH: 30
<212> TYPE: DNA
<213> ORGANISM: artificial sequence
<220> FEATURE:
<223> OTHER INFORMATION: sense probe for HLA-A exon 3 codon 139 variant
      1

<400> SEQUENCE: 124
ttttttttta tggcggctca gcattttttt                                       30

<210> SEQ ID NO 125
<211> LENGTH: 30
<212> TYPE: DNA
<213> ORGANISM: artificial sequence
<220> FEATURE:
<223> OTHER INFORMATION: sense probe for HLA-A exon 3 codon 139 variant
      2

<400> SEQUENCE: 125
ttttttttca tggcagctca gcattttttt                                       30

<210> SEQ ID NO 126
<211> LENGTH: 30
<212> TYPE: DNA
<213> ORGANISM: artificial sequence
<220> FEATURE:
<223> OTHER INFORMATION: antisense probe for HLA-A exon 3 codon 139
      variant 1

<400> SEQUENCE: 126
ttttttttcc tgagccgcca ttcttttttt                                       30

<210> SEQ ID NO 127
<211> LENGTH: 30
<212> TYPE: DNA
<213> ORGANISM: artificial sequence
<220> FEATURE:
```

<223> OTHER INFORMATION: antisense probe for HLA-A exon 3 codon 139
       variant 2

<400> SEQUENCE: 127 ttttttcct gagctgccat gctttttttt                                    30

<210> SEQ ID NO 128
<211> LENGTH: 30
<212> TYPE: DNA
<213> ORGANISM: artificial sequence
<220> FEATURE:
<223> OTHER INFORMATION: sense probe for HLA-A exon 3 codon 142 variant
       1

<400> SEQUENCE: 128 tttttttct cagatcacca agtttttttt                                    30

<210> SEQ ID NO 129
<211> LENGTH: 30
<212> TYPE: DNA
<213> ORGANISM: artificial sequence
<220> FEATURE:
<223> OTHER INFORMATION: sense probe for HLA-A exon 3 codon 142 variant
       3

<400> SEQUENCE: 129 ttttttttt cagaccacca agtttttttt                                    30

<210> SEQ ID NO 130
<211> LENGTH: 30
<212> TYPE: DNA
<213> ORGANISM: artificial sequence
<220> FEATURE:
<223> OTHER INFORMATION: antisense probe for HLA-A exon 3 codon 142
       variant 1

<400> SEQUENCE: 130 tttttctct tggtgatctg agtatttttt                                    30

<210> SEQ ID NO 131
<211> LENGTH: 30
<212> TYPE: DNA
<213> ORGANISM: artificial sequence
<220> FEATURE:
<223> OTHER INFORMATION: antisense probe for HLA-A exon 3 codon 142
       variant 3

<400> SEQUENCE: 131 ttttttctc ttggtggtct gattttttt                                     30

<210> SEQ ID NO 132
<211> LENGTH: 30
<212> TYPE: DNA
<213> ORGANISM: artificial sequence
<220> FEATURE:
<223> OTHER INFORMATION: sense probe for HLA-A exon 3 codon 145 variant
       1

<400> SEQUENCE: 132
tttttttaaa ccaagcgcaa gttttttttt                                   30

<210> SEQ ID NO 133
<211> LENGTH: 30
<212> TYPE: DNA
<213> ORGANISM: artificial sequence
<220> FEATURE:
<223> OTHER INFORMATION: sense probe for HLA-A exon 3 codon 145 variant
       3

<400> SEQUENCE: 133
tttttttaaa cccagcgcaa gctttttttt                30

<210> SEQ ID NO 134
<211> LENGTH: 30
<212> TYPE: DNA
<213> ORGANISM: artificial sequence
<220> FEATURE:
<223> OTHER INFORMATION: antisense probe for HLA-A exon 3 codon 145
      variant 1

<400> SEQUENCE: 134
ttttttttta cttgcgcttg gttttttttt                30

<210> SEQ ID NO 135
<211> LENGTH: 30
<212> TYPE: DNA
<213> ORGANISM: artificial sequence
<220> FEATURE:
<223> OTHER INFORMATION: antisense probe for HLA-A exon 3 codon 145
      variant 3

<400> SEQUENCE: 135 ttttttttc ttgcgctggg ttttttttt                30

<210> SEQ ID NO 136
<211> LENGTH: 30
<212> TYPE: DNA
<213> ORGANISM: artificial sequence
<220> FEATURE:
<223> OTHER INFORMATION: sense probe for HLA-A exon 3 codon 152 variant
      1

<400> SEQUENCE: 136
tttttttttg cccatgtggc gttttttttt                30

<210> SEQ ID NO 137
<211> LENGTH: 30
<212> TYPE: DNA
<213> ORGANISM: artificial sequence
<220> FEATURE:
<223> OTHER INFORMATION: sense probe for HLA-A exon 3 codon 152 variant
      2

<400> SEQUENCE: 137
tttttttttg cccatgaggc gttttttttt                30

<210> SEQ ID NO 138
<211> LENGTH: 30
<212> TYPE: DNA
<213> ORGANISM: artificial sequence
<220> FEATURE:
<223> OTHER INFORMATION: antisense probe for HLA-A exon 3 codon 152
      variant 1

<400> SEQUENCE: 138
tttttttctc gccacatggg cttttttttt                30

<210> SEQ ID NO 139
<211> LENGTH: 30
<212> TYPE: DNA
<213> ORGANISM: artificial sequence
<220> FEATURE:
<223> OTHER INFORMATION: antisense probe for HLA-A exon 3 codon 152
      variant 2

<400> SEQUENCE: 139 tttttttttct cgcctcatgg gctttttttt                                        30

<210> SEQ ID NO 140
<211> LENGTH: 30
<212> TYPE: DNA
<213> ORGANISM: artificial sequence
<220> FEATURE:
<223> OTHER INFORMATION: sense probe for HLA-A exon 3 codon 152 variant
      1

<400> SEQUENCE: 140
tttttttttc ccatgtggcg gttttttttt                                         30

<210> SEQ ID NO 141
<211> LENGTH: 30
<212> TYPE: DNA
<213> ORGANISM: artificial sequence
<220> FEATURE:
<223> OTHER INFORMATION: sense probe for HLA-A exon 3 codon 152 variant
      2

<400> SEQUENCE: 141
tttttttttc ccatgaggcg gttttttttt                                         30

<210> SEQ ID NO 142
<211> LENGTH: 30
<212> TYPE: DNA
<213> ORGANISM: artificial sequence
<220> FEATURE:
<223> OTHER INFORMATION: antisense probe for HLA-A exon 3 codon 152
      variant 1

<400> SEQUENCE: 142 tttttttcc cgccacatgg gttttttttt                                          30

<210> SEQ ID NO 143
<211> LENGTH: 30
<212> TYPE: DNA
<213> ORGANISM: artificial sequence
<220> FEATURE:
<223> OTHER INFORMATION: antisense probe for HLA-A exon 3 codon 152
      variant 3

<400> SEQUENCE: 143 tttttttcc cgcctcatgg gttttttttt                                          30

<210> SEQ ID NO 144
<211> LENGTH: 30
<212> TYPE: DNA
<213> ORGANISM: artificial sequence
<220> FEATURE:
<223> OTHER INFORMATION: sense probe for HLA-A exon 3 codon 156 variant
      2

<400> SEQUENCE: 144 tttttttag cagcagagag ctctttttttt                                         30

<210> SEQ ID NO 145
<211> LENGTH: 30
<212> TYPE: DNA
<213> ORGANISM: artificial sequence
<220> FEATURE:
<223> OTHER INFORMATION: sense probe for HLA-A exon 3 codon 156 variant
      3

<400> SEQUENCE: 145 tttttttag cagtggagag ctctttttttt                                         30

```
<210> SEQ ID NO 146
<211> LENGTH: 30
<212> TYPE: DNA
<213> ORGANISM: artificial sequence
<220> FEATURE:
<223> OTHER INFORMATION: antisense probe for HLA-A exon 3 codon 156
      variant 2

<400> SEQUENCE: 146 ttttttttg ctctctgctg cttttttttt                                      30

<210> SEQ ID NO 147
<211> LENGTH: 30
<212> TYPE: DNA
<213> ORGANISM: artificial sequence
<220> FEATURE:
<223> OTHER INFORMATION: antisense probe for HLA-A exon 3 codon 156
      variant 3

<400> SEQUENCE: 147 ttttttttg ctctccactg cttttttttt                                      30

<210> SEQ ID NO 148
<211> LENGTH: 30
<212> TYPE: DNA
<213> ORGANISM: artificial sequence
<220> FEATURE:
<223> OTHER INFORMATION: sense probe for HLA-A exon 3 codon 163 variant
      1

<400> SEQUENCE: 148 tttttttta gggcacgtgc gctttttttt                                      30

<210> SEQ ID NO 149
<211> LENGTH: 30
<212> TYPE: DNA
<213> ORGANISM: artificial sequence
<220> FEATURE:
<223> OTHER INFORMATION: sense probe for HLA-A exon 3 codon 163 variant
      2

<400> SEQUENCE: 149 tttttttta gggccggtgc tctttttttt                                      30

<210> SEQ ID NO 150
<211> LENGTH: 30
<212> TYPE: DNA
<213> ORGANISM: artificial sequence
<220> FEATURE:
<223> OTHER INFORMATION: antisense probe for HLA-A exon 3 codon 163
      variant 1

<400> SEQUENCE: 150 ttttttttc gcacgtgccc tttttttttt                                      30

<210> SEQ ID NO 151
<211> LENGTH: 30
<212> TYPE: DNA
<213> ORGANISM: artificial sequence
<220> FEATURE:
<223> OTHER INFORMATION: antisense probe for HLA-A exon 3 codon 163
      variant 2

<400> SEQUENCE: 151 ttttttttg caccggccct tttttttttt                                      30
```

-continued

<210> SEQ ID NO 152
<211> LENGTH: 30
<212> TYPE: DNA
<213> ORGANISM: artificial sequence
<220> FEATURE:
<223> OTHER INFORMATION: sense probe for HLA-A exon 3 codon 166 variant
      1

<400> SEQUENCE: 152
tttttttttg tggagtggct cttttttttt                                        30

<210> SEQ ID NO 153
<211> LENGTH: 30
<212> TYPE: DNA
<213> ORGANISM: artificial sequence
<220> FEATURE:
<223> OTHER INFORMATION: sense probe for HLA-A exon 3 codon 166 variant
      2

<400> SEQUENCE: 153
tttttttttg tggacgggct cttttttttt                                        30

<210> SEQ ID NO 154
<211> LENGTH: 30
<212> TYPE: DNA
<213> ORGANISM: artificial sequence
<220> FEATURE:
<223> OTHER INFORMATION: antisense probe for HLA-A exon 3 codon 166
      variant 1

<400> SEQUENCE: 154
tttttttttg agccactcca cttttttttt                                        30

<210> SEQ ID NO 155
<211> LENGTH: 30
<212> TYPE: DNA
<213> ORGANISM: artificial sequence
<220> FEATURE:
<223> OTHER INFORMATION: antisense probe for HLA-A exon 3 codon 166
      variant 2

<400> SEQUENCE: 155
tttttttttg agcccgtcca cttttttttt                                        30

<210> SEQ ID NO 156
<211> LENGTH: 30
<212> TYPE: DNA
<213> ORGANISM: artificial sequence
<220> FEATURE:
<223> OTHER INFORMATION: antisense probe for HLA-B exon 2 codon 9
      variant 1

<400> SEQUENCE: 156
ttttttttgg tgtagaaata ctcttttttt                                        30

<210> SEQ ID NO 157
<211> LENGTH: 30
<212> TYPE: DNA
<213> ORGANISM: artificial sequence
<220> FEATURE:
<223> OTHER INFORMATION: antisense probe for HLA-B exon 2 codon 9
      variant 2

<400> SEQUENCE: 157
tttttttttg tgtggaaata ctcttttttt                                        30

<210> SEQ ID NO 158
<211> LENGTH: 30

```
<212> TYPE: DNA
<213> ORGANISM: artificial sequence
<220> FEATURE:
<223> OTHER INFORMATION: antisense probe for HLA-B exon 2 codon 9
      variant 3

<400> SEQUENCE: 158 ttttttttttg tgtcgaaata ctcttttttt                                          30

<210> SEQ ID NO 159
<211> LENGTH: 30
<212> TYPE: DNA
<213> ORGANISM: artificial sequence
<220> FEATURE:
<223> OTHER INFORMATION: sense probe for HLA-B exon 2 codon 11 variant 1

<400> SEQUENCE: 159 ttttttttatc accgccatgt ctttttttt                                           30

<210> SEQ ID NO 160
<211> LENGTH: 30
<212> TYPE: DNA
<213> ORGANISM: artificial sequence
<220> FEATURE:
<223> OTHER INFORMATION: sense probe for HLA-B exon 2 codon 11 variant 2

<400> SEQUENCE: 160 ttttttttatc acctccgtgt ctttttttt                                           30

<210> SEQ ID NO 161
<211> LENGTH: 30
<212> TYPE: DNA
<213> ORGANISM: artificial sequence
<220> FEATURE:
<223> OTHER INFORMATION: sense probe for HLA-B exon 2 codon 11 variant 3

<400> SEQUENCE: 161 ttttttttatc accgccgtgt ctttttttt                                           30

<210> SEQ ID NO 162
<211> LENGTH: 30
<212> TYPE: DNA
<213> ORGANISM: artificial sequence
<220> FEATURE:
<223> OTHER INFORMATION: antisense probe for HLA-B exon 2 codon 11
      variant 1

<400> SEQUENCE: 162 ttttttttttg acatggcggt gcttttttt                                           30

<210> SEQ ID NO 163
<211> LENGTH: 30
<212> TYPE: DNA
<213> ORGANISM: artificial sequence
<220> FEATURE:
<223> OTHER INFORMATION: antisense probe for HLA-B exon 2 codon 11
      variant 2

<400> SEQUENCE: 163 ttttttttttg acacggaggt gcttttttt                                           30

<210> SEQ ID NO 164
<211> LENGTH: 30
<212> TYPE: DNA
<213> ORGANISM: artificial sequence
<220> FEATURE:
<223> OTHER INFORMATION: antisense probe for HLA-B exon 2 codon 11
      variant 3
```

```
<400> SEQUENCE: 164
tttttttttg acacggcggt gctttttttt                                    30

<210> SEQ ID NO 165
<211> LENGTH: 30
<212> TYPE: DNA
<213> ORGANISM: artificial sequence
<220> FEATURE:
<223> OTHER INFORMATION: antisense probe for HLA-B exon 2 codon 24
      variant 1

<400> SEQUENCE: 165
tttttttttc actgcgatga agtttttttt                                    30

<210> SEQ ID NO 166
<211> LENGTH: 30
<212> TYPE: DNA
<213> ORGANISM: artificial sequence
<220> FEATURE:
<223> OTHER INFORMATION: antisense probe for HLA-B exon 2 codon 24
      variant 2

<400> SEQUENCE: 166
ttttttttcc actgagatga agtttttttt                                    30

<210> SEQ ID NO 167
<211> LENGTH: 30
<212> TYPE: DNA
<213> ORGANISM: artificial sequence
<220> FEATURE:
<223> OTHER INFORMATION: antisense probe for HLA-B exon 2 codon 24
      variant 3

<400> SEQUENCE: 167
tttttttttc acggtgatga agtttttttt                                    30

<210> SEQ ID NO 168
<211> LENGTH: 30
<212> TYPE: DNA
<213> ORGANISM: artificial sequence
<220> FEATURE:
<223> OTHER INFORMATION: sense probe for HLA-B exon 2 codon 24 variant 4

<400> SEQUENCE: 168
ttttttttcc actgcaatga agtttttttt                                    30

<210> SEQ ID NO 169
<211> LENGTH: 30
<212> TYPE: DNA
<213> ORGANISM: artificial sequence
<220> FEATURE:
<223> OTHER INFORMATION: sense probe for HLA-B exon 2 codon 31 variant 1

<400> SEQUENCE: 169
ttttttttcg acacccagtt ctctttttttt                                   30

<210> SEQ ID NO 170
<211> LENGTH: 30
<212> TYPE: DNA
<213> ORGANISM: artificial sequence
<220> FEATURE:
<223> OTHER INFORMATION: sense probe for HLA-B exon 2 codon 31 variant 2

<400> SEQUENCE: 170
ttttttttcg acacgctgtt ctctttttttt                                   30
```

```
<210> SEQ ID NO 171
<211> LENGTH: 30
<212> TYPE: DNA
<213> ORGANISM: artificial sequence
<220> FEATURE:
<223> OTHER INFORMATION: sense probe for HLA-B exon 2 codon 31 variant 3

<400> SEQUENCE: 171
ttttttttcg acacgcagtt ctcttttttt                                        30

<210> SEQ ID NO 172
<211> LENGTH: 30
<212> TYPE: DNA
<213> ORGANISM: artificial sequence
<220> FEATURE:
<223> OTHER INFORMATION: sense probe for HLA-B exon 2 codon 31 variant 4

<400> SEQUENCE: 172 ttttttttctg acggcaccca gccttttttt                                       30

<210> SEQ ID NO 173
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 1

<400> SEQUENCE: 173 ttttttttcta cgaactgggt gttttttttt                                       30

<210> SEQ ID NO 174
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 2

<400> SEQUENCE: 174 ttttttttcta cgaacagcgt gttttttttt                                       30

<210> SEQ ID NO 175
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 3

<400> SEQUENCE: 175 ttttttttcta cgaactgcgt gttttttttt                                       30

<210> SEQ ID NO 176
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 4

<400> SEQUENCE: 176 ttttttttttc tgggtgccgt ctttttttttt                                      30

<210> SEQ ID NO 177
<211> LENGTH: 30
<212> TYPE: DNA
```

-continued

```
<213> ORGANISM: artificial sequence
<220> FEATURE:
<223> OTHER INFORMATION: antisense probe for HLA-B exon 2 codon 31
      variant 1

<400> SEQUENCE: 177
tttttttcta cgaactgggt gcttttttt                                        30

<210> SEQ ID NO 178
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 2

<400> SEQUENCE: 178 tttttttctac gaacagcgtg tctctttttt                                      30

<210> SEQ ID NO 179
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 3

<400> SEQUENCE: 179 tttttttctac gaactgcgtg tctctttttt                                      30

<210> SEQ ID NO 180
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 1

<400> SEQUENCE: 180 ttttttttc gaactgggtg ttttttttt                                         30

<210> SEQ ID NO 181
<211> LENGTH: 30
<212> TYPE: DNA
<213> ORGANISM: artificial sequence
<220> FEATURE:
<223> OTHER INFORMATION: antisense probe for HLA-B exon 2 codon 31
      variant 2

<400> SEQUENCE: 181
ttttttttga actgcgtgtc gtttttttt                                        30

<210> SEQ ID NO 182
<211> LENGTH: 30
<212> TYPE: DNA
<213> ORGANISM: artificial sequence
<220> FEATURE:
<223> OTHER INFORMATION: sense probe for HLA-B exon 2 codon 35 variant 1

<400> SEQUENCE: 182 ttttttctt tcgtgaggtt cgttttttt                                         30

<210> SEQ ID NO 183
<211> LENGTH: 30
<212> TYPE: DNA
<213> ORGANISM: artificial sequence
<220> FEATURE:
<223> OTHER INFORMATION: sense probe for HLA-B exon 2 codon 35 variant 2
```

```
<400> SEQUENCE: 183
tttttttttt tcgtgcggtt cgttttttt                                    30

<210> SEQ ID NO 184
<211> LENGTH: 30
<212> TYPE: DNA
<213> ORGANISM: artificial sequence
<220> FEATURE:
<223> OTHER INFORMATION: sense probe for HLA-B exon 2 codon 35 variant 2

<400> SEQUENCE: 184
tttttttttg ttcgtgcggt tcttttttt                                    30

<210> SEQ ID NO 185
<211> LENGTH: 30
<212> TYPE: DNA
<213> ORGANISM: artificial sequence
<220> FEATURE:
<223> OTHER INFORMATION: sense probe for HLA-B exon 2 codon 41 variant 1

<400> SEQUENCE: 185 tttttttta cgccgcgagt cttttttt                                      30

<210> SEQ ID NO 186
<211> LENGTH: 30
<212> TYPE: DNA
<213> ORGANISM: artificial sequence
<220> FEATURE:
<223> OTHER INFORMATION: sense probe for HLA-B exon 2 codon 41 variant 2

<400> SEQUENCE: 186 tttttttta cgccacgagt cttttttt                                      30

<210> SEQ ID NO 187
<211> LENGTH: 30
<212> TYPE: DNA
<213> ORGANISM: artificial sequence
<220> FEATURE:
<223> OTHER INFORMATION: sense probe for HLA-B exon 2 codon 41 variant 1

<400> SEQUENCE: 187
tttttttttt cgccgcgagt cttttttt                                     30

<210> SEQ ID NO 188
<211> LENGTH: 30
<212> TYPE: DNA
<213> ORGANISM: artificial sequence
<220> FEATURE:
<223> OTHER INFORMATION: antisense probe for HLA-B exon 2 codon 45
      variant 1

<400> SEQUENCE: 188
tttttttttg ctcctctctc ggttttttt                                    30

<210> SEQ ID NO 189
<211> LENGTH: 30
<212> TYPE: DNA
<213> ORGANISM: artificial sequence
<220> FEATURE:
<223> OTHER INFORMATION: antisense probe for HLA-B exon 2 codon 45
      variant 2

<400> SEQUENCE: 189
tttttttttg ctccgtcctc ggttttttt                                    30
```

```
<210> SEQ ID NO 190
<211> LENGTH: 30
<212> TYPE: DNA
<213> ORGANISM: artificial sequence
<220> FEATURE:
<223> OTHER INFORMATION: antisense probe for HLA-B exon 2 codon 45
      variant 3

<400> SEQUENCE: 190 ttttttttg ctccttcctc ggtttttttt                                    30

<210> SEQ ID NO 191
<211> LENGTH: 30
<212> TYPE: DNA
<213> ORGANISM: artificial sequence
<220> FEATURE:
<223> OTHER INFORMATION: antisense probe for HLA-B exon 2 codon 45
      variant 4

<400> SEQUENCE: 191 ttttttttg cgccatcctc ggtttttttt                                    30

<210> SEQ ID NO 192
<211> LENGTH: 30
<212> TYPE: DNA
<213> ORGANISM: artificial sequence
<220> FEATURE:
<223> OTHER INFORMATION: antisense probe for HLA-B exon 2 codon 45
      variant 5

<400> SEQUENCE: 192 ttttttttg ctcccctctc ggtttttttt                                    30

<210> SEQ ID NO 193
<211> LENGTH: 30
<212> TYPE: DNA
<213> ORGANISM: artificial sequence
<220> FEATURE:
<223> OTHER INFORMATION: sense probe for HLA-B exon 2 codon 50 variant 1

<400> SEQUENCE: 193
ttttttttgc gccatggata gtttttttt                                    30

<210> SEQ ID NO 194
<211> LENGTH: 30
<212> TYPE: DNA
<213> ORGANISM: artificial sequence
<220> FEATURE:
<223> OTHER INFORMATION: sense probe for HLA-B exon 2 codon 50 variant 2

<400> SEQUENCE: 194
tttttttttc gccgtggata tttttttttt                                   30

<210> SEQ ID NO 195
<211> LENGTH: 30
<212> TYPE: DNA
<213> ORGANISM: artificial sequence
<220> FEATURE:
<223> OTHER INFORMATION: sense probe for HLA-B exon 2 codon 50 variant 3

<400> SEQUENCE: 195
tttttttttt gccgtgggtg tttttttttt                                   30

<210> SEQ ID NO 196
<211> LENGTH: 30
<212> TYPE: DNA
<213> ORGANISM: artificial sequence
<220> FEATURE:
```

```
<223> OTHER INFORMATION: sense probe for HLA-B exon 2 codon 50 variant 3

<400> SEQUENCE: 196
tttttttttc cgtgggtgga tttttttttt                                30

<210> SEQ ID NO 197
<211> LENGTH: 30
<212> TYPE: DNA
<213> ORGANISM: artificial sequence
<220> FEATURE:
<223> OTHER INFORMATION: antisense probe for HLA-B exon 2 codon 50
      variant 2

<400> SEQUENCE: 197 tttttttctct ctatccacgg cgcttttttt                               30

<210> SEQ ID NO 198
<211> LENGTH: 30
<212> TYPE: DNA
<213> ORGANISM: artificial sequence
<220> FEATURE:
<223> OTHER INFORMATION: antisense probe for HLA-B exon 2 codon 54
      variant 1

<400> SEQUENCE: 198 tttttttttcc tcctgctcca ccttttttttt                              30

<210> SEQ ID NO 199
<211> LENGTH: 30
<212> TYPE: DNA
<213> ORGANISM: artificial sequence
<220> FEATURE:
<223> OTHER INFORMATION: antisense probe for HLA-B exon 2 codon 54
      variant 2

<400> SEQUENCE: 199 tttttttttcc tcctgctcta tcttttttttt                              30

<210> SEQ ID NO 200
<211> LENGTH: 30
<212> TYPE: DNA
<213> ORGANISM: artificial sequence
<220> FEATURE:
<223> OTHER INFORMATION: antisense probe for HLA-B exon 2 codon 54
      variant 3

<400> SEQUENCE: 200 tttttttttcc ctcttgctct atcttttttt                               30

<210> SEQ ID NO 201
<211> LENGTH: 30
<212> TYPE: DNA
<213> ORGANISM: artificial sequence
<220> FEATURE:
<223> OTHER INFORMATION: sense probe for HLA-B exon 2 codon 58 variant 1

<400> SEQUENCE: 201
tttttttttc ggagtattgg gatttttttt                                30

<210> SEQ ID NO 202
<211> LENGTH: 30
<212> TYPE: DNA
<213> ORGANISM: artificial sequence
<220> FEATURE:
<223> OTHER INFORMATION: sense probe for HLA-B exon 2 codon 58 variant 2

<400> SEQUENCE: 202
```

-continued

```
tttttttcc ggaatattgg gatttttttt                              30
```

<210> SEQ ID NO 203
<211> LENGTH: 30
<212> TYPE: DNA
<213> ORGANISM: artificial sequence
<220> FEATURE:
<223> OTHER INFORMATION: antisense probe for HLA-B exon 2 codon 63
      variant 1

<400> SEQUENCE: 203

```
ttttttttccc tgtgtgttcc gtctttttt                             30
```

<210> SEQ ID NO 204
<211> LENGTH: 30
<212> TYPE: DNA
<213> ORGANISM: artificial sequence
<220> FEATURE:
<223> OTHER INFORMATION: antisense probe for HLA-B exon 2 codon 63
      variant 2

<400> SEQUENCE: 204

```
ttttttttccc tgtgtctccc gtctttttt                             30
```

<210> SEQ ID NO 205
<211> LENGTH: 30
<212> TYPE: DNA
<213> ORGANISM: artificial sequence
<220> FEATURE:
<223> OTHER INFORMATION: antisense probe for HLA-B exon 2 codon 63
      variant 3

<400> SEQUENCE: 205

```
ttttttttccc cgtgtctccc gtctttttt                             30
```

<210> SEQ ID NO 206
<211> LENGTH: 30
<212> TYPE: DNA
<213> ORGANISM: artificial sequence
<220> FEATURE:
<223> OTHER INFORMATION: antisense probe for HLA-B exon 2 codon 63
      variant 4

<400> SEQUENCE: 206

```
ttttttttccc cgtgtctccc ctctttttt                             30
```

<210> SEQ ID NO 207
<211> LENGTH: 30
<212> TYPE: DNA
<213> ORGANISM: artificial sequence
<220> FEATURE:
<223> OTHER INFORMATION: sense probe for HLA-B exon 2 codon 67 variant 1

<400> SEQUENCE: 207

```
tttttttttca gatctccaag acttttttt                             30
```

<210> SEQ ID NO 208
<211> LENGTH: 30
<212> TYPE: DNA
<213> ORGANISM: artificial sequence
<220> FEATURE:
<223> OTHER INFORMATION: sense probe for HLA-B exon 2 codon 67 variant 2

<400> SEQUENCE: 208

```
tttttttttca gatcttcaag acttttttt                             30
```

<210> SEQ ID NO 209

```
<211> LENGTH: 30
<212> TYPE: DNA
<213> ORGANISM: artificial sequence
<220> FEATURE:
<223> OTHER INFORMATION: sense probe for HLA-B exon 2 codon 67 variant 3

<400> SEQUENCE: 209 tttttttttca gatctacaag gctttttttt                                    30

<210> SEQ ID NO 210
<211> LENGTH: 30
<212> TYPE: DNA
<213> ORGANISM: artificial sequence
<220> FEATURE:
<223> OTHER INFORMATION: sense probe for HLA-B exon 2 codon 67 variant 4

<400> SEQUENCE: 210 tttttttttca gatctgcaag actttttttt                                    30

<210> SEQ ID NO 211
<211> LENGTH: 30
<212> TYPE: DNA
<213> ORGANISM: artificial sequence
<220> FEATURE:
<223> OTHER INFORMATION: sense probe for HLA-B exon 2 codon 67 variant 5

<400> SEQUENCE: 211 tttttttttag atctgcaagg cttttttttt                                    30

<210> SEQ ID NO 212
<211> LENGTH: 30
<212> TYPE: DNA
<213> ORGANISM: artificial sequence
<220> FEATURE:
<223> OTHER INFORMATION: sense probe for HLA-B exon 2 codon 67 variant 6

<400> SEQUENCE: 212 tttttttttcg aacatgaag gttttttttt                                     30

<210> SEQ ID NO 213
<211> LENGTH: 30
<212> TYPE: DNA
<213> ORGANISM: artificial sequence
<220> FEATURE:
<223> OTHER INFORMATION: sense probe for HLA-B exon 2 codon 67 variant 7

<400> SEQUENCE: 213 tttttttttca gaagtacaag cgcttttttt                                    30

<210> SEQ ID NO 214
<211> LENGTH: 30
<212> TYPE: DNA
<213> ORGANISM: artificial sequence
<220> FEATURE:
<223> OTHER INFORMATION: sense probe for HLA-B exon 2 codon 67 variant 8

<400> SEQUENCE: 214 tttttttttca gatctagaag actttttttt                                    30

<210> SEQ ID NO 215
<211> LENGTH: 30
<212> TYPE: DNA
<213> ORGANISM: artificial sequence
<220> FEATURE:
<223> OTHER INFORMATION: sense probe for HLA-B exon 2 codon 67 variant 6

<400> SEQUENCE: 215
```

```
tttttttttac ggaacatgaa gttttttttt                                          30

<210> SEQ ID NO 216
<211> LENGTH: 30
<212> TYPE: DNA
<213> ORGANISM: artificial sequence
<220> FEATURE:
<223> OTHER INFORMATION: sense probe for HLA-B exon 2 codon 67 variant 7

<400> SEQUENCE: 216 tttttttttca gaagtacaag cgttttttttt                                         30

<210> SEQ ID NO 217
<211> LENGTH: 30
<212> TYPE: DNA
<213> ORGANISM: artificial sequence
<220> FEATURE:
<223> OTHER INFORMATION: sense probe for HLA-B exon 2 codon 67 variant 8

<400> SEQUENCE: 217
ttttttttag atctacaaga ccttttttttt                                          30

<210> SEQ ID NO 218
<211> LENGTH: 30
<212> TYPE: DNA
<213> ORGANISM: artificial sequence
<220> FEATURE:
<223> OTHER INFORMATION: sense probe for HLA-B exon 2 codon 69 variant 1

<400> SEQUENCE: 218 tttttttta agaccaacac attttttttt                                            30

<210> SEQ ID NO 219
<211> LENGTH: 30
<212> TYPE: DNA
<213> ORGANISM: artificial sequence
<220> FEATURE:
<223> OTHER INFORMATION: sense probe for HLA-B exon 2 codon 69 variant 2

<400> SEQUENCE: 219 tttttttta aggcccaggc acttttttttt                                           30

<210> SEQ ID NO 220
<211> LENGTH: 30
<212> TYPE: DNA
<213> ORGANISM: artificial sequence
<220> FEATURE:
<223> OTHER INFORMATION: sense probe for HLA-B exon 2 codon 69 variant 3

<400> SEQUENCE: 220 tttttttta aggccaaggc acttttttttt                                           30

<210> SEQ ID NO 221
<211> LENGTH: 30
<212> TYPE: DNA
<213> ORGANISM: artificial sequence
<220> FEATURE:
<223> OTHER INFORMATION: sense probe for HLA-B exon 2 codon 69 variant 4

<400> SEQUENCE: 221 tttttttta aggcctccgc gcttttttttt                                           30

<210> SEQ ID NO 222
<211> LENGTH: 30
<212> TYPE: DNA
<213> ORGANISM: artificial sequence
<220> FEATURE:
```

<223> OTHER INFORMATION: sense probe for HLA-B exon 2 codon 69 variant 5

<400> SEQUENCE: 222 tttttttttta agcgccaggc acttttttttt                                    30

<210> SEQ ID NO 223
<211> LENGTH: 30
<212> TYPE: DNA
<213> ORGANISM: artificial sequence
<220> FEATURE:
<223> OTHER INFORMATION: sense probe for HLA-B exon 2 codon 69 variant 1

<400> SEQUENCE: 223 tttttttttta gaccaacaca ctttttttttt                                    30

<210> SEQ ID NO 224
<211> LENGTH: 30
<212> TYPE: DNA
<213> ORGANISM: artificial sequence
<220> FEATURE:
<223> OTHER INFORMATION: sense probe for HLA-B exon 2 codon 69 variant 2

<400> SEQUENCE: 224 tttttttttaa ggcccaggca cattttttttt                                    30

<210> SEQ ID NO 225
<211> LENGTH: 30
<212> TYPE: DNA
<213> ORGANISM: artificial sequence
<220> FEATURE:
<223> OTHER INFORMATION: sense probe for HLA-B exon 2 codon 69 variant 3

<400> SEQUENCE: 225 tttttttttaa ggccaaggca cattttttttt                                    30

<210> SEQ ID NO 226
<211> LENGTH: 30
<212> TYPE: DNA
<213> ORGANISM: artificial sequence
<220> FEATURE:
<223> OTHER INFORMATION: sense probe for HLA-B exon 2 codon 69 variant 4

<400> SEQUENCE: 226
ttttttttga aggcctccgc gctttttttt                                      30

<210> SEQ ID NO 227
<211> LENGTH: 30
<212> TYPE: DNA
<213> ORGANISM: artificial sequence
<220> FEATURE:
<223> OTHER INFORMATION: sense probe for HLA-B exon 2 codon 69 variant 5

<400> SEQUENCE: 227
ttttttttca agcgccaggc atttttttttt                                     30

<210> SEQ ID NO 228
<211> LENGTH: 30
<212> TYPE: DNA
<213> ORGANISM: artificial sequence
<220> FEATURE:
<223> OTHER INFORMATION: sense probe for HLA-B exon 2 codon 69 variant 4

<400> SEQUENCE: 228 ttttttttcga aggcctccgc gctttttttt                                     30

<210> SEQ ID NO 229

```
<211> LENGTH: 30
<212> TYPE: DNA
<213> ORGANISM: artificial sequence
<220> FEATURE:
<223> OTHER INFORMATION: sense probe for HLA-B exon 2 codon 74 variant 1

<400> SEQUENCE: 229
ttttttttca gacttaccga gctttttttt                                              30

<210> SEQ ID NO 230
<211> LENGTH: 30
<212> TYPE: DNA
<213> ORGANISM: artificial sequence
<220> FEATURE:
<223> OTHER INFORMATION: sense probe for HLA-B exon 2 codon 74 variant 2

<400> SEQUENCE: 230 tttttttac agactgaccg atctttttttt                                              30

<210> SEQ ID NO 231
<211> LENGTH: 30
<212> TYPE: DNA
<213> ORGANISM: artificial sequence
<220> FEATURE:
<223> OTHER INFORMATION: sense probe for HLA-B exon 2 codon 77 variant 1

<400> SEQUENCE: 231
ttttttttgc aggctctctc gtctttttttt                                             30

<210> SEQ ID NO 232
<211> LENGTH: 30
<212> TYPE: DNA
<213> ORGANISM: artificial sequence
<220> FEATURE:
<223> OTHER INFORMATION: sense probe for HLA-B exon 2 codon 77 variant 2

<400> SEQUENCE: 232
ttttttttgc aggttctctc gtctttttttt                                             30

<210> SEQ ID NO 233
<211> LENGTH: 30
<212> TYPE: DNA
<213> ORGANISM: artificial sequence
<220> FEATURE:
<223> OTHER INFORMATION: sense probe for HLA-B exon 2 codon 77 variant 1

<400> SEQUENCE: 233
ttttttttgc aggtcctctc gtctttttttt                                             30

<210> SEQ ID NO 234
<211> LENGTH: 30
<212> TYPE: DNA
<213> ORGANISM: artificial sequence
<220> FEATURE:
<223> OTHER INFORMATION: sense probe for HLA-B exon 2 codon 77 variant 2

<400> SEQUENCE: 234
ttttttttgc aggctcactc gtctttttttt                                             30

<210> SEQ ID NO 235
<211> LENGTH: 30
<212> TYPE: DNA
<213> ORGANISM: artificial sequence
<220> FEATURE:
<223> OTHER INFORMATION: sense probe for HLA-B exon 2 codon 77 variant 3

<400> SEQUENCE: 235
```

```
tttttttttgc aggcccactc gtcttttttt                                     30
```

<210> SEQ ID NO 236
<211> LENGTH: 30
<212> TYPE: DNA
<213> ORGANISM: artificial sequence
<220> FEATURE:
<223> OTHER INFORMATION: sense probe for HLA-B exon 2 codon 81 variant 1

<400> SEQUENCE: 236

```
ttttttttttg gaacctgcgc gttttttttt                                     30
```

<210> SEQ ID NO 237
<211> LENGTH: 30
<212> TYPE: DNA
<213> ORGANISM: artificial sequence
<220> FEATURE:
<223> OTHER INFORMATION: sense probe for HLA-B exon 2 codon 81 variant 2

<400> SEQUENCE: 237

```
tttttttctcg gatcgcgctc cgtcttttttt                                    30
```

<210> SEQ ID NO 238
<211> LENGTH: 30
<212> TYPE: DNA
<213> ORGANISM: artificial sequence
<220> FEATURE:
<223> OTHER INFORMATION: sense probe for HLA-B exon 2 codon 81 variant 3

<400> SEQUENCE: 238

```
tttttttttgc accgcgctcc gtcttttttt                                     30
```

<210> SEQ ID NO 239
<211> LENGTH: 30
<212> TYPE: DNA
<213> ORGANISM: artificial sequence
<220> FEATURE:
<223> OTHER INFORMATION: sense probe for HLA-B exon 2 codon 81 variant 4

<400> SEQUENCE: 239

```
tttttttctcg gaccctgctc cgtcttttttt                                    30
```

<210> SEQ ID NO 240
<211> LENGTH: 30
<212> TYPE: DNA
<213> ORGANISM: artificial sequence
<220> FEATURE:
<223> OTHER INFORMATION: sense probe for HLA-B exon 3 codon 94 variant 1

<400> SEQUENCE: 240

```
tttttttttcc tcacaccctc cttttttttt                                     30
```

<210> SEQ ID NO 241
<211> LENGTH: 30
<212> TYPE: DNA
<213> ORGANISM: artificial sequence
<220> FEATURE:
<223> OTHER INFORMATION: sense probe for HLA-B exon 3 codon 94 variant 2

<400> SEQUENCE: 241

```
ttttttttttc tcacatcatc catttttttt                                     30
```

<210> SEQ ID NO 242
<211> LENGTH: 30
<212> TYPE: DNA
<213> ORGANISM: artificial sequence
<220> FEATURE:

```
<223> OTHER INFORMATION: antisense probe for HLA-B exon 3 codon 94
      variant 1

<400> SEQUENCE: 242
ttttttttcg gagggtgtga gttttttttt                                        30

<210> SEQ ID NO 243
<211> LENGTH: 30
<212> TYPE: DNA
<213> ORGANISM: artificial sequence
<220> FEATURE:
<223> OTHER INFORMATION: antisense probe for HLA-B exon 3 codon 94
      variant 2

<400> SEQUENCE: 243
tttttttttg gatgatgtga gatttttttt                                        30

<210> SEQ ID NO 244
<211> LENGTH: 30
<212> TYPE: DNA
<213> ORGANISM: artificial sequence
<220> FEATURE:
<223> OTHER INFORMATION: sense probe for HLA-B exon 3 codon 97/99
      variant 1

<400> SEQUENCE: 244 tttttttag aggatgtacg gtctttttttt                                        30

<210> SEQ ID NO 245
<211> LENGTH: 30
<212> TYPE: DNA
<213> ORGANISM: artificial sequence
<220> FEATURE:
<223> OTHER INFORMATION: sense probe for HLA-B exon 3 codon 97/99
      variant 2

<400> SEQUENCE: 245 tttttttag agcatgtacg gtctttttttt                                        30

<210> SEQ ID NO 246
<211> LENGTH: 30
<212> TYPE: DNA
<213> ORGANISM: artificial sequence
<220> FEATURE:
<223> OTHER INFORMATION: antisense probe for HLA-B exon 3 codon 97/99
      variant 1

<400> SEQUENCE: 246 ttttttttc cgtacatcct ctttttttt                                          30

<210> SEQ ID NO 247
<211> LENGTH: 30
<212> TYPE: DNA
<213> ORGANISM: artificial sequence
<220> FEATURE:
<223> OTHER INFORMATION: antisense probe for HLA-B exon 3 codon 97/99
      variant 2

<400> SEQUENCE: 247 ttttttttc cgtacatgct ctttttttt                                          30

<210> SEQ ID NO 248
<211> LENGTH: 30
<212> TYPE: DNA
<213> ORGANISM: artificial sequence
<220> FEATURE:
<223> OTHER INFORMATION: sense probe for HLA-B exon 3 codon 103 variant
      1
```

```
<400> SEQUENCE: 248
ttttttttta cgtggggccg ttttttttttt                                30

<210> SEQ ID NO 249
<211> LENGTH: 30
<212> TYPE: DNA
<213> ORGANISM: artificial sequence
<220> FEATURE:
<223> OTHER INFORMATION: sense probe for HLA-B exon 3 codon 103 variant
      3

<400> SEQUENCE: 249
ttttttttta cctggggccg ttttttttttt                                30

<210> SEQ ID NO 250
<211> LENGTH: 30
<212> TYPE: DNA
<213> ORGANISM: artificial sequence
<220> FEATURE:
<223> OTHER INFORMATION: antisense probe for HLA-B exon 3 codon 103
      variant 1

<400> SEQUENCE: 250
ttttttttct cggccccacg ttttttttttt                                30

<210> SEQ ID NO 251
<211> LENGTH: 30
<212> TYPE: DNA
<213> ORGANISM: artificial sequence
<220> FEATURE:
<223> OTHER INFORMATION: antisense probe for HLA-B exon 3 codon 103
      variant 3

<400> SEQUENCE: 251
ttttttttct cggccccagg ttttttttttt                                30

<210> SEQ ID NO 252
<211> LENGTH: 30
<212> TYPE: DNA
<213> ORGANISM: artificial sequence
<220> FEATURE:
<223> OTHER INFORMATION: sense probe for HLA-B exon 3 codon 114 variant
      1

<400> SEQUENCE: 252
ttttttttgg gcataaccag tctttttttt                                 30

<210> SEQ ID NO 253
<211> LENGTH: 30
<212> TYPE: DNA
<213> ORGANISM: artificial sequence
<220> FEATURE:
<223> OTHER INFORMATION: sense probe for HLA-B exon 3 codon 114 variant
      2

<400> SEQUENCE: 253 ttttttttttg ggcatgacca gctttttttt                                30

<210> SEQ ID NO 254
<211> LENGTH: 30
<212> TYPE: DNA
<213> ORGANISM: artificial sequence
<220> FEATURE:
<223> OTHER INFORMATION: antisense probe for HLA-B exon 3 codon 114
      variant 1

<400> SEQUENCE: 254
```

```
tttttttcca ctggttatgc ccttttttttt                                30
```

<210> SEQ ID NO 255
<211> LENGTH: 30
<212> TYPE: DNA
<213> ORGANISM: artificial sequence
<220> FEATURE:
<223> OTHER INFORMATION: antisense probe for HLA-B exon 3 codon 114
      variant 2

<400> SEQUENCE: 255

```
ttttttctc tggtcatgcc cttttttttt                                  30
```

<210> SEQ ID NO 256
<211> LENGTH: 30
<212> TYPE: DNA
<213> ORGANISM: artificial sequence
<220> FEATURE:
<223> OTHER INFORMATION: sense probe for HLA-B exon 3 codon 116 variant
      1

<400> SEQUENCE: 256

```
ttttttcta ccagtacgcc tatttttttt                                  30
```

<210> SEQ ID NO 257
<211> LENGTH: 30
<212> TYPE: DNA
<213> ORGANISM: artificial sequence
<220> FEATURE:
<223> OTHER INFORMATION: sense probe for HLA-B exon 3 codon 116 variant
      2

<400> SEQUENCE: 257

```
ttttttcta ccagtccgcc tatttttttt                                  30
```

<210> SEQ ID NO 258
<211> LENGTH: 30
<212> TYPE: DNA
<213> ORGANISM: artificial sequence
<220> FEATURE:
<223> OTHER INFORMATION: antisense probe for HLA-B exon 3 codon 116
      variant 1

<400> SEQUENCE: 258

```
tttttttta ggcgtactgg tatttttttt                                  30
```

<210> SEQ ID NO 259
<211> LENGTH: 30
<212> TYPE: DNA
<213> ORGANISM: artificial sequence
<220> FEATURE:
<223> OTHER INFORMATION: antisense probe for HLA-B exon 3 codon 116
      variant 2

<400> SEQUENCE: 259

```
tttttttt aggcggactg gtttttttt                                    30
```

<210> SEQ ID NO 260
<211> LENGTH: 30
<212> TYPE: DNA
<213> ORGANISM: artificial sequence
<220> FEATURE:
<223> OTHER INFORMATION: sense probe for HLA-B exon 3 codon 121 variant
      1

<400> SEQUENCE: 260

```
ttttttttgg caaggattac atttttttt                                  30
```

<210> SEQ ID NO 261
<211> LENGTH: 30
<212> TYPE: DNA
<213> ORGANISM: artificial sequence
<220> FEATURE:
<223> OTHER INFORMATION: sense probe for HLA-B exon 3 codon 121 variant
      2

<400> SEQUENCE: 261
tttttttggg caaagattac atctttttt                                    30

<210> SEQ ID NO 262
<211> LENGTH: 30
<212> TYPE: DNA
<213> ORGANISM: artificial sequence
<220> FEATURE:
<223> OTHER INFORMATION: antisense probe for HLA-B exon 3 codon 121
      variant 1

<400> SEQUENCE: 262
tttttttatg taatccttgc ctctttttt                                    30

<210> SEQ ID NO 263
<211> LENGTH: 30
<212> TYPE: DNA
<213> ORGANISM: artificial sequence
<220> FEATURE:
<223> OTHER INFORMATION: antisense probe for HLA-B exon 3 codon 121
      variant 2

<400> SEQUENCE: 263 ttttttgat gtaatctttg cctctttttt                                    30

<210> SEQ ID NO 264
<211> LENGTH: 30
<212> TYPE: DNA
<213> ORGANISM: artificial sequence
<220> FEATURE:
<223> OTHER INFORMATION: sense probe for HLA-B exon 3 codon 131 variant
      1

<400> SEQUENCE: 264
tttttttttg acctgagctc cctttttttt                                   30

<210> SEQ ID NO 265
<211> LENGTH: 30
<212> TYPE: DNA
<213> ORGANISM: artificial sequence
<220> FEATURE:
<223> OTHER INFORMATION: sense probe for HLA-B exon 3 codon 131 variant
      2

<400> SEQUENCE: 265
ttttttttta cctgcgctcc tttttttttt                                   30

<210> SEQ ID NO 266
<211> LENGTH: 30
<212> TYPE: DNA
<213> ORGANISM: artificial sequence
<220> FEATURE:
<223> OTHER INFORMATION: antisense probe for HLA-B exon 3 codon 131
      variant 1

<400> SEQUENCE: 266
tttttttttg gagctcaggt ctctttttt                                    30

```
<210> SEQ ID NO 267
<211> LENGTH: 30
<212> TYPE: DNA
<213> ORGANISM: artificial sequence
<220> FEATURE:
<223> OTHER INFORMATION: antisense probe for HLA-B exon 3 codon 131
      variant 2

<400> SEQUENCE: 267 tttttttta ggagcgcagg tttttttttt                                     30

<210> SEQ ID NO 268
<211> LENGTH: 30
<212> TYPE: DNA
<213> ORGANISM: artificial sequence
<220> FEATURE:
<223> OTHER INFORMATION: sense probe for HLA-B exon 3 codon 135 variant
      1

<400> SEQUENCE: 268 tttttttta ccgcggcgga tttttttttt                                     30

<210> SEQ ID NO 269
<211> LENGTH: 30
<212> TYPE: DNA
<213> ORGANISM: artificial sequence
<220> FEATURE:
<223> OTHER INFORMATION: sense probe for HLA-B exon 3 codon 135 variant
      2

<400> SEQUENCE: 269 tttttttta ccgccgcgga tttttttttt                                     30

<210> SEQ ID NO 270
<211> LENGTH: 30
<212> TYPE: DNA
<213> ORGANISM: artificial sequence
<220> FEATURE:
<223> OTHER INFORMATION: antisense probe for HLA-B exon 3 codon 135
      variant 1

<400> SEQUENCE: 270
ttttttttct tccgccgcgg tttttttttt                                    30

<210> SEQ ID NO 271
<211> LENGTH: 30
<212> TYPE: DNA
<213> ORGANISM: artificial sequence
<220> FEATURE:
<223> OTHER INFORMATION: antisense probe for HLA-B exon 3 codon 135
      variant 2

<400> SEQUENCE: 271
ttttttttct tccgcggcgg tttttttttt                                    30

<210> SEQ ID NO 272
<211> LENGTH: 30
<212> TYPE: DNA
<213> ORGANISM: artificial sequence
<220> FEATURE:
<223> OTHER INFORMATION: sense probe for HLA-B exon 3 codon 143 variant
      1

<400> SEQUENCE: 272
ttttttttct cagatcaccc atttttttttt                                   30

<210> SEQ ID NO 273
<211> LENGTH: 30
```

```
<212> TYPE: DNA
<213> ORGANISM: artificial sequence
<220> FEATURE:
<223> OTHER INFORMATION: sense probe for HLA-B exon 3 codon 143 variant
      2

<400> SEQUENCE: 273 tttttttttct cagatctccc attttttttt                                30

<210> SEQ ID NO 274
<211> LENGTH: 30
<212> TYPE: DNA
<213> ORGANISM: artificial sequence
<220> FEATURE:
<223> OTHER INFORMATION: antisense probe for HLA-B exon 3 codon 143
      variant 1

<400> SEQUENCE: 274
tttttttttt gggtgatctg agtttttttt                                30

<210> SEQ ID NO 275
<211> LENGTH: 30
<212> TYPE: DNA
<213> ORGANISM: artificial sequence
<220> FEATURE:
<223> OTHER INFORMATION: antisense probe for HLA-B exon 3 codon 143
      variant 2

<400> SEQUENCE: 275
tttttttttt gggagatctg agtttttttt                                30

<210> SEQ ID NO 276
<211> LENGTH: 30
<212> TYPE: DNA
<213> ORGANISM: artificial sequence
<220> FEATURE:
<223> OTHER INFORMATION: sense probe for HLA-B exon 3 codon 145 variant
      1

<400> SEQUENCE: 276
ttttttttcc ccagcgcaag tctttttttt                                30

<210> SEQ ID NO 277
<211> LENGTH: 30
<212> TYPE: DNA
<213> ORGANISM: artificial sequence
<220> FEATURE:
<223> OTHER INFORMATION: sense probe for HLA-B exon 3 codon 145 variant
      2

<400> SEQUENCE: 277
ttttttttcc ccagctcaag tgtttttttt                                30

<210> SEQ ID NO 278
<211> LENGTH: 30
<212> TYPE: DNA
<213> ORGANISM: artificial sequence
<220> FEATURE:
<223> OTHER INFORMATION: antisense probe for HLA-B exon 3 codon 145
      variant 1

<400> SEQUENCE: 278
ttttttttta cttgcgctgg gctttttttt                                30

<210> SEQ ID NO 279
<211> LENGTH: 30
<212> TYPE: DNA
<213> ORGANISM: artificial sequence
```

```
<220> FEATURE:
<223> OTHER INFORMATION: antisense probe for HLA-B exon 3 codon 145
      variant 2

<400> SEQUENCE: 279
ttttttttca cttgagctgg gcttttttttt                                           30

<210> SEQ ID NO 280
<211> LENGTH: 30
<212> TYPE: DNA
<213> ORGANISM: artificial sequence
<220> FEATURE:
<223> OTHER INFORMATION: sense probe for HLA-B exon 3 codon 152 variant
      1

<400> SEQUENCE: 280
tttttttttt cccgtgtggc gtttttttttt                                           30

<210> SEQ ID NO 281
<211> LENGTH: 30
<212> TYPE: DNA
<213> ORGANISM: artificial sequence
<220> FEATURE:
<223> OTHER INFORMATION: sense probe for HLA-B exon 3 codon 152 variant
      2

<400> SEQUENCE: 281
tttttttttt cccgtgaggc gtttttttttt                                           30

<210> SEQ ID NO 282
<211> LENGTH: 30
<212> TYPE: DNA
<213> ORGANISM: artificial sequence
<220> FEATURE:
<223> OTHER INFORMATION: antisense probe for HLA-B exon 3 codon 152
      variant 1

<400> SEQUENCE: 282 tttttttttct cgccacacgg gttttttttt                                           30

<210> SEQ ID NO 283
<211> LENGTH: 30
<212> TYPE: DNA
<213> ORGANISM: artificial sequence
<220> FEATURE:
<223> OTHER INFORMATION: antisense probe for HLA-B exon 3 codon 152
      variant 2

<400> SEQUENCE: 283 tttttttttct cgcctcacgg gttttttttt                                           30

<210> SEQ ID NO 284
<211> LENGTH: 30
<212> TYPE: DNA
<213> ORGANISM: artificial sequence
<220> FEATURE:
<223> OTHER INFORMATION: sense probe for HLA-B exon 3 codon 156 variant
      1

<400> SEQUENCE: 284 tttttttag cagctgagag ctctttttttt                                            30

<210> SEQ ID NO 285
<211> LENGTH: 30
<212> TYPE: DNA
<213> ORGANISM: artificial sequence
<220> FEATURE:
<223> OTHER INFORMATION: sense probe for HLA-B exon 3 codon 156 variant
```

```
                                   3

<400> SEQUENCE: 285
ttttttttta gcagcggaga gtttttttt                                30

<210> SEQ ID NO 286
<211> LENGTH: 30
<212> TYPE: DNA
<213> ORGANISM: artificial sequence
<220> FEATURE:
<223> OTHER INFORMATION: antisense probe for HLA-B exon 3 codon 156
      variant 1

<400> SEQUENCE: 286 ttttttttttc tctcagctgc tcttttttttt                              30

<210> SEQ ID NO 287
<211> LENGTH: 30
<212> TYPE: DNA
<213> ORGANISM: artificial sequence
<220> FEATURE:
<223> OTHER INFORMATION: antisense probe for HLA-B exon 3 codon 156
      variant 3

<400> SEQUENCE: 287 ttttttttttc tctccgctgc tttttttttt                               30

<210> SEQ ID NO 288
<211> LENGTH: 30
<212> TYPE: DNA
<213> ORGANISM: artificial sequence
<220> FEATURE:
<223> OTHER INFORMATION: sense probe for HLA-B exon 3 codon 163 variant
      1

<400> SEQUENCE: 288 ttttttttttg gcctgtgcgt gtttttttttt                              30

<210> SEQ ID NO 289
<211> LENGTH: 30
<212> TYPE: DNA
<213> ORGANISM: artificial sequence
<220> FEATURE:
<223> OTHER INFORMATION: sense probe for HLA-B exon 3 codon 163 variant
      2

<400> SEQUENCE: 289 ttttttttttg gcgagtgcgt gtttttttttt                              30

<210> SEQ ID NO 290
<211> LENGTH: 30
<212> TYPE: DNA
<213> ORGANISM: artificial sequence
<220> FEATURE:
<223> OTHER INFORMATION: antisense probe for HLA-B exon 3 codon 163
      variant 1

<400> SEQUENCE: 290
tttttttctc acgcacaggc ctcttttttt                                30

<210> SEQ ID NO 291
<211> LENGTH: 30
<212> TYPE: DNA
<213> ORGANISM: artificial sequence
<220> FEATURE:
<223> OTHER INFORMATION: antisense probe for HLA-B exon 3 codon 163
      variant 2
```

```
<400> SEQUENCE: 291
tttttttctc acgcactcgc ctcttttttt                              30

<210> SEQ ID NO 292
<211> LENGTH: 30
<212> TYPE: DNA
<213> ORGANISM: artificial sequence
<220> FEATURE:
<221> NAME/KEY: primer_bind
<223> OTHER INFORMATION: primer for amplifying the k-ras amplicon

<400> SEQUENCE: 292
actgaatata aacttgtggt agttggacct                              30

<210> SEQ ID NO 293
<211> LENGTH: 20
<212> TYPE: DNA
<213> ORGANISM: artificial sequence
<220> FEATURE:
<221> NAME/KEY: primer_bind
<223> OTHER INFORMATION: primer for amplifying the k-ras amplicon

<400> SEQUENCE: 293
tcaaagaatg gtcctgcacc                                         20

<210> SEQ ID NO 294
<211> LENGTH: 12
<212> TYPE: DNA
<213> ORGANISM: artificial sequence
<220> FEATURE:
<223> OTHER INFORMATION: sense k-ras amplicon

<400> SEQUENCE: 294
gacctggtgg cg                                                 12

<210> SEQ ID NO 295
<211> LENGTH: 12
<212> TYPE: DNA
<213> ORGANISM: artificial sequence
<220> FEATURE:
<223> OTHER INFORMATION: sense k-ras amplicon

<400> SEQUENCE: 295
gacctagtgg cg                                                 12

<210> SEQ ID NO 296
<211> LENGTH: 12
<212> TYPE: DNA
<213> ORGANISM: artificial sequence
<220> FEATURE:
<223> OTHER INFORMATION: sense k-ras amplicon

<400> SEQUENCE: 296
gaccttgtgg cg                                                 12

<210> SEQ ID NO 297
<211> LENGTH: 12
<212> TYPE: DNA
<213> ORGANISM: artificial sequence
<220> FEATURE:
<223> OTHER INFORMATION: sense k-ras amplicon

<400> SEQUENCE: 297
gacctcgtgg cg                                                 12

<210> SEQ ID NO 298
```

```
<211> LENGTH: 12
<212> TYPE: DNA
<213> ORGANISM: artificial sequence
<220> FEATURE:
<223> OTHER INFORMATION: sense k-ras amplicon

<400> SEQUENCE: 298
gacctgatgg cg                                                              12

<210> SEQ ID NO 299
<211> LENGTH: 12
<212> TYPE: DNA
<213> ORGANISM: artificial sequence
<220> FEATURE:
<223> OTHER INFORMATION: sense k-ras amplicon

<400> SEQUENCE: 299
gacctgctgg cg                                                              12

<210> SEQ ID NO 300
<211> LENGTH: 12
<212> TYPE: DNA
<213> ORGANISM: artificial sequence
<220> FEATURE:
<223> OTHER INFORMATION: sense k-ras amplicon

<400> SEQUENCE: 300
gacctgttgg  cg                                                             12

<210> SEQ ID NO 301
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 301
cgccaccagg tc                                                              12

<210> SEQ ID NO 302
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 302
cgccactagg tc                                                              12

<210> SEQ ID NO 303
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 303
cgccactagg tc                                                              12

<210> SEQ ID NO 304
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 304
```

```
cgccacgagg tc                                                          12

<210> SEQ ID NO 305
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 305
cgccatcagg tc                                                          12

<210> SEQ ID NO 306
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 306
cgccacgagg tc                                                          12

<210> SEQ ID NO 307
<211> LENGTH: 12
<212> TYPE: DNA
<213> ORGANISM: artificial sequence
<220> FEATURE:
<223> OTHER INFORMATION: antisense k-ras amplicon

<400> SEQUENCE: 307
cgccacaagg tc                                                          12

<210> SEQ ID NO 308
<211> LENGTH: 9
<212> TYPE: DNA
<213> ORGANISM: artificial sequence
<220> FEATURE:
<223> OTHER INFORMATION: reference sequence for HLA-B codon 69 variant 1

<400> SEQUENCE: 308 gcccaggca                                                               9

<210> SEQ ID NO 309
<211> LENGTH: 9
<212> TYPE: DNA
<213> ORGANISM: artificial sequence
<220> FEATURE:
<223> OTHER INFORMATION: reference sequence for HLA-B allele codon 69
      variant 2

<400> SEQUENCE: 309 accaacaca                                                               9

<210> SEQ ID NO 310
<211> LENGTH: 9
<212> TYPE: DNA
<213> ORGANISM: artificial sequence
<220> FEATURE:
<223> OTHER INFORMATION: resequenced reference HLA-B 0702 codon 69
      variant 1

<400> SEQUENCE: 310 rccmasrca                                                               9

<210> SEQ ID NO 311
<211> LENGTH: 9
<212> TYPE: DNA
```

```
<213> ORGANISM: artificial sequence
<220> FEATURE:
<223> OTHER INFORMATION: reference sequence for HLA-B 7301 codon 69

<400> SEQUENCE: 311 gccaaggca                                                                  9

<210> SEQ ID NO 312
<211> LENGTH: 9
<212> TYPE: DNA
<213> ORGANISM: artificial sequence
<220> FEATURE:
<223> OTHER INFORMATION: reference sequence for HLA-B 13XX codon 69

<400> SEQUENCE: 312 rychmsrcr                                                                  9

<210> SEQ ID NO 313
<211> LENGTH: 9
<212> TYPE: DNA
<213> ORGANISM: artificial sequence
<220> FEATURE:
<223> OTHER INFORMATION: reference sequence for HLA-B 5801 codon 69

<400> SEQUENCE: 313 gcctccgcg                                                                  9

<210> SEQ ID NO 314
<211> LENGTH: 9
<212> TYPE: DNA
<213> ORGANISM: artificial sequence
<220> FEATURE:
<223> OTHER INFORMATION: reference sequence for HLA-B 4601 codon 69

<400> SEQUENCE: 314 ssccaggca                                                                  9

<210> SEQ ID NO 315
<211> LENGTH: 9
<212> TYPE: DNA
<213> ORGANISM: artificial sequence
<220> FEATURE:
<223> OTHER INFORMATION: resequenced reference HLA-B 4006 codon 69
      variant 2

<400> SEQUENCE: 315 mscmasrca                                                                  9

<210> SEQ ID NO 316
<211> LENGTH: 9
<212> TYPE: DNA
<213> ORGANISM: artificial sequence
<220> FEATURE:
<223> OTHER INFORMATION: reference sequence for HLA-B 5101 codon 69

<400> SEQUENCE: 316 acyaacaca                                                                  9

<210> SEQ ID NO 317
<211> LENGTH: 21
<212> TYPE: DNA
<213> ORGANISM: artificial sequence
<220> FEATURE:
<223> OTHER INFORMATION: T7 polymerase recognition sequence included in
      primers for HLA-B amplicons

<400> SEQUENCE: 317
```

```
atgtaatacg actcactata g                                              21

<210> SEQ ID NO 318
<211> LENGTH: 13
<212> TYPE: DNA
<213> ORGANISM: artificial sequence
<220> FEATURE:
<223> OTHER INFORMATION: HLA-B allele probe template
<220> FEATURE:
<221> NAME/KEY: misc_feature
<222> LOCATION: 7
<223> OTHER INFORMATION: v at position 7 is a single nucleotide
      polymorphism

<400> SEQUENCE: 318
tgcgacvtgg ggc                                                       13

<210> SEQ ID NO 319
<211> LENGTH: 13
<212> TYPE: DNA
<213> ORGANISM: artificial sequence
<220> FEATURE:
<223> OTHER INFORMATION: HLA-B allele probe template
<220> FEATURE:
<221> NAME/KEY: misc_feature
<222> LOCATION: 7, 9
<223> OTHER INFORMATION: s at position 7 and m at position 9 are single
      nucleotide polymorphism

<400> SEQUENCE: 319
gaaggasamg ctg                                                       13
```

POPULATION SCALE HLA-TYPING AND USES THEREOF

CROSS-REFERENCE TO RELATED APPLICATIONS

This divisional application claims benefit of priority under 35 U.S.C. §120 of nonprovisional application U.S. Ser. No. 11/711,561, filed Feb. 27, 2007 now U.S. Pat. No. 7,667,026, which claims benefit of priority under 35 U.S.C. §119(e) of provisional U.S. Ser. No. 60/777,078, filed Feb. 27, 2006, now abandoned, the entirety of both of which are hereby incorporated by reference.

BACKGROUND OF THE INVENTION

1. Field of the Invention

The present invention relates generally to the fields of microarray technology and population genotyping. More specifically, the present invention relates to a portable system and method of real-time high throughput population-scale HLA genotyping in a field environment.

2. Description of the Related Art

Bioterrorism and military interests have compelled the Department of Homeland Defense to invest heavily in high speed, flexible and high capacity methods of vaccine development. Recent studies have begun to confirm what basic immunology had predicted, namely that, within a large exposed population, individual response to infection and individual response to vaccination may vary greatly as a function of HLA type (1-2). However, only a few such studies have been performed to date, in part because HLA typing has been too expensive to implement as part of the epidemiology of infectious disease or the clinical epidemiology of vaccine development. Moreover, from the viewpoint of Homeland Defense, even if a thorough knowledge of the relationship between HLA type and infection or vaccine response were known, and even if "personalized" vaccines were available based on the HLA type, the current technologies for HLA-typing do not have rapid field response capability and are too expensive and too complicated to be implemented in the context of a population-scale emergency.

Human immunogenic response to pathogens and vaccinations is dependent on the HLA loci. The response to pathogens is due to two distinct classes of polymorphic cell surface glycoproteins that are encoded by the HLA loci (3). HLA class I molecules identify the endogenous antigen present in the cytoplasm due to infection by bacteria or viruses and present it to the CD8+ cytotoxic T lymphocytes which kill the infected cells. HLA class I molecules also tag the infected cells by displaying exogenously derived epitopes on the surface of antigen-presenting cells for CD4+ helper T cells which results in an immune response against an invading pathogen. A diverse range of specificities for the epitope-HLA-Binding interaction is dependent on the extensive polymorphisms at the HLA loci.

Polymorphisms at the HLA loci are brought about by recombination, gene conversion and mutation and their natural selection in response to pathogens and infectious diseases (4). Hence, a diversity of HLA alleles enhances human ability to respond to and resist infectious and pathogenic agents at the population scale. HLA polymorphisms have been associated with several diseases and most recently with resistance to AIDS virus (5). Since most of the viral vaccines are viral surface antigens in a low dose, one's ability to react to such a vaccination is dependent on the polymorphism at the HLA loci. For example, the haplotype HLA-B8, SC01, DR3 lacks a response gene for hepatitis B virus surface antigen (6). In order to develop a vaccination it is very vital to find out the HLA type and classify the vaccine response to a set of known haplotypes.

The traditional serological methods for HLA typing have been limited to the availability of the allele-specific sera to identify structural differences due to single nucleotide polymorphisms (7). The antibodies used in the conventional methods are specific to HLA surfaces. However, structural differences in the peptide binding groove of HLA heavy chain due to single or multiple nucleotide polymorphisms cannot be easily identified using the antibody-based methods.

Nucleic acid based methods utilize sequence specific oligonucleotide probes (SSOP) or sequence specific primers (SSP). The sequence specific oligonucleotide probe method is based on the use of either individual DNA samples or sequence specific oligonucleotide probes to identify the polymorphism (8). Current methods of primer design rely on simple BLAST like alignments to identify the primers and do not always perform well to pick out the unique primer set. Individual primers identified as specific to the loci are used to amplify the whole locus and specific probes are used to identify the polymorphism.

These are tiered approaches where the resolution is low to medium, and high resolution can be achieved by further probing with specific probes. The two versions of this method are dot blot where the DNA sample is immobilized on a membrane support and a labeled sequence specific oligonucleotide probe is allowed to hybridize to identify the polymorphism in the immobilized sample or a reverse dot blot where the sequence specific oligonucleotide probe is immobilized and a labeled DNA sample is added to the sequence specific oligonucleotide probe to identify the polymorphism. Immobilization of sequence specific oligonucleotide probes allows the testing of several polymorphisms, where as the immobilization of the DNA sample allows the testing of several samples for a specific polymorphism.

The sequence specific primer method uses specific primers targeted to each of the polymorphism (9). The number of primers required for the analysis of a locus depends on the number of polymorphisms in that particular locus. Typically, a large number of PCR reactions are needed to complete the HLA typing. This is a PCR based method where the presence or absence of a polymorphism results in amplification of the product. Using conventional gel electrophoresis the presence or absence of the PCR product can be ascertained. The PCR reactions contain positive control primers that amplify conserved regions.

Other methods are structure based or utilize sequencing methods. A structure-based method to identify polymorphisms is based on the fact that mismatched heteroduplexes containing looped out regions migrated differently than a heteroduplex without any mismatched loops in a non-denaturing gel (10). With the automation of DNA sequencing, HLA typing has been done on sequencing machines (11-12). The methodology is dependent on the number of polymorphisms and the number of exons, for example, for HLA class II the polymorphisms are in exon 2 which has a few hundred bases. In contrast, for class I typing the polymorphisms require several exons to be sequenced and hence become more complicated and can result in errors.

Single nucleotide polymorphisms in the HLA types are shared by the several subtypes of the alleles. This could result in ambiguities when the conventional methods are used. In order to overcome this problem due to cross hybridization, a combination of probes and primers combined with the knowledge of the polymorphisms is essential. Hence, a simple SSOP or sequence specific primer hybridization might not result in the assignment of the HLA type.

The accurate assignment of HLA types is then based on carefully sifting through the patterns of a combination of probes for several subtypes. A PCR based method or a dot blot method would require a high amount of sample and would turn out to be very costly. Thus, a miniaturized technique that requires less amount of sample and is economical is needed. Microarrays (13) in combination with pattern recognition software provide such a platform to generate a 2-dimensional barcode to unambiguously identify the HLA type.

Microarrays are suited ideally for the high-throughput requirements in HLA typing. They offer the convenience of miniaturization and the ability to perform thousands of hybridizations in a single experiment. This highly parallel nature of the microarrays and their unique format makes them ideally suited for field use. In spite of these potential benefits, microarrays have not been perfected for field use in HLA typing. Cost, quality, and portability are among the limiting factors and are dependent on the method of manufacture.

Current microarrays in the market use specific dyes and so a specific type of imager needs to be used. Ideally, an imager should be able to image any dye. Also, current imagers in the market are not portable. Additionally, current analysis packages are equally cumbersome to use and require some manual intervention to identify the patterns.

The first olignucleotide microarray for the detection of allelic variants was reported in 1989 (14). Sequence specific oligonucleotide probes were spotted onto nylon membranes and hybridized to biotinylated CR products of the DNA samples. Genotype of the alleles was identified using the color intensity of the spots. More recently another study reported the use of a 130 probe element DNA microarrays to identify the allelic variations of class II polymorphisms (15). While the applicability of the microarrays to obtain medium to high resolution HLA typing is obvious, the technology in its current form still suffers from several limitations, both technical and economical.

Additionally, using conventional methods, e.g., sequence specific oligonucleotide probes, the DNA sample is double stranded and the probe is single stranded. The presence of a double stranded product reduces the efficiency of hybridization. T7 or T3 polymerase sequences have been used to create single-stranded target molecules by in vitro transcription. Labeling RNA is difficult and hence the amplification methods utilize an end-labeled primer with biotin or a fluorescent dye so that all of the product can be labeled. The presence of biotin could interfere with the amplification procedure.

Furthermore, a significant limitation to performing population-scale HLA typing is the collection of the samples. Traditional methods of sample collection have focused on a blood draw of 10-15 ml by invasive procedures. This form of collection leads to a degradation, contamination and inaccurate results. Blood samples collected in this way would require a large scale handling, storage, and transportation problems that enormously increase the cost and logistical complexity of HLA typing. In addition to the handling and collection problems with the blood draw methods, the storage of isolated DNA becomes an issue. Hence, any technology for population-scale HLA typing must have alternate methods for sample collection and archiving the extracted DNA.

There is a need in the art for improvements in systems and methods for population-scale genotyping. Specifically, the prior art is deficient in a low cost, mass-produced and field-ready portable microarray system using advanced methods of genome analysis for rapid-response HLA typing of large populations. The present invention fulfills this long-standing need and desire in the art.

SUMMARY OF THE INVENTION

The present invention is directed to primers for amplifying an HLA gene. The HLA gene may be HLA A, B or DRB1 or an exon therein. The primers comprise sequences shown in SEQ ID NOS: 14-37.

The present invention also is directed to hybridization probes for detecting single nucleotide polymorphisms (SNPs) in an HLA gene. The hybridization probes comprise about a 9-15mer oligonucleotide complementary to a region containing the SNP and 5' and 3' flanking sequences. The SNPs may be located in HLA-A exon 2 or exon 3 or HLA-B exon 2 or exon 3. The probes comprise sequences shown in SEQ ID NOS: 48-291.

The present invention is directed further to a microarray device comprising a substrate having a cationic surface; and a monolayer comprising one or more of the hybridization probes described herein adsorbed thereto. In a related invention the microarray may comprise an oligo-thymidine co-absorbed with the hybridization probes described herein. In another related invention the oligo-thymidine may comprise a fluorescent dye attached thereto. In yet another related invention the microarray device may comprise a capping agent.

The present invention is directed further still to a kit comprising gene-specific primers for amplifying an HLA gene and the microarray device, both described herein. In a related invention the kit may further comprise buffers and polymerases for a PCR reaction or a fluorescent dye or a combination thereof.

The present invention is directed further still to a system for real-time high throughput population-scale HLA allelotyping in a field environment. The system comprises the microarray device described herein, means for collecting and purifying DNA samples from individuals comprising a population, means for generating by PCR cRNA target amplicons of one or more HLA genes of interest from the collected DNA, and means for assigning an HLA allelotype to each individual HLA gene of interest; wherein individual means and devices comprising said system are portable and operable in real time within the field environment. The primers described herein are useful to generate the cRNA target amplicons.

The present invention is directed further still to a method for real time population-scale HLA allelotyping in a field environment. The method comprises collecting DNA from one or members of the population, purifying the DNA for analysis and generating a target amplicon from an HLA gene of interest comprising the DNA the using gene specific primers described herein. The hybridization probes comprising the microarray described herein are contacted with the target and the hybridization pattern formed after the contact is imaged where each HLA allelotype has a pattern associated therewith. The present invention is directed to a related method comprising further assessing a risk of infection by a biological agent or weapon for each individual based on the assigned allelotype. The present invention is directed to another related method comprising further assessing a response to a particular vaccine against the biological agent or weapon by each individual.

Other and further aspects, features, and advantages of the present invention will be apparent from the following description of the presently preferred embodiments of the invention. These embodiments are given for the purpose of disclosure.

BRIEF DESCRIPTIONS OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A-1J show gels of amplified PCR products of HLA-A and HLA-B loci (FIGS. 1A-1B), HLA-A exons 2 and 3 (FIGS. 1C-1D), HLA-B exons 2 and 3 (FIGS. 1E-1F), HLA-DRB1 locus (FIGS. 1G-1H), and HLA-DRB1 exon 2 (FIGS. 1I-1J) using various primer pairs from Table 2. PCR and gel conditions are described in Example 2.

FIGS. 2A-2B demonstrates that a 558 by amplicon amplified using PCR from DNA extracts of five buccal samples collected using the "mouthwash" method and stored on FTA paper (FIG. 2A) is intact and similar to freshly extracted human DNA from blood samples (FIG. 2B). DNA was extracted and stored on FTA paper cards, then eluted via a GenVault DNA elution product (GenVault, Carlsbad, Calif.). PCR amplification was performed using standard methods and analyzed on agarose gels. Each lane consists of PCR amplified product from a 10 ng starting material of DNA. A positive control with a DNA sample to generate a 558 by amplicon is shown in lane 6 and no amplicon was added in lane 7. The 1 kb size marker is shown in lane 8.

FIGS. 3A-3B are gels of UCLA reference and volunteer samples amplicons. FIG. 3A shows a gel of the 558 by amplicons generated using Fitzco Dacron cheek swabs. Lanes 2-4 show the DNA recovered using Argylla prep particles and lanes 5-7 show the DNA recovered using Qiagen clean up columns. Lane 1 is a molecular weight marker. FIG. 3B is a gel showing the PCR products using specific primers and 4 UCLA reference to standards 59, 15, 20 and 45 and DNA extracted from buccal swabs of two volunteers: MH and BI. 5 ng DNA of each, as assessed by PicoGreen ($\frac{1}{100}^{th}$-$\frac{1}{200}^{th}$ of samples), was used in nested PCR to amplify HLA-B exon 2 yielding a 281 by amplicon. Gel has $\frac{1}{10}^{th}$ of PCR product per lane. Lane 1 in both gels is the molecular weight marker.

FIG. 4A-4B illustrates the effectiveness of the software package ImageAnalyzer in advanced automated image analysis on microarray images. FIG. 4A shows a partially damaged microarray image section. FIG. 4B shows the same image in FIG. 4A after filtering, background compensation and precise gridding by ImageAnalyzer. Spot gridding is marked by circles.

FIGS. 5A-5D show the microarray patterns depicting the results of hybridization using capture probes shown in Table 5 for K-ras 1, K-ras 2 and K-ras 7. FIG. 5A shows the hybridization of all of the targets wildtype and mutants 2-5. FIG. 5B shows the binding of the homozygous wildtype and FIG. 5C shows the binding of the homozygous mutant 7. FIG. 5D shows the binding profile of the heterozygous target sample containing wildtype and mutant 2. Pattern recognition was visual.

FIGS. 6A-6B show a comparison of a UCLA reference sequence, re-sequencing and primary performance data from the HLA-B chip. The grey cells are UCLA allele types. The cells with bold fonts indicate array assay for one or both alleles; the cells with an 'underline' represents that the array is discordant with UCLA allele type and the cells with fonts in italics represent that the sequencing is discordant with UCLA allele type. All other cells represent results with 100% concordance with UCLA allele type.

FIGS. 7A-7H show HLA microarray images for UCLA reference samples 72, 21, 27, 57 respectively and FIGS. 7E-7F show HLA microarray images of DNA from buccal swabs of two volunteers MD and BI respectively. FIG. 7G illustrates the quantification of spot intensity within the arrays of the top panel for codon 9. Data in FIG. 7G is presented as six clusters. The first four clusters correspond to hybridization data from UCLA reference samples of known allelotype at codon 9. Within each cluster, two sets of probe type were tested: a "long probe", i.e., comprising the oligo-T flanking sequences, and a "short probe" where the sequence specific sequence at the center is shortened by one base, in order to determine if specificity can be enhanced. FIG. 7H illustrates similar hybridization results for HLA-B codon 50 with long probes (with flanking segments) and short probes (without flanking probes).

Figure 1A:
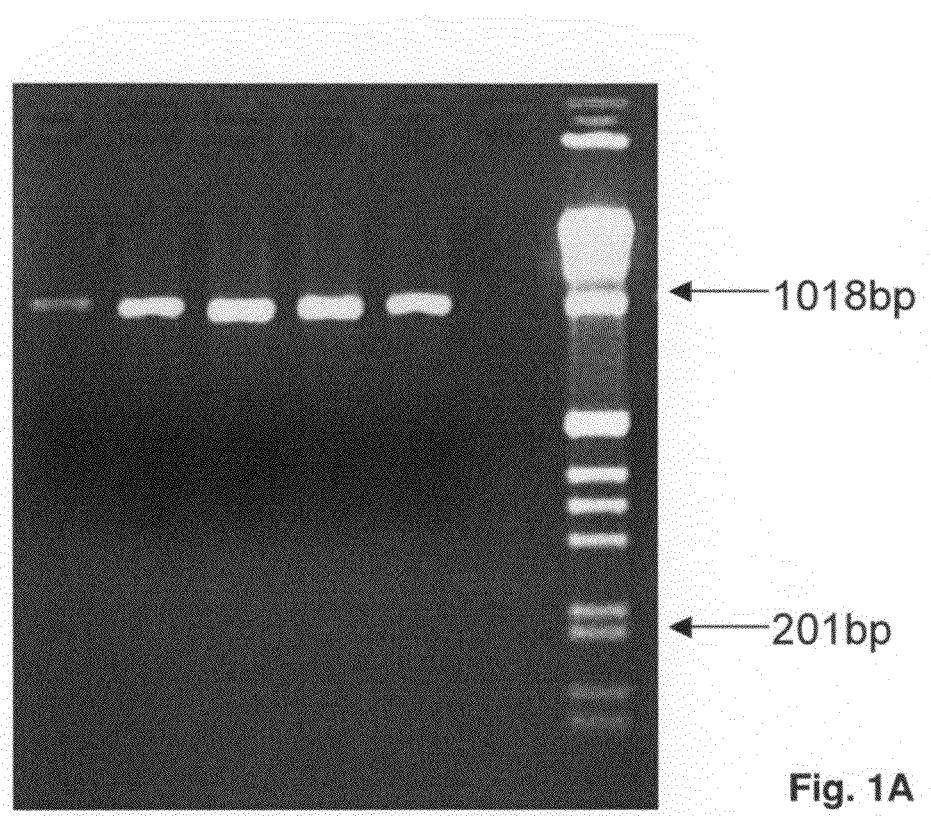

FIG. 10 is a chart listing the 210 HLA alleles identified by automated searching of the PubMed database. Yellow shading indicates the allele is pesent in the UCLA class I panel. Green shading indicates the allele is present in the UCLA class II panel. Orange shading indicates that the allele is present in either the UCLA panel at a higher resolution or at a lower noncoding resolution. Blue shading indicates that the allele is not typed in either UCLA panel.

DETAILED DESCRIPTION OF THE INVENTION

In one embodiment of the present invention there are primers for amplifying an HLA gene. In this embodiment the HLA gene may be HLA A, B or DRB1 or an exon therein.

In one aspect of this embodiment the HLA-A primers may have sequences shown in SEQ ID NOS: 14-15, the HLA-A exon 2 primers may have sequences shown in SEQ ID NOS: 20-21 and the HLA-A exon 3 primers may have the sequences shown in SEQ ID NOS: 22-26. In another aspect the HLA-B primers may have sequences shown in SEQ ID NOS: 16-19, the HLA-B exon 2 primers may have the sequences shown in SEQ ID NOS: 27-28 and the HLA-B exon 3 primers may have the sequences shown in SEQ ID NOS: 29-31. In yet another aspect the HLA-DRB1 primers may have sequences shown in SEQ ID NOS: 32-37 and the HLA-B exon 2 primers may have the sequences shown in SEQ ID NOS: 38-47.

In another embodiment of the present invention there are provided hybridization probes for detecting single nucleotide polymorphisms (SNPs) in an HLA gene, comprising about a 9-15 mer oligonucleotide complementary to a region containing the SNP; and 5' and 3' flanking sequences.

In all aspects of this embodiment the flanking sequences may be oligo-thymidines or an oligo-thymidine-like polyanionic polymer. Also in all aspects the SNPs may be located in HLA-A exon 2 or exon 3, HLA-B exon 2 or exon 3 or HLA-DRB1 exon 2. In one particular aspect the HLA-A exon 2 probes may have the sequences shown in SEQ ID NOS: 48-99 and the HLA-A exon 3 probes may have the sequences shown in SEQ ID NOS: 100-155. In another particular aspect the HLA-A exon 2 probes may have the sequences shown in SEQ ID NOS: 156-239 and the HLA-A exon 3 probes may have the sequences shown in SEQ ID NOS: 240-291.

In yet another embodiment there is provided a microarray device microarray device for allelotyping an HLA gene, comprising a substrate having a cationic surface; and a monolayer comprising one or more of the hybridization probes described supra adsorbed thereto. Further to this embodiment the microarray may comprise and an oligo-thymidine co-absorbed with the hybridization probes. The oligo-thymidine may have about 20 to about 40 thymidines. Further still the oligo-thymidine may comprise a fluorescent dye linked thereto. In another further embodiment the microarray device may comprise a capping agent. In all embodiments the cationic surface may comprise an aminosilane, a guanidinium, tin oxide, aluminum oxide or zirconium oxide or other equivalently charged moiety. Also in all embodiments the substrate may be glass, plastic or a metal.

In a related embodiment the present invention provides a kit for population-scale HLA genotyping, comprising gene-specific primers for amplifying an HLA gene; and the microarray device described supra. Further to this embodiment the kit may comprise buffers and polymerases for a PCR reaction or a fluorescent dye or a combination thereof. Gene-specific primers may the sequences shown in SEQ ID NOS: 14-47.

In yet another embodiment of the present invention there is provided a system for real-time high throughput population-scale HLA allelotyping in a field environment, comprising the microarray device described supra; means for collecting and purifying DNA samples from individuals comprising a population; means for generating by PCR DNA target amplicons of one or more HLA genes of interest from the collected DNA; and means for assigning an HLA allelotype to each individual HLA gene of interest; wherein individual means and devices comprising said system are portable and operable in real time within the field environment.

In all aspects of this embodiment the HLA gene may be HLA-A, HLA-B or HLA-DRB1. Also, in all aspects real time high throughput allelotyping is about 200 to about 300 HLA allelotypes per hour per system operated. In one aspect of this embodiment the means for collecting DNA samples may comprise a container suitable to receive a buccal wash sample, a buccal swab sample or a blood sample collected from the individuals. In another aspect the means for generating target amplicons may comprise HLA gene-specific primers for amplifying the HLA gene of interest. Examples of the gene-specific primers have sequences shown in SEQ ID NOS: 14-47. In yet another aspect the means for assigning an HLA-allelotype to each individual may comprise an imaging device adapted to detect hybridization patterns formed on the microarray device after hybridization of the target to the hybridization probes adsorbed thereto; and pattern recognition software comprising a set of algorithms adapted to recognize the imaged hybridization patterns as HLA allelotypes. Examples of the hybridization probes have sequences shown in SEQ ID NOS: 48-291.

In yet another embodiment of the present invention there is provided a method for real time population-scale HLA allelotyping in a field environment, comprising collecting DNA from one or members of the population; purifying the DNA for analysis; generating a target amplicon from an HLA gene of interest comprising the DNA using gene specific primers; contacting the hybridization probes comprising the microarray described supra with the target; and imaging the hybridization pattern formed after the contact wherein each HLA allelotype has a pattern associated therewith.

Further to this embodiment the method may comprise storing the collected DNA. In another further embodiment the method may comprise assessing a risk of infection by a biological agent or weapon for each individual based on the assigned allelotype. In yet another further embodiment the method may comprise assessing a response to a particular vaccine against the biological agent or weapon by each individual.

In all embodiments the DNA may be collected from blood, with a buccal wash or with a buccal swab. Also, the gene-specific primers may have sequences shown in SEQ ID NOS: 14-47. In addition, the hybridization probes have sequences shown in SEQ ID NOS: 48-291.

As used herein, the term, "a" or "an" may mean one or more. As used herein in the claim(s), when used in conjunction with the word "comprising", the words "a" or "an" may mean one or more than one. As used herein "another" or "other" may mean at least a second or more.

Provided herein is a human leukocyte antigen (HLA) chip and microarray technology to enable population-scale HLA-typing in a simple, portable and field-ready environment. The HLA chip is designed to thoroughly analyze the human HLA-B genotype. It is contemplated that HLA chips may be designed to analyze the entire human HLA loci. This microarray technology is effective to HLA type a large exposed population, for example, although not limited to, 100,000 individuals per week using as few as 5-10 low cost, portable field laboratories.

It also is contemplated that data acquired through population typing can be used in real time to anticipate, at the HLA level, individual risk of infection by a biological weapon or to anticipate personalized response to vaccination against the same infectious agent. Additionally, variants of the HLA chip may be used to provide field-ready neonatal screening in a third world environment or for battlefield-ready personnel identification. Furthermore, the HLA typing technology may be used for civilian identification during or after a disaster or for forensic applications. Thus, population-scale HLA typing has applications in military, anti-bioterrorism or epidemiological contexts.

Real-time interpretation of microarray data can be made by non-experts in a field application environment. This may be implemented in the field through low cost, compact, highly portable microarray imagers. Complete HLA analysis using equipment readily portable in a vehicle may have an overall process time from sample collection to a final HLA identification of less than 4 hours. This duty cycle can be maintained with a manual-only throughput of about 20 samples per person per 4 hours. With minimal sample handling automation, throughput routinely can be scaled up to a steady state of about 200 to about 300 complete HLA genotypes per hour per workstation in a mobile, field-ready environment.

Furthermore, pattern recognition software, such as ImageAnalyzer (16), provides barcode-like simplicity in the image analysis and conversion of microarray fluorescence patterns into an HLA allelotype. The algorithms comprising the pattern recognition software use traditional and novel statistical and data mining approaches, such as, but not limited to, Euclidian and mutual information based distances and Fourier and wavelet transformations. The microarray pattern recognition software is effective for recognizing the patterns of hybridization and for extracting automatically information of what genomes/species are present based on the possibly fuzzy patterns of hybridization. This information then is compared to an existing database of patterns for each HLA subtype based on the expected pattern of spots. Such a system may include a user-friendly GUI interphase that can function on a laptop computer. A "cam-corder" sized portable microarray imager is suitable to work in a highly portable data collection environment.

The microarray design and fabrication or microfabrication requires no chemical modification of the probe ends, i.e., no linker, to immobilize the oligonucleotide probe to the surface (17). The surface saturation by the oligonucleotide occurs at a fraction of the concentration of olignucleotides required for covalent attachment. Thus, all of the oligonucleotide delivered to the surface is immobilized via adsorptive association with a monolayer surface that bears a net positive charge and additionally may be hydrophobic or hydrophilic. The shape and morphology of the spot is dependent of the initial contact of the drop dispensed by the microarrayer. Since there is no covalent bond formation, spot to spot variations are minimized.

The present invention provides short oligonucleotide probes of about 9 to about 15mers to discriminate among single nucleotide polymorphisms within the target. These probes are flanked with oligo-thymidine (oligo-T) sequences. Preferably the flanked probes comprise about 30 nucleotides total. It is further contemplated that analogues of oligo-T may be used as flanking sequences. Without being limiting an oligo-thymidine-like polyanionic polymer flanking sequence, e.g., polysulfonate, may replace the oligo-T flanking sequences. It is contemplated that the probes are designed for all the clinically relevant HLA subtypes. The current number of alleles at the IMGT/HLA sequence database is 977 alleles for HLA Class I and 652 alleles for HLA Class II (18). Useful probes provided herein are effective to discriminate within HLA-A exon 2 (SEQ ID NOS: 48-99) and exon 3 (SEQ ID NOS: 100-155), HLA-B exon 2 (SEQ ID NOS: 156-239) and exon 3 (SEQ ID NOS: 240-291) and HLA-DRB1 exon 2.

Fabrication of the microarrays used herein uses an extremely simple and reproducible method (17) employing adsorptive, noncovalent attachment of the short oligonucleotide probes to the positive or cationic surface. For example, the cationic surfaces may comprise or may be coated with an amine function such as, although not limited to, aminosilane, or may comprise a guanidinium group. Alternatively, the surface may comprise a cationic metal or metal oxide, such as tin oxide, zirconium oxide or aluminum oxides or other metal oxides with a net positive charge or other equivalently charged moiety. Such oxide coatings may be particulate in nature or may be smooth and placed on a glass, plastic or metal substrate.

Generally, the method requires deposition or printing of oligo-T flanked oligonucleotide probes dissolved in water onto the cationic or net positively charged surface of the substrate. Alternatively, the oligo-T flanked probes may be co-printed with a second, constant oligonucleotide probe. This probe is the same in all instances of printing and may comprise an oligo-T sequence with about T20 to about T40 bases. Furthermore, the oligo-T sequence may comprise a dye linked thereto. An example of a dye may be, but not limited to, Cy-5

It is contemplated that the oligo-T sequence is inert with respect to nucleic acid hybridization to human DNA for HLA typing. The oligo-T is introduced as a marker to identify where the nucleic acid probes have printed, either by the direct detection of the oligo-T coupled to a dye or by oligo-T hybridization to dye-labeled oligo-adenine (oligo-A), the Watson-Crick complement of oligo-T. The inclusion of oligo-T improves the ability to orient hybridization image data for analysis and is useful for quality control during microarray fabrication.

In addition, on an amine coated surface, probe deposition may be followed by drying and capping of those residual surface charges or moieties not involved in direct association with adsorbed probe molecules. For example, and as known and standard in the art, capping of an aminosilane surface can be performed by reacting unused amine groups with a capping agent such as the surfactant sodium dodecylsulfate. Alternatively, for ceramic or metal oxide surfaces, capping may be performed by reacting the surface with boric acid, fluoride ion or phosphate. After drying and capping, the attached oligonucleotides cannot be removed from the surface under standard hybridization and washing conditions, including high salt, 5M NaCl and high pH treatments. Thus, within the fabricated microarray, even though the adsorbed oligonucleotide is bound, presumably via multiple contacts to the surface and, therefore, may have lost configurational freedom required to form a perfect double helix with its cognate target, the product of such adsorptive coupling, followed by judicious capping to neutralize excessive charges on the surface, displays specificity for duplex formation which is as high as that seen in a standard solution state hybridization reaction or for surface hybridization to probes linked covalently to the surface at a single point.

PCR primers for the HLA locus are designed using novel algorithms to compute the frequency of occurrence of short subsequences, i.e., n-mers of oligonucleotide sequences of length of n=5-25+ nucleotides in any genome within a reasonable time, e.g., minutes (19-20). These algorithms are used to perform a comparative statistical analysis of the presence of all possible "n-mers" in genomes of more than 250 microbial, viral and multicellular organisms, including humans. The results show a remarkable similarity of presence/absence distributions for different n-mers in all genomes. It suggests that the presence/absence distribution of n-mers in all genomes considered, provided that the condition $M<<4^n$ holds, where M is the total genome sequence length, can be treated as nearly random. The massive computational analysis of the presence/absence of short subsequences in more than one genome simultaneously was performed for all published, i.e., prior to May 2002, microbial and virus genomes and was repeated for the 1600+ genomes which were available by May 2003. This produces unique sequences that are not repeated, anywhere in a given genome.

These new algorithms and data structures, together with the collection of 1600+ complete genomes, make it possible to significantly improve the quality of PCR primers design process itself. Using these algorithms, it is possible to find primers which appear exactly once and differ from the rest of n-mers in the entire human genome, including known SNPs, by at least 2 or 3 mismatches. Furthermore, primers are excluded which are present in some bacterial/viral genomes. Such massively parallel primer design is particularly important, when considering buccal washes as a population-scale DNA source, in that such samples may contain up to 50% of some other contamination. The efficacy of this approach is demonstrated in the Examples presented herein in that a set of primers reported in a PCR/microarray study (15) prime several other chromosomes in addition.

Thus, the present invention provides primers or primer pairs effective to amplify HLA class I and class II loci. For example, for primary PCR reaction primers with SEQ ID NOS: 14-15 are useful to amplify the class I HLA-A locus and primers with SEQ ID NOS: 16-19 are useful to amplify the HLA-B locus. In secondary PCR reactions HLA-A exons 2 and 3 may be amplified with SEQ ID NOS: 20-21 and SEQ ID NOS: 22-26, respectively. HLA-B exons 2 and 3 may be amplified with SEQ ID NOS: 27-28 and SEQ ID NOS: 29-31, respectively. In addition, the class II HLA-DRB1 locus may be amplified in primary PCR reactions using primers with SEQ ID NOS: 32-37. Secondary PCR is performed to amplify HLA-DRB1 exon 2 using primers with SEQ ID NOS: 38-47. These primers are effective to amplify all alleles comprising the gene, i.e., the primers are gene specific and allele blind. The allele fine structure of interest within the entire amplified gene is determined by hybridization of the PCR product to probes in the microarray as provided herein.

DNA samples may be obtained from a spot of dried blood, from buccal wash DNA, DNA from a single 10 µl finger prick or DNA from a paraffin-embedded thin section. Preferably, the DNA samples are buccal DNA samples collected via the "mouthwash" method or buccal swab sample collected on Fitzco Dacron swabs (21). DNA extracted from the samples may be stored or archived on FTA paper (GenVault, Carlsbad, Calif.). This method of immobilization of the sample onto the treated FTA paper provides for archiving and, subsequently, for complete recovery of the DNA without degradation and suitable for PCR reactions.

The targets for the short oligonucleotide probes used herein are single stranded DNA transcribed from the amplified DNA sample or denatured double stranded PCR products. The amplification methods described herein produce labeled dsDNA PCR products. The DNA can be directly chemically labeled using modified PCR primers or cis-platinum conjugated dyes in one simple reaction (22) and is hydrolyzed at the same time with controlled alkaline treatment. This produces uniformly labeled DNA for hybridization.

The present invention also provides a kit comprising one or more primer pairs of HLA allele forward and reverse primers suitable to amplify exactly one or several DNA regions in a DNA sample. Optionally, the kit may further comprise one or more microarrays with HLA probes as described herein. Particularly, these kits may have primer pairs and, optionally, microarrays designed to hybridize HLA-A, HLA-B or HLADRB1 loci and determine which SNPs are present in the sample, thereby genotyping an individual or a population. Furthermore, the kits may comprise suitable buffers and polymerases for a PCR reaction.

Particularly, the present invention provides a method for genotyping and allelotyping that uses human DNA collected from blood, buccal swabs or buccal wash. Collected samples may be used immediately or may be stored in the dry state. A gene specific PCR using the primers disclosed herein amplifies an HLA gene of interest, e.g., HLA-A, -B or -C or HLA-DRB1 or other HLA genes, in the purified DNA without allele bias. The exact allele type in any particular human DNA sample is determined by measuring the pattern of hybridization to the sequence-specific probes on the microarray. The pattern of hybridization determines the allele.

The following example(s) are given for the purpose of illustrating various embodiments of the invention and are not meant to limit the present invention in any fashion.

EXAMPLE 1

Primers for Amplification of Class I and II HLA Loci

Validation of Algorithms for Design of SNP Specific Primers

Forward primer 5'GCTCCCACTCCATGAGGTAT3' (SEQ ID NO: 1) and reverse primer 5'ATACCTCATG-GAGTGGGAGC3' (SEQ ID NO: 2) was used to amplify an exon 2 PCR product for Class I HLA-B type to generate a specific product of 456 by (15). The algorithms presented herein are used to ascertain the uniqueness of these primers to see if they primed only the exon 2 the Class I HLA-B locus. It was determined that the forward primer could bind to 11 other locations within chromosome 6 and also bind to one other location on chromosome X. The reverse primer for exon 2 of the Class I HLA-B locus was found to bind to five other locations on chromosome 6 and one location on chromosome 4 and 13. Another primer 5'ACCCGGTTTACCCG-GTTTCATTTG3' (SEQ ID NO: 6) for the amplification of exon 3 of Class I HLA-B was found to bind in eight locations on chromosome 6 other than intron 2, position 164-184, and to several other chromosomes (Table 1).

Table 1 shows the number of times the primer or substrings of the primer sequences, shown underlined, were found in locations other than the correct one. The algorithm (19-20) clearly shows that the design of the primers is very crucial for performing high resolution HLA typing. The issue is complicated further by the possibility of contamination from other bacterial and viral genomes commonly present in human bodily fluids.

TABLE 1

| Primer | Seq Id No. | Sequence (5'-3') | Chromosome | Occurrence |
|---|---|---|---|---|
| Forward Exon 2 | 1 | gctcccactccatgaggtat | 6 | 12 |
|  | 1, 3 | gctcccactccatgaggtat | X | 1 |
| Reverse Exon 2 | 2 | atacctcatggagtgggagc | 6 | 6 |
|  | 2, 4 | aaatgaaaccgggtaaac | 4 | 1 |
|  | 2, 5 | aaatgaaaccgggtaaac | 13 | 1 |
| Forward Exon 3 | 6 | acccggtttacccggttcatttg | 6 | 9 |
|  | 6, 7 | acccgtttacccggttcatttg | 9 | 1 |
|  | 6, 8 | acccgtttacccggttcatttg | 9, 3, 11 | 2 |
|  | 6, 9 | acccgtttacccggttcatttg | 9, 13 | 1 |
|  | 6, 10 | acccgtttacccggttcatttg | 1, 3, 11 | 1 |
|  | 6, 11 | acccgtttacccggttcatttg | 11, 2, 3 | 2 |
|  | 6, 12 | acccgtttacccggttcatttg | 18 | 1 |
|  | 6, 13 | acccgtttacccggttcatttg | 4, 10 | 1 |

Primer Design for Amplification of HLA-B and HLA Gene Cluster

A simple 500 by long amplicon spanning the entire region of interest for each HLA gene and a pair of approximately 250 by long products are generated. This is suitable for a simple PCR assay for HLA-A, B or DRB1. However, the entire HLA gene cluster would require 14 or 28 primer pairs designed by this method.

For each of the 14 HLA loci, i.e., ten class I HLA loci and 4 class II loci, the hypervariable region of interest spans approximately 500 bp. Therefore the primer design problem is to find a set of forward and reverse primers that are thermodynamically similar, but distinct relative to the human genome and other genomes which would contaminate the buccal DNA. To initiate the process, an approximately 100 by region is identified at each end of the 14 approximately 500 by HLA loci. A set of all possible 18-20 mer primers is readily obtained for these pair-wide 100 by domains using the calculational tools described herein. This set of approximately 1400 forward and 1400 reverse primers is then filtered to obtain a subset of similar calculated thermodynamic stabilities. It is then additionally filtered to remove those with Watson-Crick complementarity with others in the set and to eliminate capacity for hairpin formation.

The remaining set is then additionally filtered relative to the remainder of the human genome set of 18-20 mers to eliminate the capacity for false priming. Since the desired PCR products are relatively small the greatest weight is given to pair-wise possible forward primer/reverse primer associations elsewhere which would produce PCR products smaller than 2000 bp. This is based upon the practical observation that spurious reactions producing products that are greater than 2000 by are highly inefficient.

It is contemplated that the above described filtering process will produce several possible forward/reverse pairings for each of the 14 HLA loci. These primer pairs are tested individually in a 96-well thermal cycler environment and the products analyzed by electrophoresis to obtain that subset that functions optimally in an experimental context. This final level of primer filtering is done with both pure human DNA obtained from blood and also with human-non-human mixtures obtained from the buccal wash method Specific Primer Sequences Table 2 is a representative list of primary and secondary primers effective to amplify HLA A, B and DRB loci and the identified exons.

TABLE 2

| HLA Primers | SEQ ID | Label | Sequence |
|---|---|---|---|
| Primary Class I | | | |
| A-LOC-FP1 | 14 | | GCCTCTGYGGGGAGAAGCAA |
| A-LOC-RP1 | 15 | | GTCCCAATTGTCTCCCCTCCTT |
| B-LOC-FP1 | 16 | | GGGAGGAGMGAGGGGACCGCAG |
| B-LOC-RP2 | 17 | | TTCTCCATTCAASGGAGGGCGACA |
| B-LOC-RP1 | 18 | | GGAGGCCATCCCGGGCGATCTAT |
| B-LOC-RP3 | 19 | | GGAGGCCATCCCCGGCGACCTAT |
| Secondary Class I | | | |
| AX2-FP-1 | 20 | biotin | AGCCGCGCCKGGAGGAGGGTCG |
| AX2-RP-1 | 21 | biotin | GCCCGTCCGTGGGGATGAG |
| AX3-FP-1 | 22 | biotin | CAAAAATCCCCCCRGGTTGGTCGG |
| AX3-RP-1 | 23 | biotin | GGCCCTGGTACCCGTGCGCTG |
| AX3-FP2 | 24 | biotin | GTTTCATTTTCAGTTTAGGCCA |
| AX3-RP-2 | 25 | biotin | GTGCGCTGCAGCGTCTCCTTCC |
| AX3-RP-2 | 26 | biotin | GTGCGCTGCAGCGTCTCCTTCC |
| BX2-FP-2 | 27 | biotin | GAGCCGCGCCGGKAGGAGGGTC |
| BX2-RP-2 | 28 | biotin | GGTCACTCACCGKCCTCGCTCT |
| BX3-FP-1 | 29 | biotin | GGGGCCAGGGTCTCACA |
| BX3-RP1 | 30 | biotin | CCCACTGCCCCTGGTACC |
| BX2-RP-3 | 31 | biotin | CGGGCCGTMCGTGGGGATGG |
| Primary Class II | | | |
| DRB-LOC-FP1a | 32 | | CTTGGAGGTCTCCAGAACAGG |
| DRB-LOC-FP1b | 33 | | CTTAGAGGTCTCCAGAACCGG |
| DRB-LOC-RP1a | 34 | | GCCCCCAGCACCCACCTCCCTT |
| DRB-LOC-RP1b | 35 | | GCCCCCTGTACCCCCTCCCAC |
| DRB-LOC-RP1c | 36 | | GCTCCGTGCACCCACCTCCCTT |
| DRB-LOC-RP1d | 37 | | GCCGCCCGCACCCACCTCCCTT |
| Secondary Class II | | | |
| DRB1-X2-FP1a | 38 | biotin | CACAGCACGTTTCTTGGAGG |
| DRB1-X2-FP1b | 39 | biotin | TCCCCACAGCACGTTTCTTGA |
| DRB1-X2-FP1c | 40 | biotin | TCCCCACAGCACGTTTCTTGTG |
| DRB1-X2-FP1d | 41 | biotin | CCCCACAGCACGTTTCCTGTG |
| DRB1-X2-FP1e | 42 | biotin | CAGCACGTTTCTTGGAGCAGGT |
| DRB1-X2-FP1f | 43 | biotin | TCCCACAGCAGGTTTCCTGTG |
| DRB1-X2-FP1g | 44 | biotin | CCCACAGCACGTTTCTTGGAGT |
| DRB1-X2-RP1a | 45 | biotin | CACACACACACACACACTCAGATTC |
| DRB1-X2-RP1b | 46 | biotin | CACACACACAACCACACTCAGATTC |
| DRB1-X2-RP1c | 47 | biotin | CACACACACACACAGAGTCAGATTC |

EXAMPLE 2

Primary and Secondary Amplification of Class I and II HLA Loci

HLA-A and B Loci and Exons 2 and 3

Figure 1B:
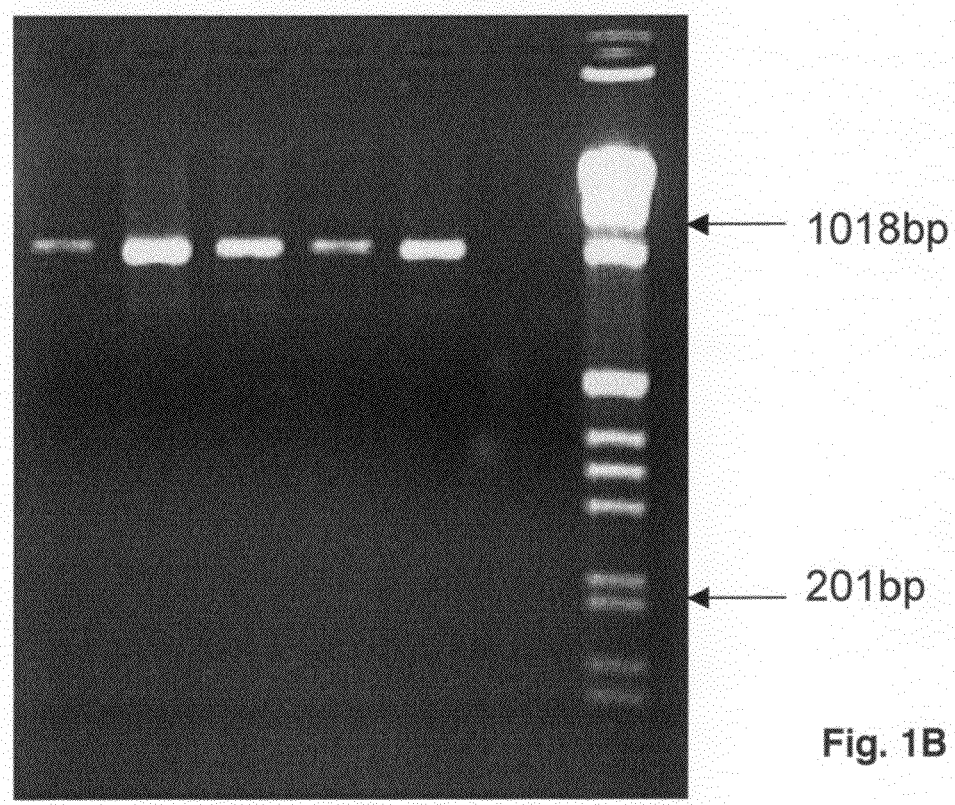

In primary PCR reactions primer pairs A-LOC-FP1/A-LOC-RP1 for HLA-A locus and B-LOC-FP1/B-LOC-RP1 for HLA-B locus are used to generate amplified products of various UCLA standards, a positive control and a negative control. The PCR protocol is for a 50 μL volume in 96 well plate: one pre-PCR denaturing cycle 94° C. for 4 min, 35 PCR cycles at 98° C. for 1 min, 71° C. for 1 min, 72° C. for 1 min; hold cycle 72° C. for 7 min (polymerase: Roche Fast Start Taq). Amplified products (10 μL samples) are run on a 2% agarose gel at 150 volts for 35 min (Lane 1: C1-034, Lane 2: C1-035, Lane 3: C1-036 and Lane 4: CCR1), a positive control (Lane 5: Roche DNA) and a negative control (Lane 6: H₂O); the last lane has weight standards. The gels show products of 980 by for HLA-A (FIG. 1A) and 1007 by for HLA-B (FIG. 1B).

In secondary PCR reactions primer pairs A-X2-FP1/A-X2-RP1 and A-X3-FP1/A-X3-RP1 for HLA-Ax2 and HLA-Ax3 exons are used to generate amplified products.

Figure 1C:
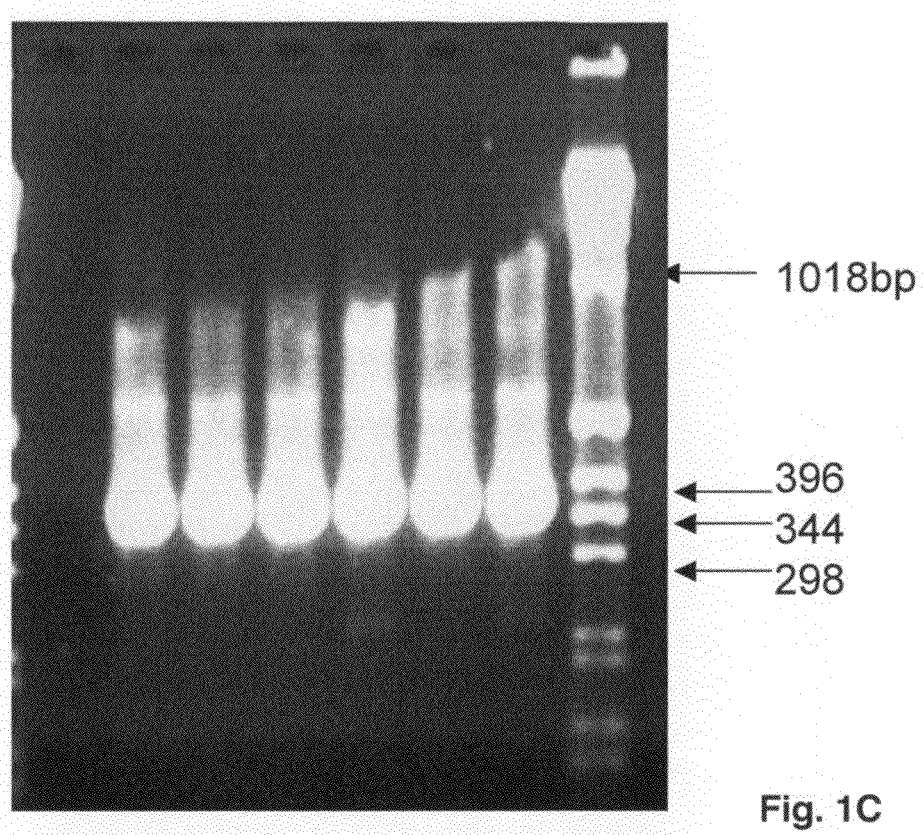
Figure 1D:
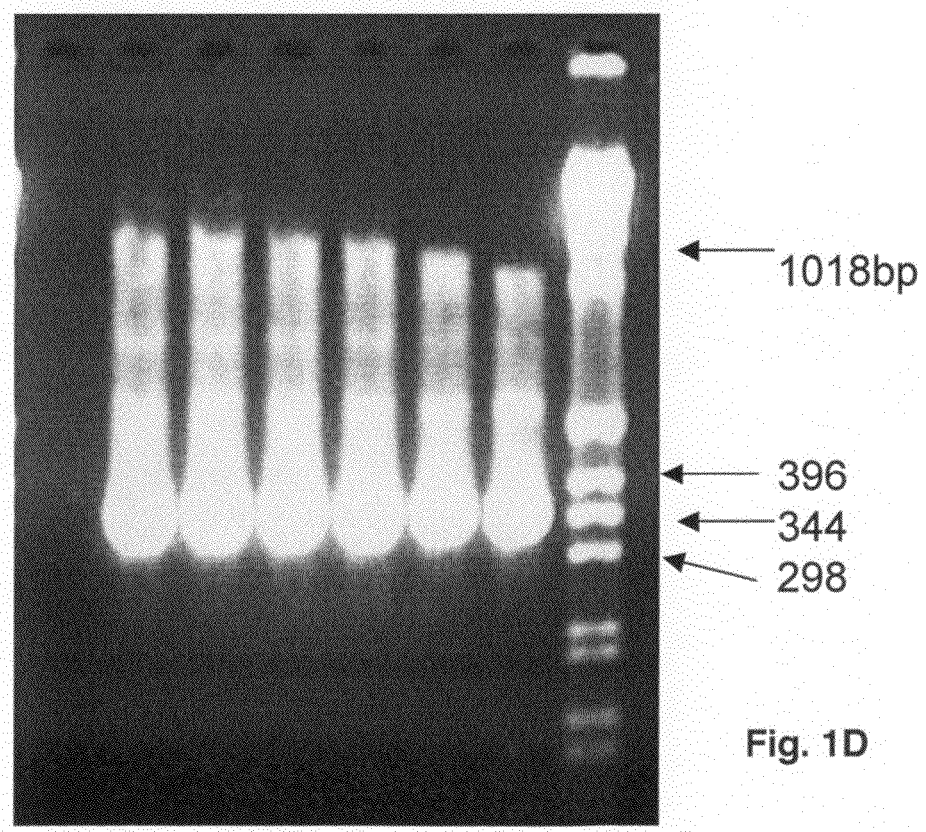

The PCR protocol is for a 50 µL volume in 96 well plate: one pre-PCR denaturing cycle 94° C. for 4 min, 35 PCR cycles at 98° C. for 1 min, one of 58.3, 60.7, 63.3, 66.0, 68.6, or 71.0° C. for 30 sec, and hold cycle 72° C. for 7 min (polymerase: Lucigen EconoTaq). Amplified products (10 µL samples) are run on a 2% agarose gel at 150 volts for 45 min (Lane 1: Aex2 or Aex3 negative control, Lane 2: 58.3° C., Lane 3: 60.7° C., Lane 4: 63.3° C., Lane 5: 66.0° C., Lane 6: 68.6° C., Lane 7: 71.0° C.; FIGS. 1C-1D).

Figure 1E:
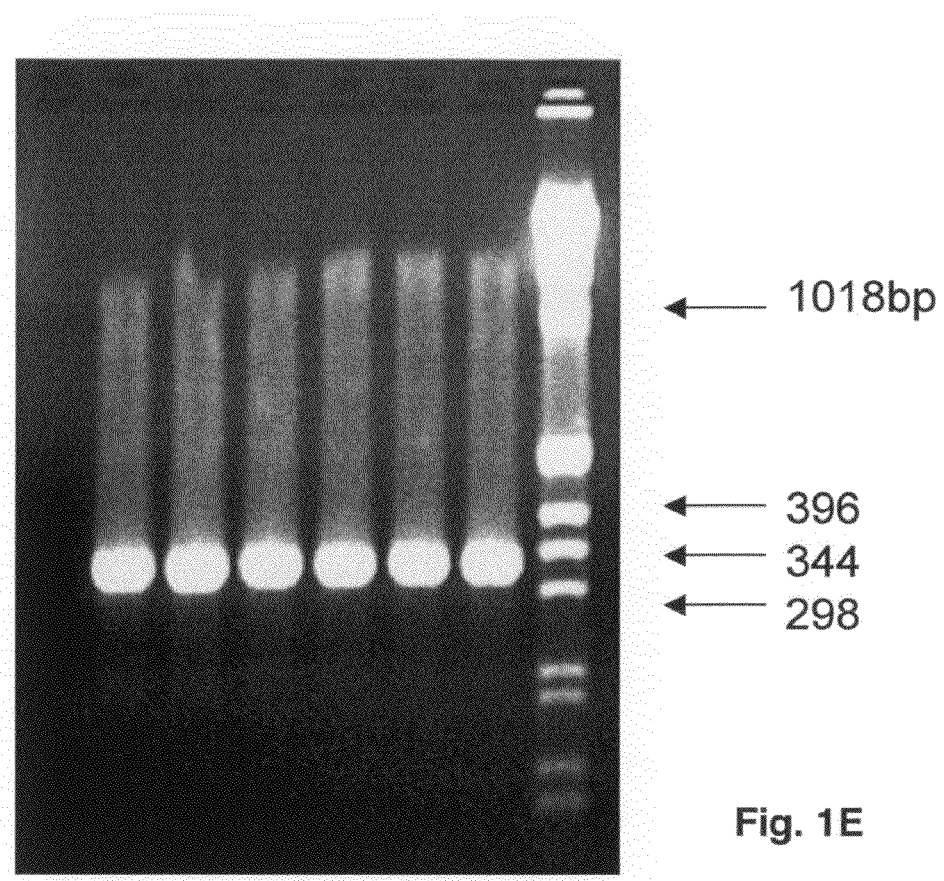
Figure 1F:
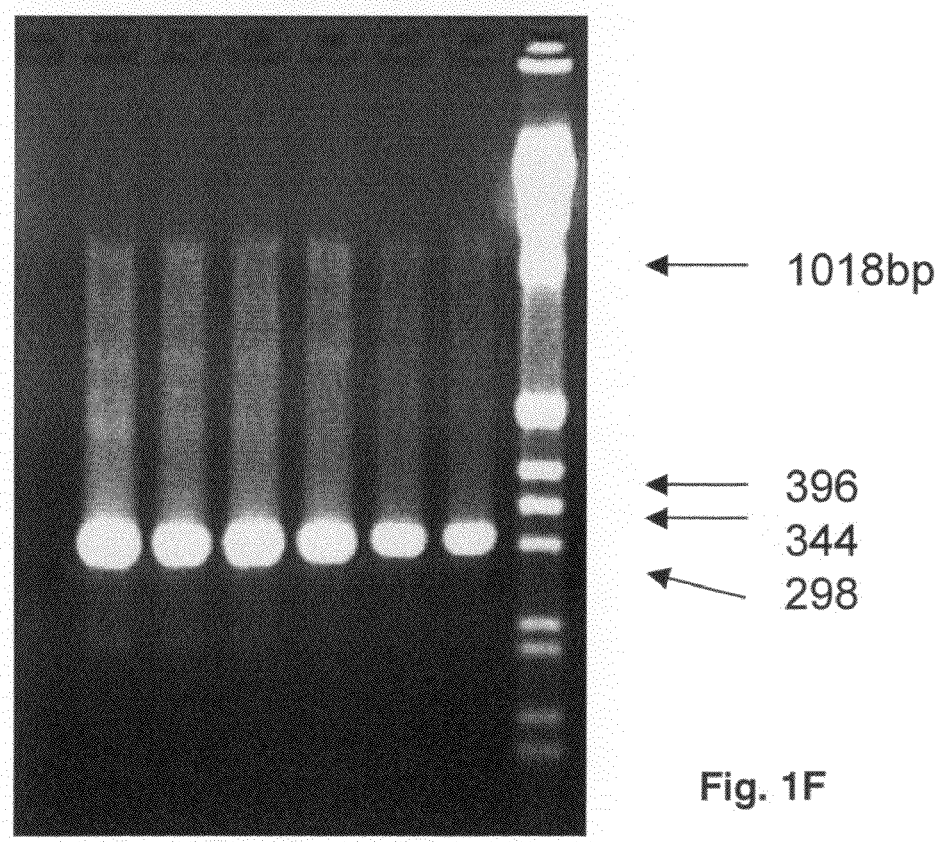

In secondary PCR reactions primer pairs B-X2-FP1/B-X2-RP1 and B-X3-FP1/B-X3-RP1 for HLA-Bx2 and HLA-Bx3 exons are used to generate amplified products. The PCR protocol is for a 50 µL volume in 96 well plate: one pre-PCR denaturing cycle 94° C. for 4 min, 35 PCR cycles at 98° C. for 1 min, one of 60.7, 63.3, 66.0, 68.6, 71.0, or 73.0° C. for 30 sec, and hold cycle 72° C. for 7 min (polymerase: Roche Fast Start Taq). Amplified products (10 µL samples) are run on a 2% agarose gel at 150 volts for 45 min (Lane 1: Aex2 or Aex3 negative control, Lane 2: 60.7° C., Lane 3: 63.3° C., Lane 4: 66.0° C., Lane 5: 68.6° C., Lane 6: 71.0° C., Lane 7: 73.0° C.; FIGS. 1E-1F). The gel shows product around 1018 bp.

HLA-DRB1 Locus and Exons 2 and 3

Figure 1G:
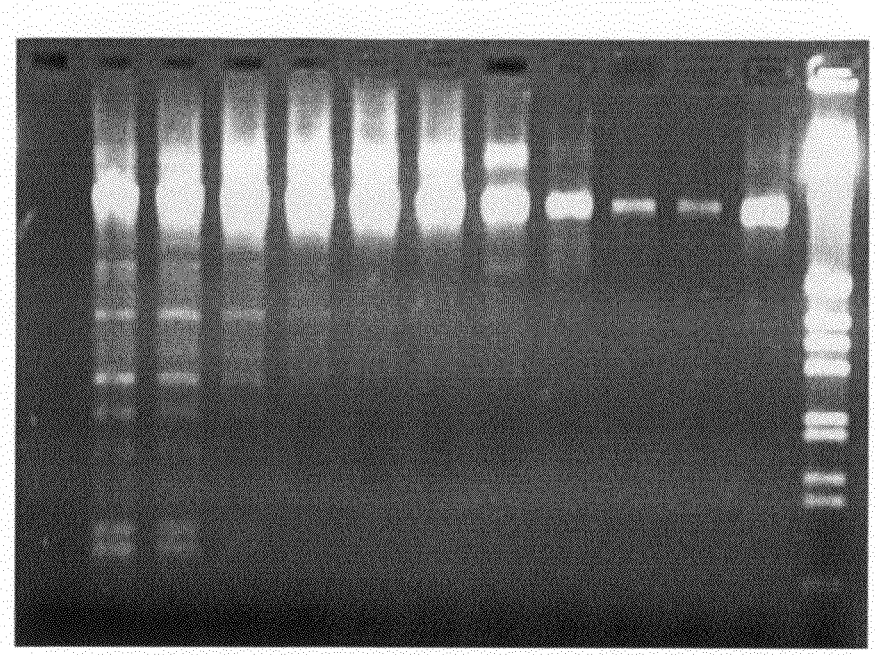

In a primary PCR reaction primer pair DRB-LOC-FP1a/DRB-LOC-RP1 for HLA-A locus and B-LOC-FP1/B-LOC-RP1 for HLA-B locus are used to generate amplified products. The PCR protocol is for a 25 µL volume in 96 well plate: one pre-PCR denaturing cycle 94° C. for 4 min, 35 PCR cycles at 98° C. for 1 min, one of 55.2, 56.5, 58.3, 60.7, 63.3, 66.0, 68.6, 71.0, 73.0, 74.4, or 75.2° C. for 30 sec, and hold cycle 72° C. for 7 min (polymerase: Roche Fast Start Taq). Amplified products (10 µL samples) are run on a 2% agarose gel at 150 volts for 35 min (Lane 1: DRB1 negative control, Lane 2: 55.2° C., Lane 3: 56.5° C., Lane 4: 58.3° C., Lane 5: 60.7° C., Lane 6: 63.3° C., Lane 7: 66.0° C., Lane 8: 68.6° C., Lane 9: 71.0° C., Lane 10: 73.0° C., Lane 11: 74.4° C., Lane 12: 75.2° C.; FIG. 1G).

Combinations of primer pairs are used to amplify HLA-DRB1. The PCR protocol is for a 25 µL volume in 96 well plate: one pre-PCR denaturing cycle 94° C. for 4 min, 35 PCR cycles at 98° C. for 1 min, 74° C. for 1 min, 72° C. for 1 min; hold cycle 72° C. for 7 min (polymerase: Roche Fast Start Taq). Amplified products (10 µL samples) are run on a 2% agarose gel at 150 volts for 35 min (Lane 1: DRB-LOC-FP1a/DRB-LOC-RP1a, Lane 2: DRB-LOC-FP1a/DRB-LOC-RP1b, Lane 3: DRB-LOC-FP1a/DRB-LOC-RP1c, Lane 4: DRB-LOC-FP1a/DRB-LOC-RP1d, Lane 5: DRB-LOC-FP1a/DRB-LOC-RP1a and Lane 6: DRB-LOC-FP1b/DRB-LOC-FP1a); the last lane has weight standards (FIG. 1H).

Secondary PCR reactions are run to amplify a HLA-DRB1 exon 2 genomic DNA template using primer pair DRB-x2-FP1g/DRB-x2-RP1a under conditions as described for FIG. 1G. Amplified products (10 µL samples) are run on a 2% agarose gel at 150 volts for 35 min (Lane 1: DRB1ex2 negative control, Lane 2: 55.2° C., Lane 3: 56.5° C., Lane 4: 58.3° C., Lane 5: 60.7° C., Lane 6: 63.3° C., Lane 7: 66.0° C., Lane 8: 68.6° C., Lane 9: 71.0° C., Lane 10: 73.0° C., Lane 11: 74.4° C., Lane 12: 75.2° C.; FIG. 1I).

Figure 1H:
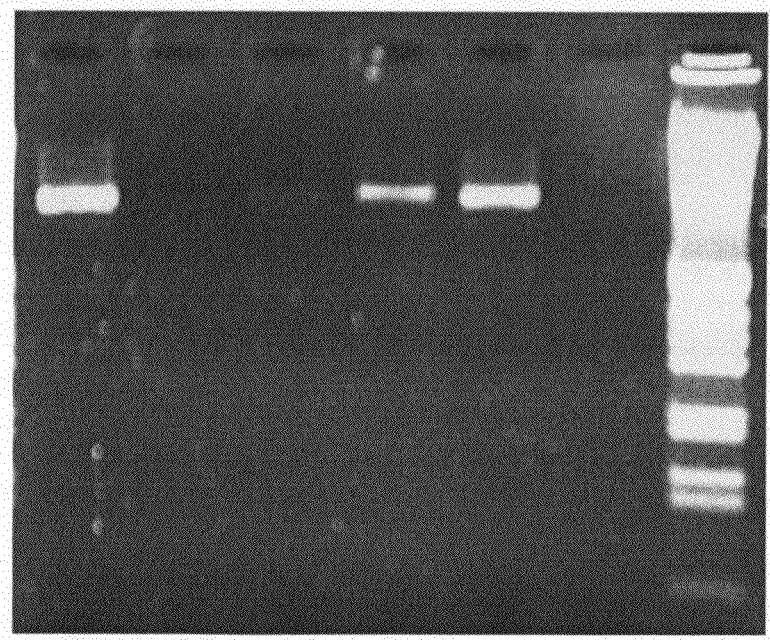
Figure 1I:
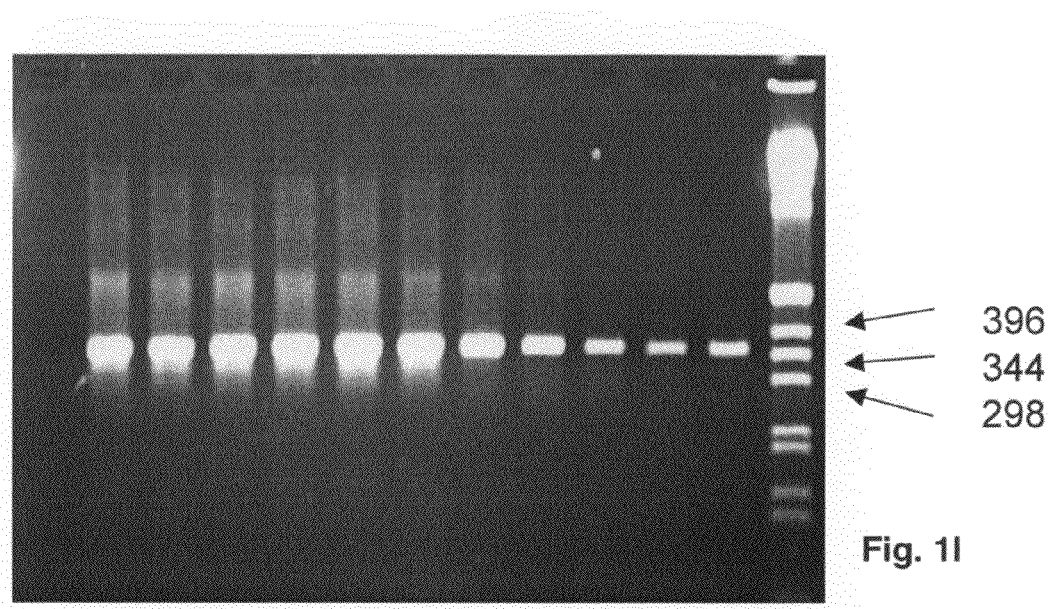
Figure 1J:
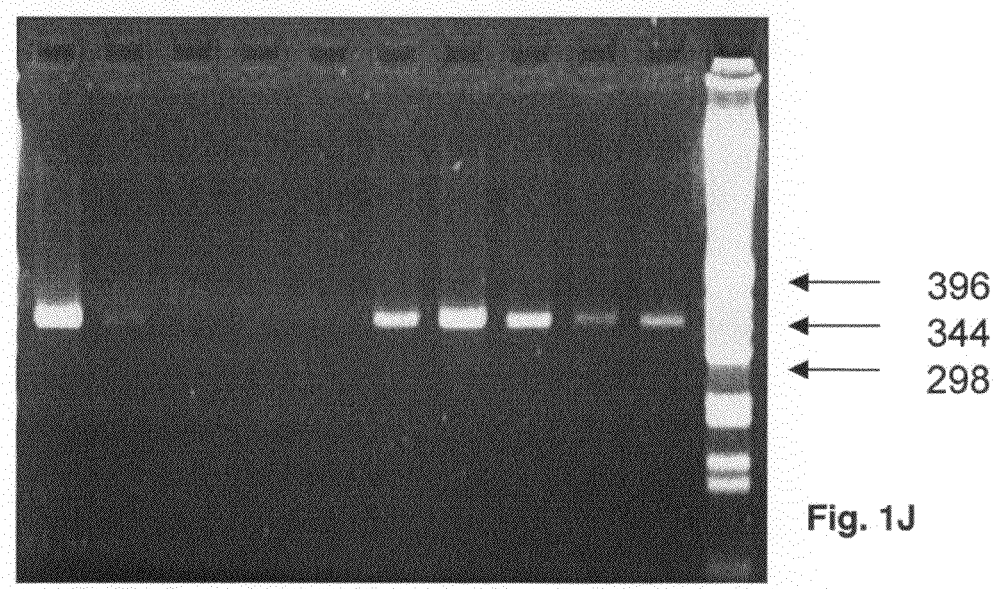

Combinations of primer pairs are used to amplify a HLA-DRB1 exon 2 genomic DNA template under conditions as described for FIG. 1H. Amplified products (10 µL samples) are run on a 2% agarose gel at 150 volts for 35 min (Lane 1: DRB-x2-FP1g/DRB-x2-RP1a, Lane 2: DRB-x2-FP1g/DRB-x2-RP1b, Lane 3: DRB-x2-FP1g/DRB-x2-RP1c, Lane 4: DRB-x2-FP1a/DRB-x2-RP1a, Lane 5: DRB-x2-FP1b/DRB-x2-RP1a, Lane 6: DRB-x2-FP1c/DRB-x2-RP1a, Lane 7: DRB-x2-FP1d/DRB-x2-RP1a, Lane 8: DRB-x2-FP1e/DRB-x2-RP1a, Lane 9: ORB-x2-FP1f/DRB-x2-RP1a, Lane 10: DRB-x2-FP1g/DRB-x2-RP1a) and the last lane has weight standards (FIG. 1J)

EXAMPLE 3

Probe Design for Microarray

General Design

A suitably designed microarray is used to test the hybridization parameters in all possible nearest neighbor contexts for a given mismatch. This allows for emulation of any sort of single nucleotide polymorphism. For a triple sequence there are 64 combinations which are studied by the central base pair and mispair in their nearest neighbor contexts. The results from all these combinations, enables prediction of the binding properties of the single nucleotide polymorphism for any HLA subtype. This is a much better estimate of the binding characteristics than from thermal melting profiles.

Briefly, for the HLA-B model the known allelic diversity of HLA-B defines 137 polymorphisms of clinical or epidemiological value, thus requiring a set of 137 allele specific probes to provide for a full hybridization analysis. Using the adsorptive approach to microarray manufacture described herein produces excellent single nucleotide specificity with probes in the 12-15 base range. A set of all 11-16 base long candidate probes which include the polymorphisms near the calculated center position, i.e., position 3 to N-2, to avoid end artifacts are generated by calculation. This probe set then is filtered to obtain a subset with identical calculated thermodynamic stabilities in binding cognate, perfectly matched target. For that standard, a calculated Tm of 55° C. in 0.1 M NaCl is set.

From the primary filtered subset of probe candidates, a second filtering step relative to the remainder of the human genes is performed to eliminate those probe candidates which also appear in repetition sequences elsewhere, or at any other site in the HLA locus. Since hybridization is to be performed on PCR amplified targets, additional stringency will not be required in principle. However, for completeness the secondarily filtered set also will be analyzed for similarity to the entirety of the 1600 genome library of microbial and non-human vertebrate sequences described herein. These probes are used to manufacture microarrays.

Specific Probe Sequences

Tables 3-6 identify probe sequences for HLA A and HLA B loci, exons 2-3, respectively. oligo-T flanking segments are introduced at the 3' and 5' end of each probe, such that the flanking segments adsorb to the array surface but have little or no affinity for the solution state target nucleic acid. Probe recognition size is about 9-15 bases and oligo-T segments were added to both the 3' and the 5' side for a final overall length of 30 bases for all microarray probes.

TABLE 3

| Probe | Sequence | SEQ ID |
|---|---|---|
| AX2-C002-SE-V1-1 | TTTTTTTTTGCTCCCACTCCACTTTTTTTT | 48 |
| AX2-C002-SE-V2-1 | TTTTTTTTGCTCTCACTCCATTTTTTTTT | 49 |
| AX2-C002-AS-V1-1 | TTTTTTTTTTGGAGTGGGAGCTCTTTTTTT | 50 |
| AX2-C002-AS-V2-1 | TTTTTTTCTATGGAGTGAGAGCTCTTTTTT | 51 |
| AX2-C009-SE-V1-1 | TTTTTTTTGTATTTCTTCACATCTTTTTTT | 52 |

TABLE 3-continued

| Probe | Sequence | SEQ ID |
|---|---|---|
| AX2-C009-SE-V3-1 | TTTTTTTTGTATTTCTCCACATTTTTTTTT | 53 |
| AX2-C009-AS-V1-1 | TTTTTTTTTATGTGAAGAAATACTCTTTTTT | 54 |
| AX2-C017-AS-V3-1 | TTTTTTTTTGTGGAGAAATACTCTTTTTTT | 55 |
| AX2-C017-SE-V1-1 | TTTTTTTTTCCGCGGGGAGCTTTTTTTTT | 56 |
| AX2-C017-SE-V2-1 | TTTTTTTTTCAGTGGAGAGCCCTTTTTTTT | 57 |
| AX2-C017-AS-V1-1 | TTTTTTTTTCTCCCCGCGGCTTTTTTTTT | 58 |
| AX2-C017-AS-V2-1 | TTTTTTTTTGCTCTCCACTGCCTTTTTTTT | 59 |
| AX2-C024-SE-V1-1 | TTTTTTTTTTTCATCGCCGTGTTTTTTTTT | 60 |
| AX2-C024-SE-V2-1 | TTTTTTTTTCTTCATCGCAGTGTTTTTTTT | 61 |
| AX2-C024-AS-V1-1 | TTTTTTTTTCCACGGCGATGAATTTTTTTT | 62 |
| AX2-C024-AS-V2-1 | TTTTTTTTTCCACTGCGATGAAGTTTTTTT | 63 |
| AX2-C036-SE-V1-1 | TTTTTTTTTCTCGGTTCGACAGCTTTTTTT | 64 |
| AX2-C036-SE-V2-1 | TTTTTTTCTCGGTTTGACAGCGTTTTTTTT | 65 |
| AX2-C036-AS-V1-1 | TTTTTTTTTCTGTCGAACCGCTTTTTTTTT | 66 |
| AX2-C036-AS-V2-1 | TTTTTTTCTGCTGTCAAACCGCTTTTTTTT | 67 |
| AX2-C044-SE-V1-1 | TTTTTTTTTCCAGAGGATGGAGTTTTTTTT | 68 |
| AX2-C044-SE-V2-1 | TTTTTTTTTCCAGAAGATGGAGTTTTTTTT | 69 |
| AX2-C044-AS-V1-1 | TTTTTTTTTCCATCCTCTGGCCTTTTTTTT | 70 |
| AX2-C044-AS-V2-1 | TTTTTTTTTCCATCTTCTGGCCTTTTTTTT | 71 |
| AX2-C049-SE-V1-1 | TTTTTTTTTTGGGCGCCGTGTTTTTTTTTT | 72 |
| AX2-C049-SE-V2-1 | TTTTTTTTTCGGGCACCGTGTTTTTTTTTT | 73 |
| AX2-C049-AS-V1-1 | TTTTTTTTTCTCACGGCGCCCTTTTTTTTT | 74 |
| AX2-C049-AS-V2-1 | TTTTTTTTTCCCACGGTGCCCTTTTTTTTT | 75 |
| AX2-C056-SE-V1-1 | TTTTTTTTTAGGGGCCGGAGCTTTTTTTTT | 76 |
| AX2-C056-SE-V2-1 | TTTTTTTTTGAGGGTCCGGAGCTTTTTTTT | 77 |
| AX2-C056-AS-V1-1 | TTTTTTTTTTCCGGCCCCTCTCTTTTTTTT | 78 |
| AX2-C056-AS-V2-1 | TTTTTTTCTCTCCGGACCCTCTCTTTTTTT | 79 |
| AX2-C062-SE-V1-1 | TTTTTTTCTGGACCAGGAGACTTTTTTTTT | 80 |
| AX2-C062-SE-V4-1 | TTTTTTTCTGGACGAGGAGACTTTTTTTTT | 81 |
| AX2-C062-AS-V1-1 | TTTTTTTTTCGTCTCCTGGTCCTTTTTTTT | 82 |
| AX2-C062-AS-V4-1 | TTTTTTTTTCGTCTCCTCGTCCTTTTTTTT | 83 |
| AX2-C066-SE-V1-1 | TTTTTTTTTGGAATGTGAAGGCTTTTTTTT | 84 |
| AX2-C066-SE-V2-1 | TTTTTTTTTGGAAAGTGAAGGCTTTTTTTT | 85 |
| AX2-C066-AS-V1-1 | TTTTTTTTTCCTTCACATTCCGTTCTTTTTT | 86 |
| AX2-C066-AS-V2-1 | TTTTTTTTTCCTTCACTTTCCGTTCTTTTTT | 87 |
| AX2-C070-SE-V1-1 | TTTTTTTTTGCCCACTCACAGAACTTTTTT | 88 |
| AX2-C070-SE-V2-1 | TTTTTTTTTGCCCAGTCACAGAACTTTTTT | 89 |
| AX2-C070-AS-V1-1 | TTTTTTTTTCTGTGAGTGGGCTTTTTTTTT | 90 |
| AX2-C070-AS-V2-1 | TTTTTTTTTCTGTGACTGGGCTCTTTTTTT | 91 |
| AX2-C076-SE-V2-1 | TTTTTTTTTCCGAGAGAACCTGTTTTTTTT | 92 |
| AX2-C076-SE-V3-1 | TTTTTTTTTTCGAGCGAACCTGTTTTTTTT | 93 |
| AX2-C076-AS-V2-1 | TTTTTTTTTCAGGTTCTCTCGGCTTTTTTT | 94 |
| AX2-C076-AS-V3-1 | TTTTTTTTTCAGGTTCGCTCGTCTTTTTTT | 95 |
| AX2-C081-SE-V1-1 | TTTTTTTTTGACCCTGCGCGGTCTTTTTTT | 96 |
| AX2-C081-SE-V2-1 | TTTTTTTTTGATCGCGCTCCGTCTTTTTTT | 97 |
| AX2-C081-AS-V1-1 | TTTTTTTTTCCGCGCAGGGTCTTTTTTTTT | 98 |
| AX2-C081-AS-V2-1 | TTTTTTTTTCGGAGCGCGATCTTTTTTTTT | 99 |

TABLE 4

| Probe | Sequence | SEQ ID |
|---|---|---|
| AX3-C095-SE-V1-1 | TTTTTTCTTCACACCATCCAGACTTTTTTT | 100 |
| AX3-C095-SE-V2-1 | TTTTTTTTTCCACACCGTCCAGACTTTTTT | 101 |
| AX3-C095-AS-V1-1 | TTTTTTTATTCTGGATGGTGTCATTTTTTT | 102 |
| AX3-C095-AS-V2-1 | TTTTTTTATTCTGGACGGTGTGTTTTTTTT | 103 |
| AX3-C097-SE-V1-1 | TTTTTTTTTCCAGAGGATGTATTTTTTTTT | 104 |
| AX3-C097-SE-V3-1 | TTTTTTTTTCCAGATGATGTATGTTTTTTT | 105 |
| AX3-C097-AS-V1-1 | TTTTTTTTTATACATCCTCTGGAATTTTTT | 106 |
| AX3-C097-AS-V3-1 | TTTTTTTCATACATCATCTGGAATTTTTTT | 107 |
| AX3-C105-SE-V1-1 | TTTTTTTTTGGTCGGACGGGTTTTTTTTTT | 108 |
| AX3-C105-SE-V2-1 | TTTTTTTTTGGCCGGACGGGTTTTTTTTTT | 109 |
| AX3-C105-AS-V1-1 | TTTTTTTTTCCCGTCCGACCTTTTTTTTTT | 110 |
| AX3-C105-AS-V2-1 | TTTTTTTTTCCCGTCCGGCCTTTTTTTTTT | 111 |
| AX3-C109-SE-V1-1 | TTTTTTTTTCGGCGCTTCCTCCTTTTTTTT | 112 |
| AX3-C109-SE-V2-1 | TTTTTTTTTCTGCGCCTCCTCCTTTTTTTT | 113 |
| AX3-C109-AS-V1-1 | TTTTTTTTTGGAGGAAGCGCCTTTTTTTTT | 114 |
| AX3-C109-AS-V2-1 | TTTTTTTTTTGGAGGAGGCGCTTTTTTTTT | 115 |
| AX3-C114-SE-V2-1 | TTTTTTTTTGTACCGGCAGGATTTTTTTTT | 116 |
| AX3-C114-SE-V3-1 | TTTTTTTTGTACCAGCAGGACTTTTTTTTT | 117 |
| AX3-C114-AS-V2-1 | TTTTTTTTTTCCTGCCGGTACTTTTTTTTT | 118 |
| AX3-C114-AS-V3-1 | TTTTTTTTTGTCCTGCTGGTACTTTTTTTT | 119 |
| AX3-C126-SE-V1-1 | TTTTTTTTTCCCTGAAAGAGGATTTTTTTT | 120 |
| AX3-C126-SE-V2-1 | TTTTTTTTTCTGCCCTGAACGAGTTTTTTT | 121 |
| AX3-C126-AS-V1-1 | TTTTTTTTTTCCTCTTTCAGGGTTTTTTTT | 122 |
| AX3-C126-AS-V2-1 | TTTTTTTTTCTCTCGTTCAGGGCTTTTTTT | 123 |
| AX3-C139-SE-V1-1 | TTTTTTTTTTATGGCGGCTCAGCATTTTTT | 124 |
| AX3-C139-SE-V2-1 | TTTTTTTTTCATGGCAGCTCAGCATTTTTT | 125 |

TABLE 4-continued

| Probe | Sequence | SEQ ID |
|---|---|---|
| AX3-C139-AS-V1-1 | TTTTTTTTCCTGAGCCGCCATTCTTTTTTT | 126 |
| AX3-C139-AS-V2-1 | TTTTTTTCCTGAGCTGCCATGCTTTTTTT | 127 |
| AX3-C142-SE-V1-1 | TTTTTTTTCTCAGATCACCAAGTTTTTTT | 128 |
| AX3-C142-SE-V3-1 | TTTTTTTTTCAGACCACCAAGTTTTTTT | 129 |
| AX3-C142-AS-V1-1 | TTTTTTCTCTTGGTGATCTGAGTATTTTT | 130 |
| AX3-C142-AS-V3-1 | TTTTTTTCTCTTGGTGGTCTGATTTTTTT | 131 |
| AX3-C145-SE-V1-1 | TTTTTTTAAACCAAGCGCAAGTTTTTTT | 132 |
| AX3-C145-SE-V3-1 | TTTTTTTAAACCCAGCGCAAGCTTTTTTT | 133 |
| AX3-C145-AS-V1-1 | TTTTTTTTTACTTGCGCTTGGTTTTTTT | 134 |
| AX3-C145-AS-V3-1 | TTTTTTTTTCTTGCGCTGGGTTTTTTTT | 135 |
| AX3-C152-SE-V1-1 | TTTTTTTTTGCCCATGTGGCGTTTTTTT | 136 |
| AX3-C152-SE-V2-1 | TTTTTTTTTGCCCATGAGGCGTTTTTTT | 137 |
| AX3-C152-AS-V1-1 | TTTTTTTCTCGCCACATGGGCTTTTTTT | 138 |
| AX3-C152-AS-V2-1 | TTTTTTTTCTCGCCTCATGGGCTTTTTTT | 139 |
| AX3-C152-SE-V1-2 | TTTTTTTTTCCCATGTGGCGGTTTTTTT | 140 |
| AX3-C152-SE-V2-2 | TTTTTTTTTCCCATGAGGCGGTTTTTTT | 141 |
| AX3-C152-AS-V1-2 | TTTTTTTTCCCGCCACATGGGTTTTTTT | 142 |
| AX3-C152-AS-V2-2 | TTTTTTTTCCCGCCTCATGGGTTTTTTT | 143 |
| AX3-C156-SE-V2-1 | TTTTTTTTAGCAGCAGAGAGCTCTTTTTTT | 144 |
| AX3-C156-SE-V3-1 | TTTTTTTTAGCAGTGGAGAGCTCTTTTTTT | 145 |
| AX3-C156-AS-V2-1 | TTTTTTTTTGCTCTCTGCTGCTTTTTTT | 146 |
| AX3-C156-SE-V3-1 | TTTTTTTTTGCTCTCCACTGCTTTTTTT | 147 |
| AX3-C163-SE-V1-1 | TTTTTTTTTAGGGCACGTGCGCTTTTTTT | 148 |
| AX3-C163-SE-V2-1 | TTTTTTTTTAGGGCCGGTGCTCTTTTTTT | 149 |
| AX3-C163-AS-V1-1 | TTTTTTTTTCGCACGTGCCCTTTTTTTT | 150 |
| AX3-C163-AS-V2-1 | TTTTTTTTTGCACCGGCCCTTTTTTTT | 151 |
| AX3-C166-SE-V1-1 | TTTTTTTTTGTGGAGTGGCTCTTTTTTT | 152 |
| AX3-C166-SE-V2-1 | TTTTTTTTTGTGGACGGGCTCTTTTTTT | 153 |
| AX3-C166-AS-V1-1 | TTTTTTTTTGAGCCACTCCACTTTTTTT | 154 |
| AX3-C166-AS-V2-1 | TTTTTTTTTGAGCCCGTCCACTTTTTTT | 155 |

TABLE 5

| Probe | Sequence | SEQ ID |
|---|---|---|
| BX2-C009-AS-V1-1 | TTTTTTTTGGTGTAGAAATACTCTTTTTTT | 156 |
| BX2-C009-AS-V2-1 | TTTTTTTTTGTGTGGAAATACTCTTTTTTT | 157 |
| BX2-C009-AS-V3-1 | TTTTTTTTTGTGTCGAAATACTCTTTTTTT | 158 |
| BX2-C011-SE-V1-1 | TTTTTTTATCACCGCCATGTCTTTTTTT | 159 |
| BX2-C011-SE-V2-1 | TTTTTTTATCACCTCCGTGTCTTTTTTT | 160 |
| BX2-C011-SE-V3-1 | TTTTTTTATCACCGCCGTGTCTTTTTTT | 161 |
| BX2-C011-AS-V1-1 | TTTTTTTTTGACATGGCGGTGCTTTTTTT | 162 |
| BX2-C011-AS-V2-1 | TTTTTTTTTGACACGGAGGTGCTTTTTTT | 163 |
| BX2-C011-AS-V3-1 | TTTTTTTTTGACACGGCGGTGCTTTTTTT | 164 |
| BX2-C024-AS-V1-1 | TTTTTTTTTCACTGCGATGAAGTTTTTTT | 165 |
| BX2-C024-AS-V2-1 | TTTTTTTTCCACTGAGATGAAGTTTTTTT | 166 |
| BX2-C024-AS-V3-1 | TTTTTTTTTCACGGTGATGAAGTTTTTTT | 167 |
| BX2-C024-AS-V4-1 | TTTTTTTTCCACTGCAATGAAGTTTTTTT | 168 |
| BX2-C031-SE-V1-1 | TTTTTTTTCGACACCCAGTTCTTTTTTT | 169 |
| BX2-C031-SE-V2-1 | TTTTTTTTCGACACGCTGTTCTTTTTTT | 170 |
| BX2-C031-SE-V3-1 | TTTTTTTTCGACACGCAGTTCTTTTTTT | 171 |
| BX2-C031-SE-V4-1 | TTTTTTTCTGACGGCACCCAGCCTTTTTT | 172 |
| BX2-C031-AS-V1-1 | TTTTTTTCTACGAACTGGGTGTTTTTTT | 173 |
| BX2-C031-AS-V2-1 | TTTTTTTCTACGAACAGCGTGTTTTTTT | 174 |
| BX2-C031-AS-V3-1 | TTTTTTTCTACGAACTGCGTGTTTTTTT | 175 |
| BX2-C031-AS-V4-1 | TTTTTTTTTCTGGGTGCCGTCTTTTTTT | 176 |
| BX2-C031-AS-V1-2 | TTTTTTTCTACGAACTGGGTGCTTTTTTT | 177 |
| BX2-C031-AS-V2-2 | TTTTTTCTACGAACAGCGTGTCTTTTTT | 178 |
| BX2-C031-AS-V3-2 | TTTTTTCTACGAACTGCGTGTCTTTTTT | 179 |
| BX2-C031-AS-V1-3 | TTTTTTTTCGAACTGGGTGTTTTTTTT | 180 |
| BX2-C031-AS-V2-3 | TTTTTTTTGAACTGCGTGTCGTTTTTTT | 181 |
| BX2-C035-SE-V1-1 | TTTTTTTCTTTCGTGAGGTTCGTTTTTTT | 182 |
| BX2-C035-SE-V2-1 | TTTTTTTTTTCGTGCGGTTCGTTTTTTT | 183 |
| BX2-C035-SE-V2-2 | TTTTTTTTTGTTCGTGCGGTTCTTTTTTT | 184 |
| BX2-C041-SE-V1-1 | TTTTTTTTTACGCCGCGAGTCTTTTTTT | 185 |
| BX2-C041-SE-V2-1 | TTTTTTTTTACGCCACGAGTCTTTTTTT | 186 |
| BX2-C041-SE-V1-2 | TTTTTTTTTTCGCCGCGAGTCTTTTTTT | 187 |
| BX2-C045-AS-V1-2 | TTTTTTTTTGCTCCTCTCTCGGTTTTTTT | 188 |
| BX2-C045-AS-V2-2 | TTTTTTTTTGCTCCGTCCTCGGTTTTTTT | 189 |
| BX2-C045-AS-V3-2 | TTTTTTTTTGCTCCTTCCTCGGTTTTTTT | 190 |
| BX2-C045-AS-V4-2 | TTTTTTTTTGCGCCATCCTCGGTTTTTTT | 191 |
| BX2-C045-AS-V5-2 | TTTTTTTTTGCTCCCCTCTCGGTTTTTTT | 192 |
| BX2-C050-SE-V1-1 | TTTTTTTTGCGCCATGGATAGTTTTTTT | 193 |
| BX2-C050-SE-V2-1 | TTTTTTTTTCGCCGTGGATATTTTTTTT | 194 |
| BX2-C050-SE-V3-1 | TTTTTTTTTTGCCGTGGGTGTTTTTTTT | 195 |
| BX2-C050-SE-V3-1 | TTTTTTTTTTCCGTGGGTGGATTTTTTT | 196 |
| BX2-C050-AS-V2-2 | TTTTTTCTCTCTATCCACGGCGCTTTTTTT | 197 |
| BX2-C054-AS-V1-2 | TTTTTTTTCCTCCTGCTCCACCTTTTTTT | 198 |

TABLE 5-continued

| Probe | Sequence | SEQ ID |
|---|---|---|
| BX2-C054-AS-V2-2 | TTTTTTTTCCTCCTGCTCTATCTTTTTTTT | 199 |
| BX2-C054-AS-V3-2 | TTTTTTTTCCCTCTTGCTCTATCTTTTTTTT | 200 |
| BX2-C058-SE-V1-1 | TTTTTTTTTCGGAGTATTGGGATTTTTTTT | 201 |
| BX2-C058-SE-V2-1 | TTTTTTTTTCCGGAATATTGGGATTTTTTTT | 202 |
| BX2-C063-AS-V1-2 | TTTTTTTTCCCTGTGTGTTCCGTCTTTTTTT | 203 |
| BX2-C063-AS-V2-2 | TTTTTTTTCCCTGTGTCTCCCGTCTTTTTTT | 204 |
| BX2-C063-AS-V3-2 | TTTTTTTTCCCCGTGTCTCCCGTCTTTTTTT | 205 |
| BX2-C063-AS-V4-2 | TTTTTTTTCCCCGTGTCTCCCCTCTTTTTTT | 206 |
| BX2-C067-SE-V1-1 | TTTTTTTTTCAGATCTCCAAGACTTTTTTTT | 207 |
| BX2-C067-SE-V2-1 | TTTTTTTTTCAGATCTTCAAGACTTTTTTTT | 208 |
| BX2-C067-SE-V3-1 | TTTTTTTTTCAGATCTACAAGGCTTTTTTTT | 209 |
| BX2-C067-SE-V4-1 | TTTTTTTTTCAGATCTGCAAGACTTTTTTTT | 210 |
| BX2-C067-SE-V5-1 | TTTTTTTTTAGATCTGCAAGGCTTTTTTTTT | 211 |
| BX2-C067-SE-V6-1 | TTTTTTTTTCGGAACATGAAGGTTTTTTTTT | 212 |
| BX2-C067-SE-V7-1 | TTTTTTTTTCAGAAGTACAAGCGCTTTTTTT | 213 |
| BX2-C067-SE-V8-1 | TTTTTTTTTCAGATCTAGAAGACTTTTTTTT | 214 |
| BX2-C067-SE-V6-2 | TTTTTTTTTACGGAACATGAAGTTTTTTTTT | 215 |
| BX2-C067-SE-V7-2 | TTTTTTTTTCAGAAGTACAAGCGTTTTTTTT | 216 |
| BX2-C067-SE-V8-2 | TTTTTTTTTAGATCTACAAGACCTTTTTTTT | 217 |
| BX2-C069-SE-V1-1 | TTTTTTTTTTAAGACCAACACATTTTTTTTT | 218 |
| BX2-C069-SE-V2-1 | TTTTTTTTTTAAGGCCCAGGCACTTTTTTTT | 209 |
| BX2-C069-SE-V3-1 | TTTTTTTTTTAAGGCCAAGGCACTTTTTTTT | 220 |
| BX2-C069-SE-V4-1 | TTTTTTTTTTAAGGCCTCCGCGCTTTTTTTT | 221 |
| BX2-C069-SE-V5-1 | TTTTTTTTTTAAGCGCCAGGCACTTTTTTTT | 222 |
| BX2-C069-SE-V1-2 | TTTTTTTTTTAGACCAACACACTTTTTTTTT | 223 |
| BX2-C069-SE-V2-2 | TTTTTTTTTAAGGCCCAGGCACATTTTTTTT | 224 |
| BX2-C069-SE-V3-2 | TTTTTTTTTAAGGCCAAGGCACATTTTTTTT | 225 |
| BX2-C069-SE-V4-2 | TTTTTTTTTGAAGGCCTCCGCGCTTTTTTTT | 226 |
| BX2-C069-SE-V5-2 | TTTTTTTTTCAAGCGCCAGGCATTTTTTTTT | 227 |
| BX2-C069-SE-V4-3 | TTTTTTTCGAAGGCCTCCGCGCTTTTTTTTT | 228 |
| BX2-C074-SE-V1-1 | TTTTTTTTTCAGACTTACCGAGCTTTTTTTT | 229 |
| BX2-C074-SE-V2-1 | TTTTTTTTTACAGACTGACCGATCTTTTTTT | 230 |
| BX2-C077-SE-V1-1 | TTTTTTTTTGCAGGCTCTCTCGTCTTTTTTT | 231 |
| BX2-C077-SE-V2-1 | TTTTTTTTTGCAGGTTCTCTCGTCTTTTTTT | 232 |
| BX2-C077-SE-V1-2 | TTTTTTTTTGCAGGTCCTCTCGTCTTTTTTT | 233 |
| BX2-C077-SE-V2-2 | TTTTTTTTTGCAGGCTCACTCGTCTTTTTTT | 234 |
| BX2-C077-SE-V3-2 | TTTTTTTTTGCAGGCCCACTCGTCTTTTTTT | 235 |
| BX2-C081-SE-V1-2 | TTTTTTTTTTGGAACCTGCGCGTTTTTTTTT | 236 |
| BX2-C081-SE-V2-2 | TTTTTTTCTCGGATCGCGCTCCGTCTTTTTT | 237 |
| BX2-C081-SE-V3-2 | TTTTTTTTTGCACCGCGCTCCGTCTTTTTTT | 238 |
| BX2-C081-SE-V4-2 | TTTTTTTCTCGGACCCTGCTCCGTCTTTTTT | 239 |

TABLE 6

| Probe | Sequence | SEQ ID |
|---|---|---|
| BX3-C094-SE-V1-1 | TTTTTTTTTCCTCACACCCTCCTTTTTTTTT | 240 |
| BX3-C094-SE-V2-1 | TTTTTTTTTTCTCACATCATCCATTTTTTTT | 241 |
| BX3-C094-AS-V1-1 | TTTTTTTTTCGGAGGGTGTGAGTTTTTTTTT | 242 |
| BX3-C094-AS-V2-1 | TTTTTTTTTTGGATGATGTGAGATTTTTTTT | 243 |
| BX3-97/99-SE-V1-1 | TTTTTTTTTAGAGGATGTACGGTCTTTTTTT | 244 |
| BX3-97/99-SE-V2-1 | TTTTTTTTTAGAGCATGTACGGTCTTTTTTT | 245 |
| BX3-97/99-AS-V1-1 | TTTTTTTTTCCGTACATCCTCTTTTTTTTTT | 246 |
| BX3-97/99-AS-V2-1 | TTTTTTTTTCCGTACATGCTCTTTTTTTTTT | 247 |
| BX3-C103-SE-V1-1 | TTTTTTTTTACGTGGGGCCGTTTTTTTTTTT | 248 |
| BX3-C103-SE-V3-1 | TTTTTTTTTACCTGGGGCCGTTTTTTTTTTT | 249 |
| BX3-C103-AS-V1-1 | TTTTTTTTTCTCGGCCCCACGTTTTTTTTTT | 250 |
| BX3-C103-AS-V3-1 | TTTTTTTTTCTCGGCCCCAGGTTTTTTTTTT | 251 |
| BX3-C114-SE-V1-1 | TTTTTTTTGGGCATAACCAGTCTTTTTTTTT | 252 |
| BX3-C114-SE-V2-1 | TTTTTTTTTGGGCATGACCAGCTTTTTTTTT | 253 |
| BX3-C114-AS-V1-1 | TTTTTTTCCACTGGTTATGCCCTTTTTTTTT | 254 |
| BX3-C114-AS-V2-1 | TTTTTTTCTCTGGTCATGCCCTTTTTTTTTT | 255 |
| BX3-C116-SE-V1-1 | TTTTTTTCTACCAGTACGCCTATTTTTTTTT | 256 |
| BX3-C116-SE-V2-1 | TTTTTTTCTACCAGTCCGCCTATTTTTTTTT | 257 |
| BX3-C116-AS-V1-1 | TTTTTTTTTAGGCGTACTGGTATTTTTTTTT | 258 |
| BX3-C116-AS-V2-1 | TTTTTTTTTTAGGCGGACTGGTTTTTTTTTT | 259 |
| BX3-C121-SE-V1-1 | TTTTTTTTGGCAAGGATTACATTTTTTTTTT | 260 |
| BX3-C121-SE-V2-1 | TTTTTTTTTGGCAAAGATTACATCTTTTTTT | 261 |
| BX3-C121-AS-V1-1 | TTTTTTTATGTAATCCTTGCCTCTTTTTTTT | 262 |
| BX3-C121-AS-V2-1 | TTTTTTTGATGTAATCTTTGCCTCTTTTTTT | 263 |
| BX3-C131-SE-V1-1 | TTTTTTTTTGACCTGAGCTCCCTTTTTTTTT | 264 |
| BX3-C131-SE-V2-1 | TTTTTTTTTTACCTGCGCTCCTTTTTTTTTT | 265 |
| BX3-C131-AS-V1-1 | TTTTTTTTTGGAGCTCAGGTCTCTTTTTTTT | 266 |
| BX3-C131-AS-V2-1 | TTTTTTTTTTAGGAGCGCAGGTTTTTTTTTT | 267 |
| BX3-C135-SE-V1-1 | TTTTTTTTTACCGCGGCGGATTTTTTTTTTT | 268 |

TABLE 6-continued

| Probe | Sequence | SEQ ID |
|---|---|---|
| BX3-C135-SE-V2-1 | TTTTTTTTTACCGCCGCGGATTTTTTTTTT | 269 |
| BX3-C135-AS-V1-1 | TTTTTTTTCTTCCGCCGCGGTTTTTTTTT | 270 |
| BX3-C135-AS-V2-1 | TTTTTTTTCTTCCGCGGCGGTTTTTTTTT | 271 |
| BX3-C143-SE-V1-1 | TTTTTTTTCTCAGATCACCCATTTTTTTT | 272 |
| BX3-C143-SE-V2-1 | TTTTTTTTCTCAGATCTCCCATTTTTTTT | 273 |
| BX3-C143-AS-V1-1 | TTTTTTTTTGGGTGATCTGAGTTTTTTTT | 274 |
| BX3-C143-AS-V2-1 | TTTTTTTTTGGGAGATCTGAGTTTTTTTT | 275 |
| BX3-C145-SE-V1-1 | TTTTTTTTCCCCAGCGCAAGTCTTTTTTT | 276 |
| BX3-C145-SE-V2-1 | TTTTTTTTCCCCAGCTCAAGTGTTTTTTT | 277 |
| BX3-C145-AS-V1-1 | TTTTTTTTTACTTGCGCTGGGCTTTTTTT | 278 |
| BX3-C145-AS-V2-1 | TTTTTTTTCACTTGAGCTGGGCTTTTTTT | 279 |
| BX3-C152-SE-V1-1 | TTTTTTTTTCCCGTGTGGCGTTTTTTTTT | 280 |
| BX3-C152-SE-V2-1 | TTTTTTTTTCCCGTGAGGCGTTTTTTTTT | 281 |
| BX3-C152-AS-V1-1 | TTTTTTTTCTCGCCACACGGGTTTTTTTT | 282 |
| BX3-C152-AS-V2-1 | TTTTTTTTCTCGCCTCACGGGTTTTTTTT | 283 |
| BX3-C156-SE-V1-1 | TTTTTTTTAGCAGCTGAGAGCTCTTTTTT | 284 |
| BX3-C156-SE-V3-1 | TTTTTTTTTAGCAGCGGAGAGTTTTTTTT | 285 |
| BX3-C156-AS-V1-1 | TTTTTTTTTCTCTCAGCTGCTCTTTTTTT | 286 |
| BX3-C156-AS-V3-1 | TTTTTTTTTCTCTCCGCTGCTTTTTTTTT | 287 |
| BX3-C163-SE-V1-1 | TTTTTTTTTGGCCTGTGCGTGTTTTTTTT | 288 |
| BX3-C163-SE-V2-1 | TTTTTTTTTGGCGAGTGCGTGTTTTTTTT | 289 |
| BX3-C163-AS-V1-1 | TTTTTTTCTCACGCACAGGCCTCTTTTTT | 290 |
| BX3-C163-AS-V2-1 | TTTTTTTCTCACGCACTCGCCTCTTTTTT | 291 |

EXAMPLE 4

Microarray Manufacture

Microarrays are manufactured using methods previously described in Belosludtsev et al. (17). Briefly, substrates used are silica slides cleaned in an ultrasonic bath with detergent (2 minutes) followed by washing with distilled water (3×) and methanol (2×) and drying (30 minutes at 40° C.). Slides are silanized with 3-aminopropyltrimethoxysilane or 3-glycidoxypropyltrimethoxysilane in vapor phase in equilibrium with a 50% silane/p-xylene solution in a vacuum oven at 25 in. Hg overnight at 70-80° C. with cleaned slides assembled in a rack.

Commercially available oligonucleotides (Midland Certified Reagent Co. Midland, Tex.) are deposited as 1 nl solutions in distilled water at 5 µM for aminosilanized slides upon the silanized surface using a microarrayer. After "printing" oligonucleotides, the slides are dried for 15 min at 40° C. or overnight at room temperature and capped with acetic anhydride in vapor phase by placing a Petri dish with a solution of 3 ml of acetic anhydride in 3 ml of dimethyl formamide (DMF) in a vacuum oven at 22 in Hg for 1 h at 50° C. The acetylated amino-derivatized slides are capped with succinic anhydride by dipping slides in a tank with 0.5 M succinic anhydride in DMF at room temperature for 1 h. Slides are cleaned by washing in acetone (3×), in distilled water (2×), and again in acetone (2×). As a quality control, 30 ml of fluorescent-labeled oligonucleotide in hybridization buffer is deposited onto the slide surface. If no background is observed after 15 min, slides would be considered ready for hybridization experiments.

A comparison of adsorptive vs covalent strategies for oligonucleotide attachment to a planar glass substrate was made. Covalent attachment was obtained by reaction of a 5'-amino-modified oligonucleotide with an epoxysilanized surface, a standard method in the art for covalent attachment to surfaces, which yields a terminal secondary amine linkage. Comparison of experimental and calculated density gives evidence that a densely packed monolayer of oligonucleotides was formed during the adsorption process and length dependency studies demonstrate that a densely packed probe film can be formed for probes as long as 36 bases. In further determinations of the stability and structure of the immobilized target, it was found that for short oligonucleotides up to 36 mers, a novel ribbon to form of single stranded DNA is formed on the surface (23). The hybridization selectivity and specificity are similar to a fully upright single stranded DNA molecule covalently attached to the surface.

EXAMPLE 5

Validation of Sample Collection and Extraction

Figure 2A:
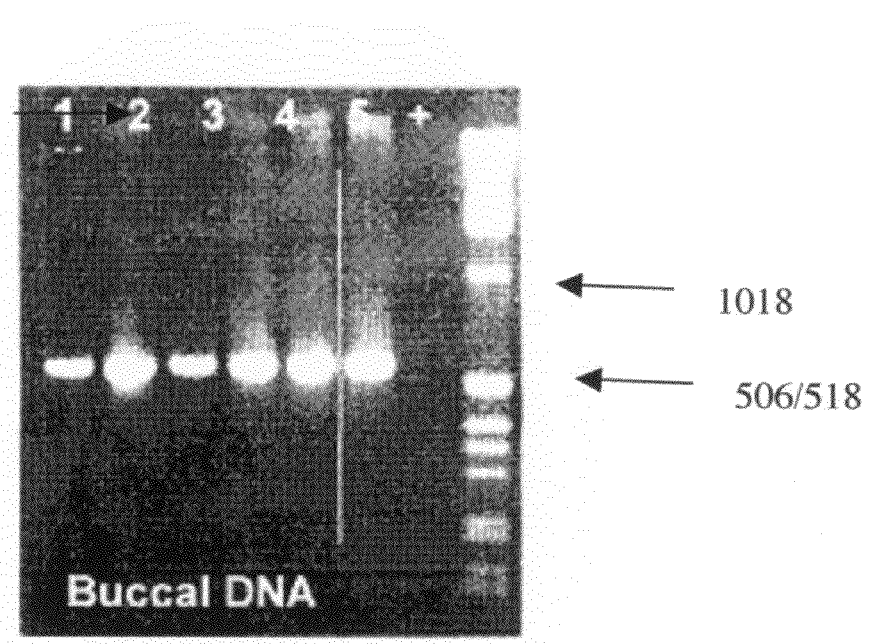
Figure 2B:
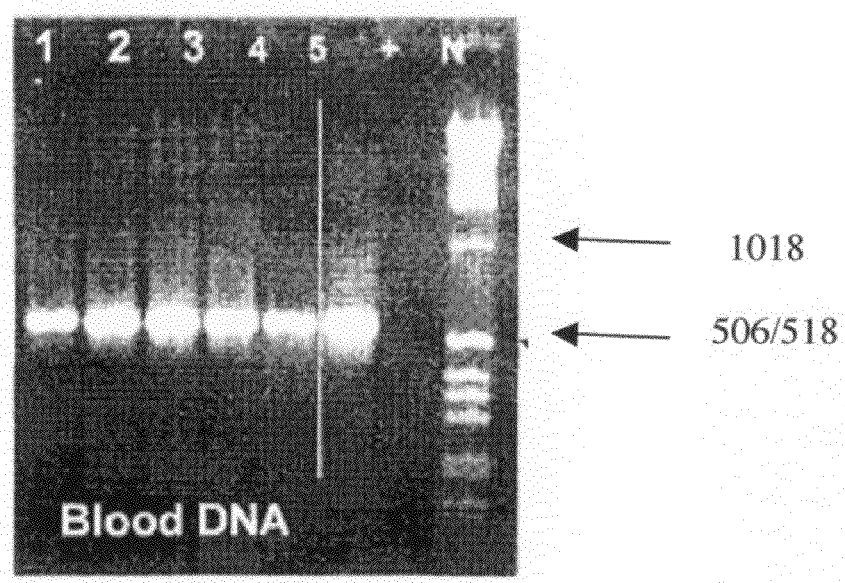

The "mouthwash" method (21) can be used to collect samples. This technique of sample collection is ideally suited for the collection of buccal-derived DNA for large-scale population studies and for collecting samples from geographically dispersed large-scale population studies. The "mouthwash" method does not require any medical supervision. The technique has been shown to preserve the integrity of the sample for up to 1 week as compared to freshly prepared DNA (FIGS. 2A-2B), even on exposure to a variety of temperature conditions.

Briefly, buccal cells are collected by vigorous mouth washing for about 45 seconds with a mouthwash liquid or any other biocompatible liquid followed by spitting into a 10 ml jar. The jar is sealed and mailed. On arrival, cells are pelleted and the cell pellet is dissolved at 25° C. in 100 µl of a solution of Tris-EDTA and 1% SDS for 1 hour with intermittent vortexing. This suspension is applied directly to GenVault elements (13 µl each). Subsequent to drying, DNA is isolated by two saline washes, at which time it remains bound to the porous element. DNA is then released from the element by a single 5 minute wash at 25° C. in GenVault release buffer. DNA thus released, about 1 µg/element, can be used for PCR without additional purification.

Buccal cells can also be collected using a Fitzco Dacron cheek swab. Briefly, a swab is collected either from the right or left cheek and the swab tip is placed in a spin basket within a microfuge tube, air dried overnight and then capped for storage. The tip when required is rehydrated by direct addition of 200 ml SRB and then heated for 4 hours at 55° C. Sample is then harvested from the spin basket and centrifuged for 1 minute at 10,000 G. At least 90% fluidic recovery is obtained. The resulting material can either be processed by Argylla PrepParticles or by batchwise clean-up with a Qiagen column, per manufacturers recommendations. Table 7 compares DNA yields from cheek swabs extracted with the FBI's stain extraction buffer and then using Argylla (A) and Qiagen (Q) for each of 5 volunteers.

TABLE 7

| Volunteer | DNA conc (ng/µl) (×45 µl eluate) = | DNA (ng) |
|---|---|---|
| BI (A) | 15.4 | 693 |
| BI (Q) | 41.3 | 1859 |
| RE (A) | 59.2 | 2664 |
| RE (Q) | 50 | 2250 |
| MH (A) | 67.9 | 3056 |
| MH (Q) | 44.1 | 1985 |
| DI (A) | 14.9 | 671 |
| DI (Q) | 13.2 | 594 |
| JU (A) | 29.6 | 1332 |
| JU (Q) | 18.5 | 833 |

Figure 3A:
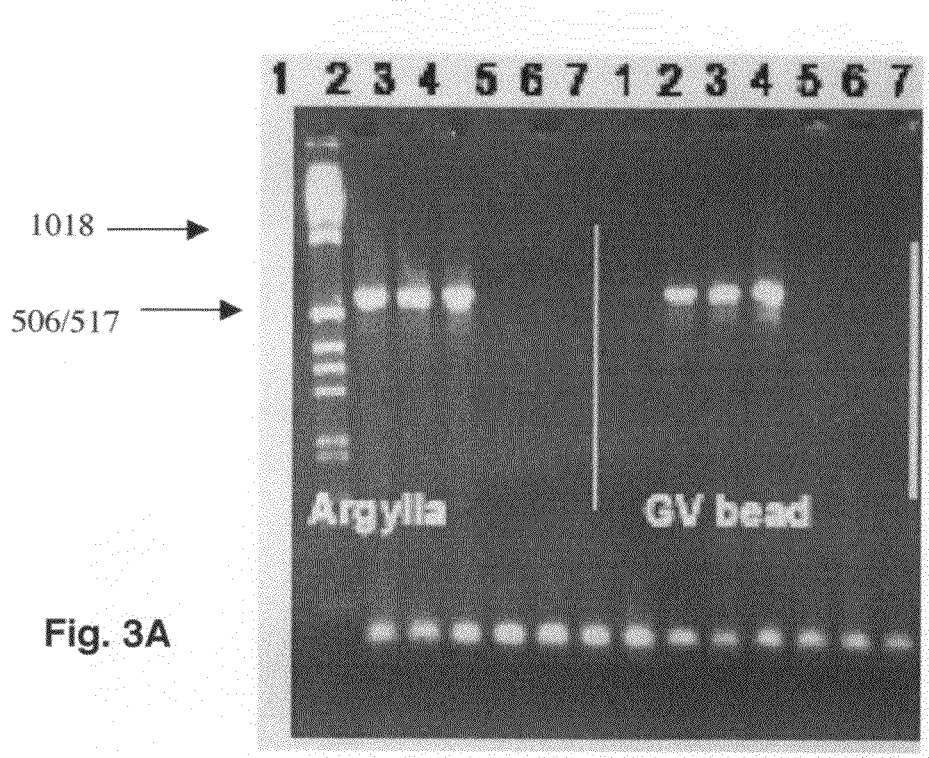
Figure 3B:
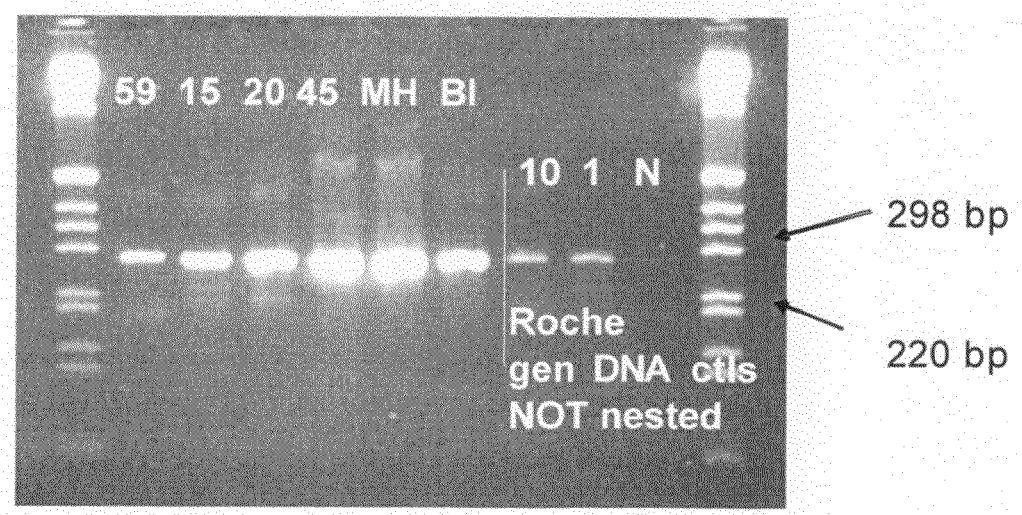

FIG. 3A demonstrates that the DNA extracted from two of the volunteers by the cheek swap method provides an excellent PCR product for HLA-B. UCLA standards are compared to the PCR products derived from buccal DNA samples. As seen in FIG. 3B, HLA-B specific PCR reactions from buccal swab collection are quantitatively similar to those obtained from the pure UCLA reference standards.

EXAMPLE 6

Image Analysis and Pattern Recognition

Figure 4A:
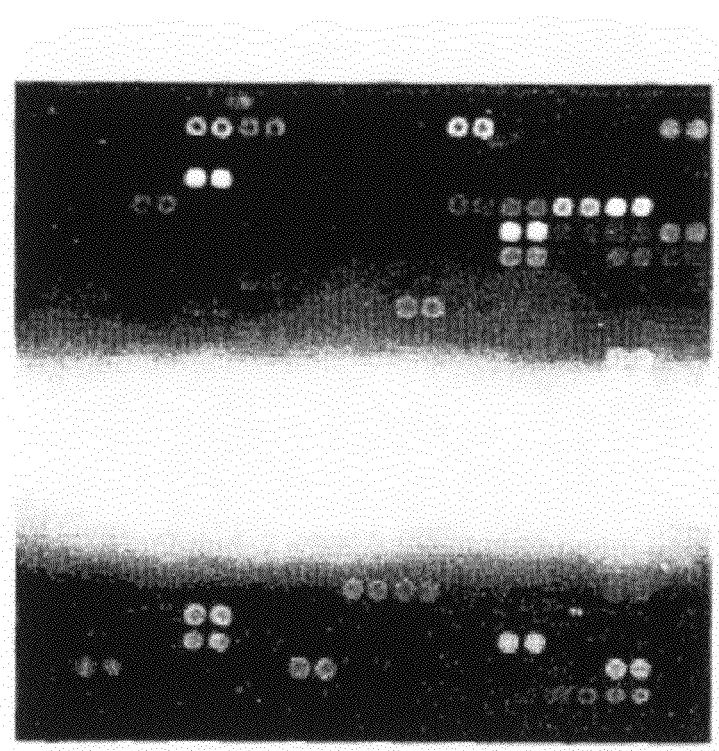
Figure 4B:
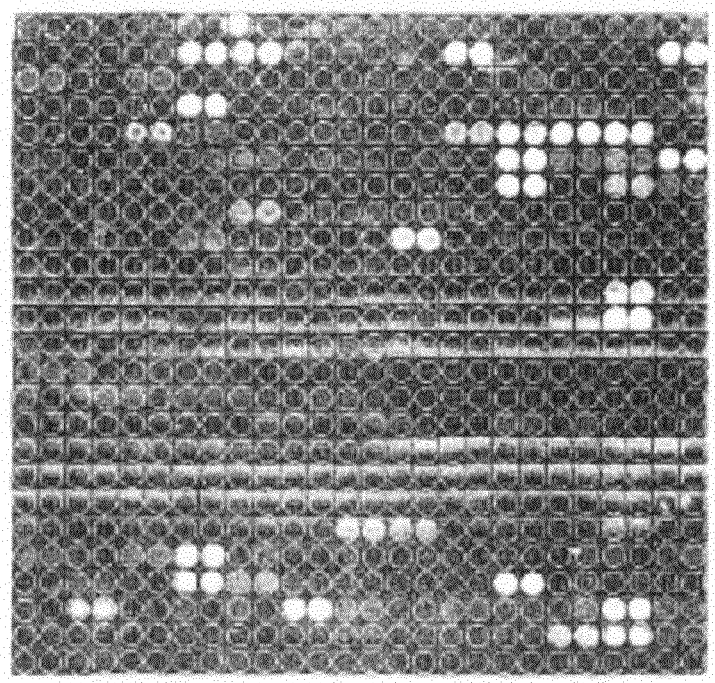
Figure 5A:
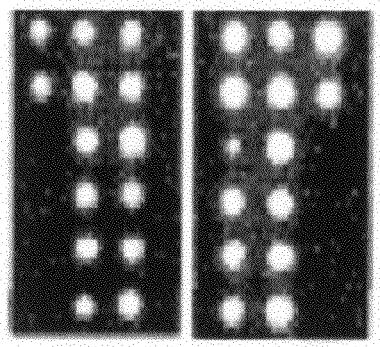
Figure 5B:
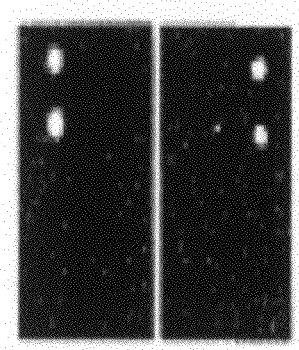
Figure 5C:
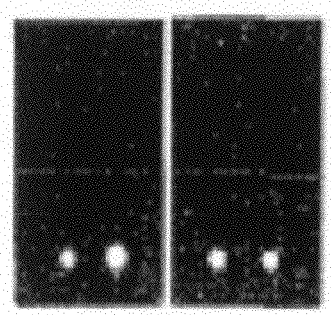
Figure 5D:
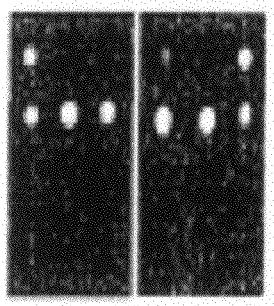

Digitally captured microarray images are analyzed using the algorithms in the ImageAnalyzer software. Briefly, the edge detection methods are employed to substract the background (FIG. 4A) from the images, to produce a clean pattern at a pre-defined threshold above the background (FIG. 4B). The pattern recognition and the generation of a 2-D bar code for the assignment of the HLA type is based on the hybridized spot patterns and their spatial relationships to each of the HLA type. Each of the alleles of the HLA type has a set pattern of spots which would be used as a barcode.

EXAMPLE 7

K-ras model: genotyping and detection of SNPs on Adsorptive Microarrays

Amplicon Generation and Oligonucleotide Probes

The microarrays used in HLA-typing have been used successfully in identifying and assigning genotypes, differing from the wild type by a single nucleotide polymorphism, of K-ras locus. The 152-bp K-ras amplicon was generated by the polymerase chain reaction. Wild-type amplicaon (K-ras 1) was obtained by amplification of a commercial genomic DNA source (Sigma). K-ras 2 and K-ras 7 mutants were obtained by amplification of human genomic DNA from cell lines A549 and SW 480, respectively. The PCR protocol was the following: one pre-PCR cycle at 94° C. for 12 min, 60° C. for 1 min and 72° C. for 1 min; 35 PCR cycles at 95° C. for 1 min, 57° C. for 1 min, 72° C. for 1 min; hold cycle at 72° C. for 7 min, 4° C. hold. PCR primers for k-ras amplicons were labeled with digoxigenin at their 5' ends and had the following sequences: 5'-DIG-ACTGAATATAAACTTGTGGTAGT-TGGACCT-3' (SEQ ID NO: 292) and 5'-DIG-TCAAA-GAATGGTCCTGCACC-3' (SEQ ID NO: 293). K-ras amplicons had different point mutations in codon 12. Specific oligonucleotides were designed to serve as microarray capture probes as shown in Table 7. The underlined nucleotide corresponds to the point mutation.

TABLE 8

| SEQ ID | Sense | SEQ ID | Antisense |
|---|---|---|---|
| 294 | GACCTGGTGGCG | 301 | CGCCACCAGGTC |
| 295 | GACCT<u>A</u>GTGGCG | 302 | CGCCAC<u>T</u>AGGTC |

TABLE 8-continued

| SEQ ID | Sense | SEQ ID | Antisense |
|---|---|---|---|
| 296 | GACCT<u>T</u>GTGGCG | 303 | CGCCAC<u>T</u>AGGTC |
| 297 | GACCT<u>C</u>GTGGCG | 304 | CGCCAC<u>G</u>AGGTC |
| 298 | GACCTG<u>A</u>TGGCG | 305 | CGCCAT<u>C</u>AGGTC |
| 299 | GACCTG<u>C</u>TGGCG | 306 | CGCCAC<u>G</u>AGGTC |
| 300 | GACCTG<u>T</u>TGGCG | 307 | CGCCAC<u>A</u>AGGTC |

Hybridization and Pattern Detection

A prehybridization solution, containing 150 mM sodium citrate, with respect to sodium ion concentration, 5×Denhardt's solution, pH 8.0 was applied to the array for at least 10 min. The solution was vacuumed off and hybridization solution (1 nM amplicon, 0.1 mM chaperone, 150 mM sodium citrate with respect to sodium, 5×Denhardt's solution, pH 8.0) was applied to the array. In these studies, only amplicons complementary to capture probes K-ras 1, K-ras 2, K-ras 7 were used. After 2 h of hybridization, the array was washed two times in 100 mM sodium citrate with respect to sodium, 10 min each, followed by a brief rins in 13 SSC. The digoxigenin-labeled amplicon was detected using anti-digoxigenin antibody linked to alkaline phosphatase (Boehringer Mannheim) at 1:1000 dilution in the blocking buffer from the ELF-97 mRNA In Situ Hybridization Kit (Molecular Probes), followed by washing in buffer A from the same kit and by application of ELF as described in the kit, which is a substrate for alkaline phosphatase. After cleavage by alkaline phosphatase, ELF molecules precipitate and become fluorescent under UV excitation. The fluorescence intensities were detected with an Alpha Imager 2000 apparatus and processed using Sigma Plot 3.0 software (FIGS. 5A-5D).

EXAMPLE 8

SNP Detection in HLA-B

HLA-B Validation model

UCLA has assembled a library of 75 highly characterized DNA samples with known HLA type, which is used worldwide as reference standards. This reference set was obtained and the HLA-B hypervariable region was resequenced to obtain a higher resolution understanding of sequence variation in the reference set. As seen in FIGS. 6A-6B, the UCLA-derived data are quite accurate, yielding only 4-5 discrepancies with respect to one-pass re-sequencing.

HLA-B Target Preparation

A 500-bp fragment from exon 2 of HLA-B is obtained by the polymerase chain reaction (PCR) using the primers designed above from test case purified human genomic DNA samples. The following PCR protocol is used to generate the amplified 500 by fragment: one pre-PCR cycle 94° C. for 12 min, 60° C. for 1 min, and 72° C. for 1 min, 35 PCR cycles 95° C. for 1 min, 57° C. for 1 min, 72° C. for 1 min; hold cycle 72° C. for 7 min, 4° C. hold. PCR primers for HLA-B amplicons are modified to contain a T7 polymerase recognition sequence 5' ATGTAATACGACTCACTATAG 3' (SEQ ID NO: 317).

The double-stranded PCR products are isolated by microcolumn purification, then in vitro transcribed in the presence of biotin labeled-ribonucleotides using the HighYield RNA Transcript Labeling Kit (Enzo Labs, Farmingdale, N.Y.). Briefly, the in vitro transcription reaction to generate a single stranded cRNA was done in a 20 microliter reaction volume containing a mix of 75 mM NTPs with rUTP fraction containing 25% biotinylated-rUTP, 10× reaction buffer, T7 Polymerase enzyme (Ambion, Austin, Tex.). The reaction mix is incubated at 37° C. for four hours. In vitro transcribed biotin labeled cRNA is purified using Qiagen RNeasy kit (Qiagen, Valencia, Calif.), quantified, and is fragmented at 94° C. for 35 min in the presence of 1× fragmentation buffer (40 mM Tris-acetate, pH 8.0, 100 mM Kac, 30 mM MgAc). The quality of the RNA is checked before and after fragmentation using formaldehyde agarose gels.

Hybridization and Detection

Prehybridization solution, containing 150 mM sodium citrate, with respect to sodium ion concentration, 5×Denhardt's solution, pH 8.0, is applied to the array for at least 10 min. The prehybridization solution then is vacuumed off and a hybridization solution containing the single stranded labeled cRNA targets in 150 mM sodium citrate, with respect to sodium, and 5×Denhardt's solution, pH 8.0 was applied to the array for hybridization to the HLA microarray. After 2 h of hybridization, the array is washed two times in 100 mM sodium citrate, with respect to sodium, 10 min each, followed by a brief rinse in 1×SSC. Streptavidin linked phycoerythrin is bound to the biotin on the cRNA target (22). The fluorescence intensities are detected with a CCD-based microarray imager (Array Worx, API, Issaquah, Wash.).

HLA-B Chip

Figure 7G:
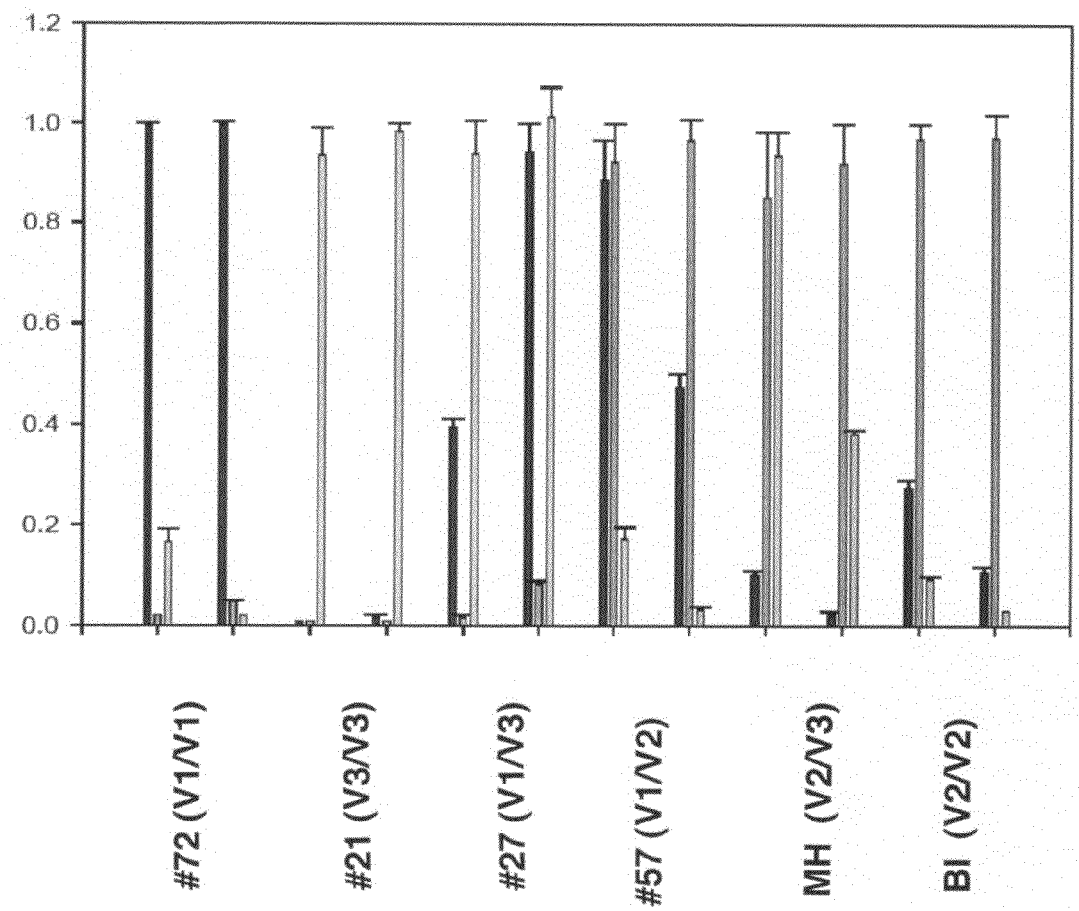

FIGS. 7A-7F show hybridization data for codon 9 of HLA-B. In this array, 9-12 base long probes, lacking the oligo-T flanking sequence, are on the upper right and the corresponding 30 mer oligo-T flanked derivatives are on the left of the microarray. Hybridization was performed with a Cy-3 labeled, 281 bp nested PCR product of known sequence variation obtained from the UCLA HLA reference DNA library (samples 72, 21, 27, 57). Also, shown in FIG. 7F-G are microarray hybridization data to 281 bp products obtained from volunteers (MH, BI). As seen, keeping the probe recognition sequence constant, addition of the oligo-T flank gives rise to a 10-fold increase in hybridization signal relative to the short probe homologues.

In FIG. 7G, spot intensity was manually quantified within the arrays for codon 9. Data in FIG. 7G is presented as six clusters. The first four clusters correspond to hybridization data from UCLA reference samples of known allelotype at codon 9. Codon 9 was chosen because it is triallelic and thus three hybridization probes are required to interrogate known allelic variation. Within each cluster, two sets of probe type were tested: a "long probe" and a "short probe" where the sequence specific sequence at the center had been decreased by one base, in order to determine if specificity could be enhanced. Of importance, it can be seen that for all four of the UCLA reference samples, measured specificity is nearly perfect at codon 9 (FIG. 7G). Those "spots" which should hybridize, as predicted from the UCLA standards are clearly detected. Specificity with respect to single nucleotide resolution is seen to be in excess of 10-fold and in some instances as much as 50-fold among these probes, which allows for unambiguous, hands-free analysis. Nearly identical specificity factors are seen for Codon 50, FIG. 7H. Of particular interest in FIG. 7E-7F is the microarray data derived from buccal swab DNA (MH, BI). These samples are buccal DNA obtained from volunteers, so the HLA type is not yet known. Thus, the values listed beneath the graph are the "HLA calls" for these two samples, rather than external validation: MH being an apparent V2N3 heterozygote and BI being a V2N2 homozygote at Codon 9. The bar graphs reveal that, as was the case for the 4 UCLA standards in FIGS. 7A-7D, clearly defined microarray analysis of buccal DNA was obtained from a standardized 5 ng HLA-B specific PCR reaction.

Figure 7H:
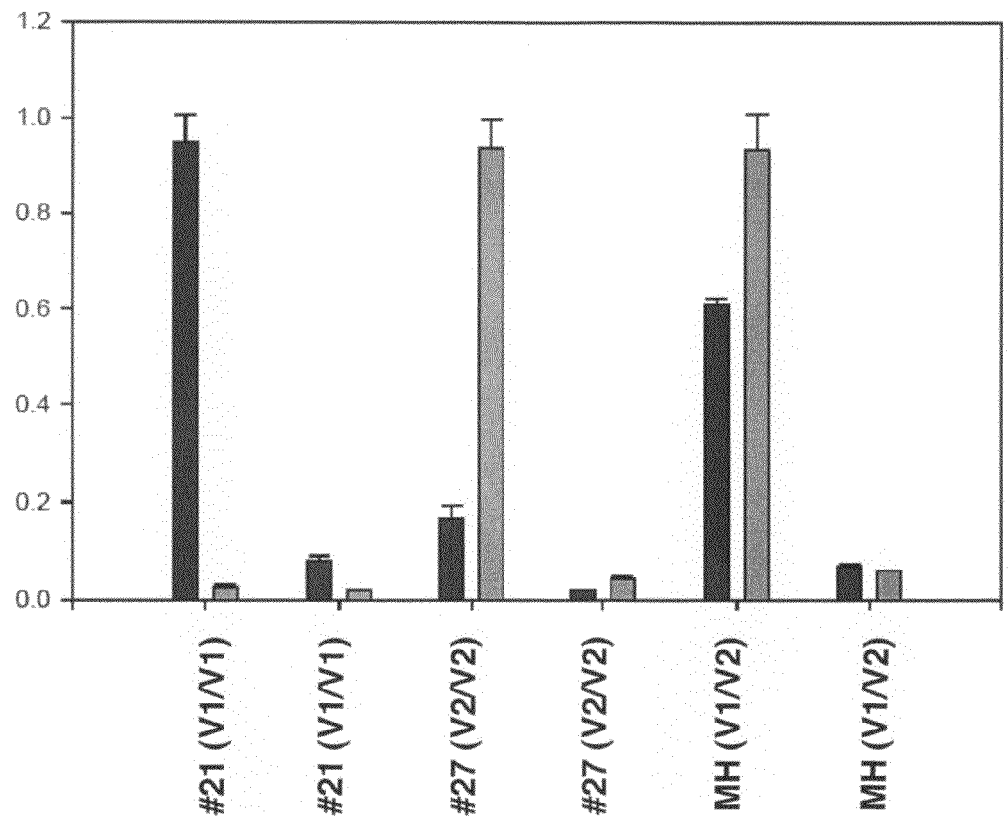

Given that the DNA yield per buccal swab is 500-2000 ng the data of FIGS. 7G-7H demonstrates that each buccal swab collects at least 100 PCR equivalents of DNA. The data also demonstrates that extremely clear HLA calls can be obtained by simple inspection of the data. Because the probes are not chemically modified, and because the oligo-T flanking sequence is a physical "filler", probe synthesis and purification remain very low cost for these microarrays.

EXAMPLE 9

Automated Microarray Signal Analysis

Figure 8:
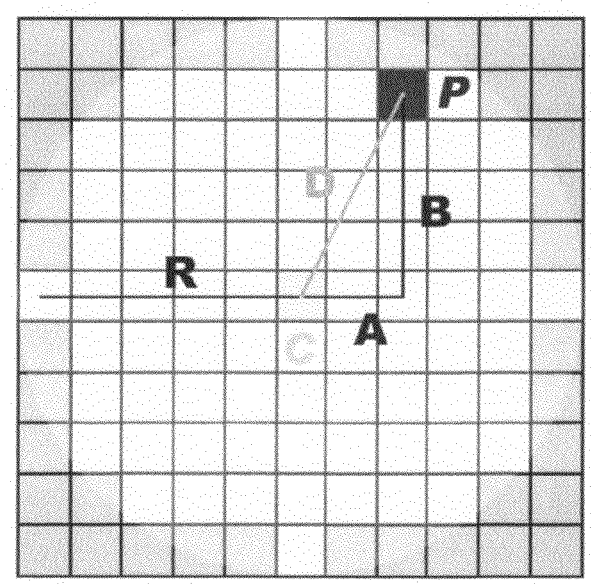
FIG. 8 illustrates the process of determining spot size. P is considered a part of the spot if $D \leq R$, where D=square root of $(A^2+B^2)$.

Before intensities can be extracted from a raw image (as in FIG. 7A), the choice of the appropriate gridding technique must be made (FIG. 8). The grid's structural information is used to layout estimated spot positions. Since microarray spots are symmetric around their centers, an optimization routine can be executed to search for the optimal spot center within the spot's neighboring region. Starting with a raw microarray image, the gridding process includes raw gridding estimation, localized spot center adjustments and structural spot center adjustments. After gridding is complete, it is required to determine how many pixels can be considered to be a part of the spot. For a radius R (measured in pixels), a square of size 2R+1 can easily be constructed in which the spot will be contained. To determine if a pixel is inside the spot the distance D between the given pixel and the center pixel of the square is calculated and seen if it is smaller or equal to the radius R, as illustrated in FIGS. 7A-7F. By making use of efficient data structures to store information for each pixel, the method detailed above can handle microarray images with thousands of spots with modest memory and computational time consumption.

A typical spot in FIG. 7A has radius 15 (pixels), yielding 709 pixels considered to be in the spot. Having defined the boundary of each spot explicitly, the intensities of pixels contained in a certain spot were converted into signal of the spot. The metric exploited takes the arithmetic mean of n most intensive pixels of a spot after the s most intensive pixels are removed from consideration. By doing so the errors involving spikes in intensity values, noise, dust and other extraneous factors are removed. The choice of s and n should reflect the characteristics of the image.

The probes were tested on a series of 12 UCLA samples with the same enhanced 30mer probe set. The outcome of each test is an image similar to the one illustrated in FIG. 7A. To make a statistically sound statement that this technique is successful at performing SNP calling, signals of the same probe from different images (samples) were combined. This necessitated normalization of the signals across images. Given the nature of the experiment, images in HLA typing are expected to mostly contain spots with intensities at the two extremes (If a probe is present in the sample, the corresponding spot will have extremely high intensity. On the other hand, if the probe is absent from the sample, the corresponding spots will have extremely low intensity). The number of spots at each extreme is probe- and sample-specific. A sophisticated normalization scheme to accommodate the characteristics of the images was selected for HLA typing. It takes the arithmetic mean of the markers spots (the 6 bright spots on the left and bottom of FIG. 7A, typically they have intensities of 255 in a 8-bit per pixel format image) as representative of spots with extremely high intensities. The arithmetic mean intensity of the background pixels was chosen as representative of spots with extremely low intensities. The range of an image was then defined as the difference between the arithmetic mean of the marker spots and the background. The images were normalized such that every image had the same range after normalization.

The normalized data of each probe were then divided into two sets, the present set and the absent set. The present set of a probe contains signals from images (samples) where the probe is present. On the other hand, the absent set contains signals from images (samples) where the probe is not present. The Mann-Whitney U tests were performed between the present set and the absent set for each probe. The resulting two-tailed p-values were in the range of 2% to $5 \times 10^{-7}$%, which indicated that the difference in signals of a probe being present in the sample and absent in the sample were statistically significant at the 2% level. These analyses are presented in Table 8. The U statistic of the test is 44, which is the highest for set size 22 and 2, i.e., $2.16 \times 10^{-2}$ is the smallest p-value for set size 22 and 2.

TABLE 9

| Probe | | Set Size | p-value | Significance |
|---|---|---|---|---|
| Codon 50 (A) | Present set | 28 | $4.76 \times 10^{-9}$ | highly |
| | Absent set | 20 | | highly |
| Codon 50 (G) | Present set | 24 | $1.81 \times 10^{-9}$ | highly |
| | Absent set | 24 | | highly |
| Codon 09 (C) | Present set | 8 | $8.88 \times 10^{-5}$ | highly |
| | Absent set | 16 | | highly |
| Codon 09 (G) | Present set | 2 | $2.16 \times 10^{-2}$ | significant |
| | Absent set | 22 | | significant |
| Codon 09 (T) | Present set | 20 | $1.95 \times 10^{-3}$ | highly |
| | Absent set | 4 | | highly |

After the microarray images are converted into SNP calls making use of the Image Analyzer and the data analysis method, the SNP calls are converted to allele calls in an automatic fashion. Accurate and robust allele calls are enabled by the following properties of the final integrated set of probes on the HLA chip: (1) each allele in consideration must be identifiable by at least a certain number of probes; and (2) subsets that identify any two alleles must be different by at least a certain number of probes.

Figure 9:
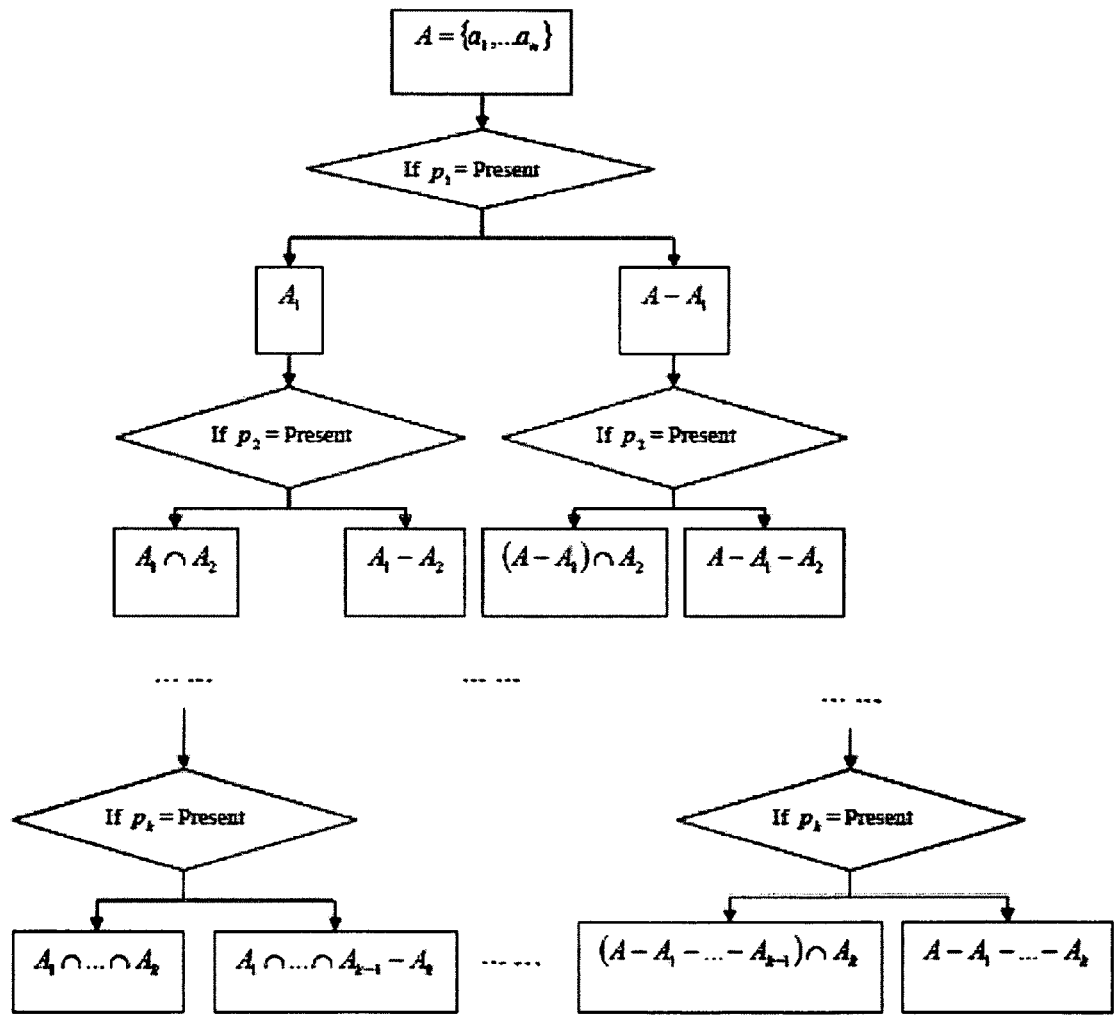
FIG. 9 illustrates a decision tree based approach towards allele calling. The left arrow indicates that the condition in the diamond above is true and the right arrow indicates that the condition in the diamond above is false.

The allele calls are performed in a decision-tree-based approach. For example, let ( )k p p P, . . . 1=be the result of the SNP calls, where i p, k i, . . . , 1=, denotes the presence/absence of an individual probe. Let { } n a a A, . . . 1=be the set all of alleles in consideration, where j a, n j, . . . , 1=, denotes an individual allele. Let i A, k i, . . . , 1=, denote the set of alleles that can be identified by probe i, i.e., at least one allele in i A is expected to be present if i p=Present and vice versa. The allele-calling decision tree is illustrated in FIG. 9. Each node in the tree denotes a subset of A members of which are likely to be present at the current stage of decision-making. The root of the tree is A. Each leaf is a final set of alleles that are determined to be present in the sample. Given the SNP calls of a sample, the set of alleles present in the sample is determined by traversing the decision tree from the root node to one of the leaves based on the presence/absence of each probe. The allele calling process is now a simple tree traversal, which has time complexity linear to the number of probes on the "HLA chip". Thus, the SNP calls can be converted into allele calls on a standard desktop PC (with a 1 GHz CPU and 1 GB RAM) in a matter of seconds. It is possible that the final set of alleles is empty, which implies a hybridization pattern that is unique from all possible patterns given the set of alleles in consideration has been encountered. In this case, the sample is suspected to contain new allele(s) and should be subjected to additional experiments or even sequencing.

EXAMPLE 9

Knowledge-Based Literature Screening Tool to Determine HLA Alleles of Scientific Interest Although more than 10,000 HLA alleles are known, to develop HLA chips, which offer best clinical advantage, it is important to focus on that subset of the total alleles associated with the greatest body of accumulated scientific interest. A knowledge-based literature screening tool to determine such alleles, as defined by citations within the PubMed database is developed in the instant invention. Based upon that first-order knowledge-based screen, a set of approximately 210 alleles have been identified of greatest potential interest. The measurement of significance that was adapted is the number of hits returned while performing a PubMed search with the allele name as the search phrase. Entrez PubMed provides a set of seven server-side programs, known as eUtils, to allow access to Entrez data outside of the regular web query interface. Esearch is an eUtil which searches and retrieves primary IDs and term translations, and optionally retains results for future use in the user's environment. It retrieves the IDs based on different options such as relative date, date ranges, retrieval mode, sort order etc. A script that posts an eUtil URL to NCBI for each search phrase has been written to search for HLA alleles. It searches for the search phrase in the title, the abstract and the full text of the PubMed entries. The script then retrieves the results, which are in XML format. The number of hits for each search phrase, which is contained in the "count" tag in the XML file, can be obtained by parsing the file. Such a search was performed on alleles from 21 HLA genes. Table 9 lists the results for the automated PubMed Search for the 21 HLA Allele Citations.

TABLE 10

| PubMed Citations | No. of Alleles |
|---|---|
| 0 | 1970 |
| 1 | 104 |
| 2-5 | 62 |
| 6-10 | 18 |
| 11-20 | 7 |
| 21-30 | 1 |
| 31-50 | 1 |
| 51-100 | |
| 101-200 | 4 |
| 201-500 | 1 |
| 501-1000 | 2 |
| 1001-2000 | 0 |
| >2000 | 9 |

Table 10 shows that out of the 2179 alleles, 105 of them have two or more citations in PubMed. 210 have one or greater citations. For the 105 alleles that are found to be most significant, i.e., 2 or greater citations, their frequency information in the four major populations in the United States was collected. This list can be further edited relative to the current understanding of the role of HLA in vaccine response, and a set of approximately ten PCR reactions and 400 SNP-specific probes will be designed which uniquely identify the allele set derived from the original set of 210 allele candidates. These serves as the raw material from which to build the HLA Chip and associated protocols for sample processing. All 210 "1 or more" PubMed alleles is listed in the chart in FIG. 10. The number of PubMed citations is listed to the right.

EXAMPLE 10

Candidate Probe Selection for HLA Chips

IMGT/HLA database provides multiple alignment for each HLA locus. The aligned sequences are in a format such that the SNPs are clearly marked. The SNPs are what make one allele different from another. Combinations of SNPs can uniquely represent an allele. From the instant computations it is know that there are 125 SNPs in HLA-B exon 2 and 93 in exon 3, encoding 553 and 562 alleles, respectively. At each location where SNPs occur a short n-mers (13- to 15-nucleotide long) surrounding the SNPs were "filtered" out as templates for candidate probe sequences. There are two types of templates, the simple templates and the composite templates. A simple template contains only one SNP. For instance, there is a SNP at position 36 in exon 3 such that there are no other SNPs occurring within 6 nucleotides on either side. A 13-mer template, consisting of the SNP in the middle and six nucleotides from both sides, was made for this SNP. The template is 5'-TGCGACXTGGGGC (SEQ ID NO: 318), where X denotes the SNP. In allele B*7301, it is an "A" at this position. In allele B*0712 and another 126 alleles, it is a "C". In the rest of HLA-B alleles, including the reference allele, it is a "G". Thus, three probe candidates were made from this template, with the A-, C- and G-polymorphism. In this case, allele B*0712 and all other alleles with a "C" at the SNP site are said to be identified by the probe candidates with the C-polymorphism. Meanwhile, allele B*7301 is said to be uniquely identified by the probe candidate with the A-polymorphism.

Multiple SNPs can occur adjacently or within very short distance such that they fall into the same template. Such templates are known as the composite templates. The 13-mer starting position 254 in exon 3 is an example of a composite template. It contains two SNPs, at position 260 and, separated by a single nucleotide in the middle. The composite template is 5'-GAAGGAXAYGCTG (SEQ ID NO: 319), where X and Y denote the two SNPs. Combinations of the SNPs were taken into considerations. Three probe candidates were made from this template. 31 alleles are identified by the probe candidate with the C- and C-polymorphism. 478 alleles are identified by the probe candidate with the G- and C-polymorphism. The remainder of the HLA-B alleles, including the reference allele, is identified by the probe candidate with the C- and A-polymorphism.

In the next step, the candidate probe sequences that may occur in the rest of the human genome, as well as in ~1000 micro organisms that are expected to appear in the clinical samples with 1-, 2- or 3-mismatches can be excluded from further consideration. This is enabled by a recently developed computational ability known as the "background-blind" technology. The new technology enables performing exact analysis of presence/absence of all subsequences (n-mers) of size up to 22 nucleotides in sequences with order of magnitude of human genome (3 Gb) in a reasonable amount time. Furthermore, it allows explicit consideration of all subsequences deriving from each sequence of interest with 1, 2, and 3 mismatches (in contrast with traditionally used heuristics based alignments like BLAST bases probe/primers design applications).

When a master list such as shown in FIG. 10 is provided, the above computations allow creation of a "complete set" and a "minimal set" of SNP specific probes. The "Complete Set" is the highly redundant compilation of all probes which identify all SNPs in all alleles of a master list like FIG. 10. The Minimal Probe Set can identify the same set of alleles that the complete set identifies, but with a minimal number of probes. This minimization will be done by systematically deleting probes (SNP sites) from the complete set. In each step, the algorithm chooses a probe for deletion. If the remaining set of probes excluding the chosen probe can identify the same set of alleles among the master list, then this particular probe can be deleted without losing any coverage. Otherwise, the algorithm chooses another probe and repeats the above process. It halts when deleting any probe in the set will cause the set to identify fewer alleles. At this point, the set of probes is minimal. To this minimal set, probes that uniquely identify single alleles will be added as controls. Given two samples of allele sequences, these sets of probes can be used to measure the similarity between the two samples, i.e., which allele sequences are present in both sets. This can be extremely useful for transplantation where the compatibility between two individuals is the focus of interests. In other cases, differences among individuals can be identified. For example, two patients may react differently to the same drug or treatment because of the differences in their HLA genes. This is the main motivation behind the concept of the optimal set. An optimal set of probes of a set of alleles can uniquely identify every allele in the set with minimal number of probes. Decision-tree based algorithms can be developed to generate the optimal set.

EXAMPLE 11

Optimal Number of PCRs to Amplify Loci of Interest

Table 11 shows the estimates of the number of primary and in some instances secondary PCR reactions that will be required to amplify the ten loci of interest. Both primary and secondary (nested) PCR will be required for A, B and C. The three primary PCRs can be multiplexed as one reaction, followed by a second multiplex reaction for the nested steps. Thus only 2 PCR reactions would be required for the entire set of Class I genes.

For the Class II genes only 1 exon is required to analyze major SNP variation among the Class II genes. If required nested PCR may be applied to cleanly isolate DRB1. DPA1, DPB1, DQA1 and DQB1 may not require nesting to discriminate against pseudogenes. If the primary PCR for DRB1 can be multiplexed then Class II amplification can be accomplished with one primary and one secondary PCR reaction.

TABLE 11

| | Primary PCR | $2^{nd}$ PCR ex 2 | $2^{nd}$ PCR ex 3 |
|---|---|---|---|
| Class I | | | |
| HLA A | 1 | 1 | 1 |
| HLA B | 1 | 1 | 1 |
| HLA C | 1 | 1 | 1 |
| Class II | | | |
| HLA DRB1 | 1 | 1 | no |
| HLA DRB3 | 1 | 1 | no |
| HLA DRB4 | 1 | 1 | no |
| HLA DRB5 | 1 | 1 | no |
| HLA DPA1 | 0 | 1 | no |
| HLA DPB1 | 0 | 1 | no |
| HLA DQA1 | 0 | 1 | no |
| HLA DQB1 | 0 | 1 | no |

The Following References Are Cited Herein

1. Charron, D. (1997) *Genetic Diversity of HLA: Functional and Medical Implications*. EDK, Paris, France.
2. Marsh, et al. (2000) *HLA FactsBook*. Academic Press, London, UK.
3. Trowsdale and Campbell (1992) *Eur J Immunogenet.* 19, 45-55.

4. Little, A. M. and Parhams P. (1999) *Rev Immunogenet.* 1999, 105-123.
5. Trachtenberg, et al. (2003) *Nat. Med.,* 9, 928-935.
6. Kruskall, et al. (1992) *J Exp Med.* 175, 495-502.
7. McCloskey, et al. (1993) *Handbook of HLA typing techniques.* Hui, K. M., Bidwell, J. L., Eds. Boca Raton, Fla. CRC Press, Inc, 175-247.
8. Wordswoth, P. (1991) *Immunol Lett.,* 29, 37-39.
9. Olerup and Setterquist (1993) *Handbook of HLA typing techniques.* Hui, K. M., Bidwell, J. L., Eds. Boca Raton, Fla. CRC Press, Inc, 149-174.
10. Teutsch, et al. (1996) *Eur J Immunogenet.,* 23, 107-120.
11. Hurley, C. K. (1997) *Tissue Antigens,* 49, 323-328.
12. Dinauer, et al. (2000) *Tissue Antigens,* 55, 364-368.
13. Schena, et al. (1995) *Science* 270, 467-70
14. Saiki, et al. (1989) Proc Natl Acad Sci USA 86 6230-6234.
15. Guo, et al. (2001) *Genome Res.,* 12, 447-457.
16. Wang, et al. (2003) The Eighth Annual Structural Biology Symposium of Sealy Center for Structural Biology, p 157, Galveston, Tex.
17. Belosludtsev, et al. (2001) *Anal. Biochem.* 292, 250-256.
18. Robinson, et al. (2003) *Nuc. Acids Res.* 31, 311-314.
19. Fofanov, et al. (2002) The 2002 Bioinformatics Symposium, Keck/GCC Bioinformatics Consortium, p 14.
20. Fofanov, et al. (2002) The Seventh Structural Biology Symposium of Sealy Center for Structural Biology, p 51, Galveston, Tex.
21. Hayney, et al. (1995) *Mayo Clin Proc.* 70, 951-954.
22. Mitra, et al. (2003) *Analytica Chemica Acta,* 469, 141-148.
23. Lemeshko, et al. (2001) *Nuc. Acids Res.* 29, 3051-3058.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. Hybridization probes for detecting single nucleotide polymorphisms (SNPs) in an HLA gene consisting of SEQ ID NO: 229 or 284.

2. A microarray device for allelotyping an HLA gene, comprising:
   a substrate having a cationic surface; and
   a monolayer comprising one or more of the hybridization probes of claim 1 adsorbed thereto.

3. The microarray device of claim 2, wherein the cationic surface comprises an aminosilane, a quanidinium, tin oxide, aluminum oxide or zirconium oxide or other equivalently charged moiety.

4. The microarray device of claim 2, wherein the substrate is glass, plastic or metal.

5. The microarray device of claim 2, further comprising:
   an oligo-thymidine co-absorbed with the hybridization probes.

6. The microarray device of claim 5, wherein the oligo-thymidine has about 20 to about 40 thymidine.

7. The microarray device of claim 5, further comprising:
   a fluorescent dye linked to the oligo-thymidine 8. The microarray device of claim 2, further comprising:
   a capping agent.

* * * * *